United States Patent
Jewett et al.

(10) Patent No.: US 12,410,456 B2
(45) Date of Patent: *Sep. 9, 2025

(54) CELL-FREE GLYCOPROTEIN SYNTHESIS (CFGPS) IN PROKARYOTIC CELL LYSATES ENRICHED WITH COMPONENTS FOR GLYCOSYLATION

(71) Applicants: Northwestern University, Evanston, IL (US); Cornell University, Ithaca, NY (US)

(72) Inventors: Michael Christopher Jewett, Evanston, IL (US); Jessica Carol Stark, Evanston, IL (US); Matthew P. DeLisa, Ithaca, NY (US); Thapakorn Jaroentomeechai, Ithaca, NY (US)

(73) Assignees: Northwestern University, Evanston, IL (US); Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/811,051

(22) Filed: Jul. 6, 2022

(65) Prior Publication Data

US 2023/0159972 A1  May 25, 2023

Related U.S. Application Data

(60) Division of application No. 16/023,134, filed on Jun. 29, 2018, now Pat. No. 11,453,901, which is a continuation-in-part of application No. PCT/US2016/069512, filed on Dec. 30, 2016.

(60) Provisional application No. 62/273,124, filed on Dec. 30, 2015.

(51) Int. Cl.
| | |
|---|---|
| C12N 15/52 | (2006.01) |
| C07K 14/47 | (2006.01) |
| C12N 1/20 | (2006.01) |
| C12N 15/62 | (2006.01) |
| C12P 19/18 | (2006.01) |
| C12P 21/00 | (2006.01) |

(52) U.S. Cl.
CPC .......... *C12P 21/005* (2013.01); *C07K 14/473* (2013.01); *C12N 1/20* (2013.01); *C12N 15/52* (2013.01); *C12N 15/62* (2013.01); *C12P 19/18* (2013.01); *C12N 2330/50* (2013.01)

(58) Field of Classification Search
CPC ......... C12P 19/00; C12P 19/18; C12P 21/005; C12N 15/52; C07K 14/00
See application file for complete search history.

(56) References Cited

U.S. PATENT DOCUMENTS

| | | |
|---|---|---|
| 4,496,538 A | 1/1985 | Gordon |
| 4,727,136 A | 2/1988 | Jennings et al. |
| 5,478,730 A | 12/1995 | Alakhov et al. |
| 5,556,769 A | 9/1996 | Wu et al. |
| 5,623,057 A | 4/1997 | Marburg et al. |
| 5,665,563 A | 9/1997 | Beckler |
| 5,679,352 A | 10/1997 | Chong et al. |
| 6,168,931 B1 | 1/2001 | Swartz et al. |
| 6,248,334 B1 | 6/2001 | Lees et al. |
| 6,531,131 B1 | 3/2003 | Gu et al. |
| 6,869,774 B2 | 3/2005 | Endo |
| 6,994,986 B2 | 2/2006 | Swartz et al. |
| 7,118,883 B2 | 10/2006 | Inoue et al. |
| 7,189,528 B2 | 3/2007 | Higashide et al. |
| 7,338,789 B2 | 3/2008 | Swartz et al. |
| 7,387,884 B2 | 6/2008 | Suzuki et al. |
| 7,399,610 B2 | 7/2008 | Shikata et al. |
| 8,703,471 B2 | 4/2014 | Aebi et al. |
| 8,999,668 B2 | 4/2015 | DeLisa et al. |
| 2004/0209321 A1 | 10/2004 | Swartz et al. |
| 2005/0054044 A1 | 3/2005 | Swartz et al. |
| 2005/0170452 A1 | 8/2005 | Wildt et al. |
| 2006/0211085 A1 | 9/2006 | Bobrowicz |
| 2006/0234345 A1 | 10/2006 | Schwartz et al. |
| 2006/0252672 A1 | 11/2006 | Betenbaugh et al. |
| 2006/0257399 A1 | 11/2006 | Gerngross et al. |
| 2006/0286637 A1 | 12/2006 | Hamilton |
| 2007/0026485 A1 | 2/2007 | DeFrees et al. |
| 2007/0154983 A1 | 7/2007 | Calhoun et al. |
| 2007/0178551 A1 | 8/2007 | Gerngross |
| 2008/0138857 A1 | 6/2008 | Swartz et al. |
| 2009/0317862 A1 | 12/2009 | Riken |
| 2012/0171720 A1 | 7/2012 | Church et al. |
| 2014/0045267 A1 | 2/2014 | Lajoie et al. |

(Continued)

FOREIGN PATENT DOCUMENTS

| | | |
|---|---|---|
| JP | 2002540075 A | 11/2002 |
| WO | 2003056914 A1 | 7/2003 |

(Continued)

OTHER PUBLICATIONS

Oza, J.P. et al. Robust production of recombinant phosphoproteins using cell-free protein synthesis. Nat Commun 6, 8168 (2015).
Pardee, K. et al. Paper-based synthetic gene networks. Cell 159, 940-54 (2014).
Pardee, K. et al. Portable, on-demand biomolecular manufacturing. Cell 167, 248-259 e12 (2016).
Pettersen, E.F. et al. UCSF Chimera—a visualization system for exploratory research and analysis. J Comput Chem 25, 1605-12 (2004).
Raman, R., Raguram, S., Venkataraman, G., Paulson, J.C. & Sasisekharan, R. Glycomics: an integrated systems approach to structure-function relationships of glycans. Nat Methods 2, 817-24 (2005).

(Continued)

*Primary Examiner* — Maryam Monshipouri
(74) *Attorney, Agent, or Firm* — Quarles & Brady LLP

(57) ABSTRACT

Disclosed are components and systems for cell-free glycoprotein synthesis (CFGpS). In particular, the components and systems include and utilize prokaryotic cell lysates from engineered prokaryotic cell strains that have been engineered to enable cell-free synthesis of glycoproteins.

17 Claims, 22 Drawing Sheets

Specification includes a Sequence Listing.

(56) References Cited

U.S. PATENT DOCUMENTS

| | | | |
|---|---|---|---|
| 2014/0255987 A1* | 9/2014 | Delisa | C12P 21/005 435/68.1 |
| 2014/0295492 A1 | 10/2014 | Jewett et al. | |
| 2015/0259757 A1 | 9/2015 | Jewett et al. | |
| 2018/0016612 A1 | 1/2018 | Jewett | |
| 2018/0298416 A1 | 10/2018 | Jewett | |
| 2019/0284600 A1 | 9/2019 | Jewett et al. | |

FOREIGN PATENT DOCUMENTS

| | | |
|---|---|---|
| WO | 2004013151 A1 | 2/2004 |
| WO | 2004035605 A2 | 4/2004 |
| WO | 2006102652 A2 | 9/2006 |
| WO | 2006119987 A2 | 11/2006 |
| WO | 2007120932 A2 | 10/2007 |
| WO | 2013067523 A1 | 5/2013 |
| WO | 2016023018 A2 | 2/2016 |
| WO | 2017117539 A1 | 7/2017 |

OTHER PUBLICATIONS

Ramirez, A.S. et al. Characterization of the single-subunit oligosaccharyltransferase STT3A from Trypanosoma brucei using synthetic peptides and lipid-linked oligosaccharide analogs. Glycobiology 27, 525-535 (2017).

Rothblatt, J.A. & Meyer, D.I. Secretion in yeast: reconstitution of the translocation and glycosylation of alpha-factor and invertase in a homologous cell-free system. Cell 44, 619-28 (1986).

Rudd, P.M. & Dwek, R.A. Glycosylation: heterogeneity and the 3D structure of proteins. Crit Rev Biochem Mol Biol 32, 1-100 (1997).

Rudd, P.M., Elliott, T., Cresswell, P., Wilson, I.A. & Dwek, R.A. Glycosylation and the immune system. Science 291, 2370-6 (2001).

Salehi, A.S. et al. Cell-free protein synthesis of a cytotoxic cancer therapeutic: Onconase production and a just-add-water cell-free system. Biotechnol J 11, 274-81 (2016).

Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26(3/4):227-259.

Schoborg, J.A. et al. A cell-free platform for rapid synthesis and testing of active oligosaccharyltransferases. bioRxiv (2017).

Schoborg, J.A. et al. A cell-free platform for rapid synthesis and testing of active oligosaccharyltransferases. Biotechnol Bioeng 115, 739-750 (2018).

Schwarz, F. et al. A combined method for producing homogeneous glycoproteins with eukaryotic N-glycosylation. Nat Chem Biol 6, 264-6 (2010).

Schwarz, F. et al. Relaxed acceptor site specificity of bacterial oligosaccharyltransferase in vivo. Glycobiology 21, 45-54 (2011).

Shibutani, M., Kim, E., Lazarovici, P., Oshima, M. & Guroff, G. Preparation of a cell-free translation system from PC12 cell. Neurochem Res 21, 801-7 (1996).

Sinclair, A.M. & Elliott, S. Glycoengineering: the effect of glycosylation on the properties of therapeutic proteins. J Pharm Sci 94, 1626-35 (2005).

Srichaisupakit, A., Ohashi, T., Misaki, R. & Fujiyama, K. Production of initial-stage eukaryotic N-glycan and its protein glycosylation in Escherichia coli. J Biosci Bioeng 119, 399-405 (2015).

Stapleton, J.A. & Swartz, J.R. Development of an in vitro compartmentalization screen for high-throughput directed evolution of [FeFe] hydrogenases. PLoS One 5, e15275 (2010).

Stech, M. et al. Cell-free synthesis of functional antibodies using a coupled in vitro transcription-translation system based on CHO cell lysates. Sci Rep 7, 12030 (2017).

Sun, Z.Z. et al. Protocols for implementing an Escherichia coli based TX-TL cell-free expression system for synthetic biology. J Vis Exp, e50762 (2013).

Tarui, H., Imanishi, S. & Hara, T. A novel cell-free translation/glycosylation system prepared from insect cells. J Biosci Bioeng 90, 508-14 (2000).

Valderrama-Rincon, J.D. et al. An engineered eukaryotic protein glycosylation pathway in Escherichia coli. Nat Chem Biol 8, 434-6 (2012).

Wacker et al., "N-linked glycosylation in Campylobacter jejuni and its functional transfer into E. coli," Science Nov. 29, 2002; 298(5599):1790-3.

Weerapana, E. & Imperiali, B. Asparagine-linked protein glycosylation: from eukaryotic to prokaryotic systems. Glycobiology 16, 91R-101R (2006).

Wolfert, M.A. & Boons, G.J. Adaptive immune activation: glycosylation does matter. Nat Chem Biol 9, 776-84 (2013).

International Search Report and Written Opinion for PCT/US2016/069512 dated Apr. 20, 2017.

International Preliminary Report on Patentability for PCT/US2016/069512 dated Jul. 12, 2018.

Alemka, A., et al., "N-glycosylation of Campylobacter jejuni surface proteins promotes bacterial fitness, Infection and immunity", 2013, vol. 81, No. 5, pp. 1674-1682.

Kienesberger, S., et al., "Comparative genome analysis of Campylobacter fetus subspecies revealed horizontally acquired genetic elements important for virulence and niche specificity", PLoS One, 2014, vol. 9, No. 1, pp. 1-13.

Tan, T., et al., "Hydrogen sulfide formation as well as ethanol production in different media by cysND- and/or cysIJ-inactivated mutant strains of Zymomonas mobilis ZM4", Bioprocess and biosystems engineering, 2013, vol. 36, No. 10, pp. 1363-1373.

Thomassin, JL., et al., "Both group 4 capsule and lipopolysaccharide O-antigen contribute to enteropathogenic Escherichia coli resistance to human alpha-defensin 5", PloS One, 2013, vol. 8, No. 12, pp. 1-12.

Scott, NE., et al., "Comparative proteomics and glycoproteomics reveal increased N-linked glycosylation and relaxed sequon specificity in Campylobacter jejuni NCTC11168 O", Journal of Proteome Research, 2014, vol. 13, No. 11, pp. 5136-5150.

Zhu, Y., et al., "Construction and characterization of pta gene-deleted mutant of Clostridium tyrobutyricum for enhanced butyric acid fermentation", Biotechnology and Bioengineering, 2005, vol. 90, No. 2, pp. 154-166.

Guarino, C. "Investigating Oligosaccharyltransferases of N-Linked Glycosylation Using Escherichia coli." PhD Dissertation; Cornell University. 2013.

Ahn, J.H., Hwang, M.Y., Lee, K.H., Choi, C.Y. & Kim, D.M. Use of signal sequences as an in situ removable sequence element to stimulate protein synthesis in cell-free extracts. Nucleic Acids Res 35, e21 (2007).

Albayrak, C. & Swartz, J.R. Cell-free co-production of an orthogonal transfer RNA activates efficient site-specific non-natural amino acid incorporation. Nucleic Acids Res 41, 5949-63 (2013).

Alberts et al., in Molecular Biology of the Cell, 3d edition, Garland Publishing, 1994.

Baba, T. et al. Construction of Escherichia coli K-12 in-frame, single-gene knockout mutants: the Keio collection. Mol Syst Biol 2, 2006 0008 (2006).

Beaucage et al., 1981, Tetrahedron Letters 22:1859-1862.

Brodel, A.K. et al. IRES-mediated translation of membrane proteins and glycoproteins in eukaryotic cell-free systems. PLoS One 8, e82234 (2013).

Bundy, B.C. & Swartz, J.R. Site-specific incorporation of p-propargyloxyphenylalanine in a cell-free environment for direct protein-protein click conjugation. Bioconjug Chem 21, 255-63 (2010).

Carlson, E.D., Gan, R., Hodgman, C.E. & Jewett, M.C. Cell-free protein synthesis: applications come of age. Biotechnol Adv 30, 1185-94 (2012).

Chen, L. et al. Outer membrane vesicles displaying engineered glycotopes elicit protective antibodies. Proc Natl Acad Sci U S A 113, E3609-18 (2016).

Datsenko, K.A. & Wanner, B.L. One-step inactivation of chromosomal genes in Escherichia coli K-12 using PCR products. Proc Natl Acad Sci U S A 97, 6640-5 (2000).

(56) References Cited

OTHER PUBLICATIONS

Dudley, Q.M., Anderson, K.C. & Jewett, M.C. Cell-Free Mixing of *Escherichia coli* Crude Extracts to Prototype and Rationally Engineer High-Titer Mevalonate Synthesis. ACS Synth Biol 5, 1578-1588 (2016).
Dudley, et al. "Cell-Free Mixing of *Escherichia coli* Crude Extracts to Prototype and Rationally Engineer High-Titer Mevalonate Synthesis," ACS Synth Biol 5 (12), 1578-1588.
Feldman, M.F. et al. Engineering N-linked protein glycosylation with diverse O antigen lipopolysaccharide structures in *Escherichia coli*. Proc Natl Acad Sci U S A 102, 3016-21 (2005).
Glover, K.J., Weerapana, E., Numao, S. & Imperiali, B. Chemoenzymatic synthesis of glycopeptides with PglB, a bacterial oligosaccharyl transferase from Campylobacter jejuni. Chem Biol 12, 1311-5 (2005).
Goodchild, 1990, Bioconjugate Chemistry 1(3): 165-187.
Goshima, N. et al. Human protein factory for converting the transcriptome into an in vitro-expressed proteome. Nature Methods 5, 1011-1017 (2008).
Guarino, C. & DeLisa, M.P. A prokaryote-based cell-free translation system that efficiently synthesizes glycoproteins. Glycobiology 22, 596-601 (2012).
Hagelueken, G. et al. A coiled-coil domain acts as a molecular ruler to regulate O-antigen chain length in lipopolysaccharide. Nat Struct Mol Biol 22, 50-56 (2015).
Hamilton, S.R. et al. Production of complex human glycoproteins in yeast. Science 301, 1244-6 (2003).
Hayes, C. Biomolecular Breadboards:Protocols:cost estimate. http://www.openwetware.org/wiki/Biomolecular_Breadboards:Protocols:cost_estimate. vol. 2017 (2012).
Hebert, D.N., Lamriben, L., Powers, E.T. & Kelly, J.W. The intrinsic and extrinsic effects of N-linked glycans on glycoproteostasis. Nat Chem Biol 10, 902-910 (2014).
Helenius, A. & Aebi, M. Intracellular functions of N-linked glycans. Science 291, 2364-9 (2001).
Imperiali, B. & O'Connor, S.E. Effect of N-linked glycosylation on glycopeptide and glycoprotein structure. Curr Opin Chem Biol 3, 643-9 (1999).
Jackson, K., Kanamori, T., Ueda, T. & Fan, Z.H. Protein synthesis yield increased 72 times in the cell-free PURE system. Integr Biol (Camb) 6, 781-8 (2014).
Jaroentomeechai, T. et al. A Pipeline for Studying and Engineering Single-Subunit Oligosaccharyltransferases. Methods Enzymol 597, 55-81 (2017).
Jervis, A.J. et al. Characterization of the structurally diverse N-linked glycans of *Campylobacter* species. J Bacteriol 194, 2355-62 (2012).
Jewett, M.C., Calhoun, K.A., Voloshin, A., Wuu, J.J. & Swartz, J.R. An integrated cell-free metabolic platform for protein production and synthetic biology. Mol Syst Biol 4, 220 (2008).
Jewett, M.C. & Swartz, J.R. Mimicking the *Escherichia coli* cytoplasmic environment activates long-lived and efficient cell-free protein synthesis. Biotechnol Bioeng 86, 19-26 (2004).
Kaiser, L. et al. Efficient cell-free production of olfactory receptors: detergent optimization, structure, and ligand binding analyses. Proc Natl Acad Sci U S A 105, 15726-31 (2008).
Karim, A.S. & Jewett, M.C. A cell-free framework for rapid biosynthetic pathway prototyping and enzyme discovery. Metab Eng 36, 116-126 (2016).
Kiga, D. et al. An engineered *Escherichia coli* tyrosyl-tRNA synthetase for site-specific incorporation of an unnatural amino acid into proteins in eukaryotic translation and its application in a wheat germ cell-free system. Proc Natl Acad Sci U S A 99, 9715-20 (2002).
Kightlinger, W. et al. Design of glycosylation sites by rapid synthesis and analysis of glycosyltransferases. Nat Chem Biol (2018).
Kowarik, M. et al. N-linked glycosylation of folded proteins by the bacterial oligosaccharyltransferase. Science 314, 1148-50 (2006).
Kwon, Y.C. & Jewett, M.C. High-throughput preparation methods of crude extract for robust cell-free protein synthesis. Sci Rep 5, 8663 (2015).

Lanctot, P.M., Gage, F.H. & Varki, A.P. The glycans of stem cells. Curr Opin Chem Biol 11, 373-80 (2007).
Lingappa, V.R., Lingappa, J.R., Prasad, R., Ebner, K.E. & Blobel, G. Coupled cell-free synthesis, segregation, and core glycosylation of a secretory protein. Proc Natl Acad Sci U S A 75, 2338-42 (1978).
Liu, D. & Reeves, P.R. *Escherichia coli* K12 regains its O antigen. Microbiology 140 ( Pt 1), 49-57 (1994).
Lizak, C., Gerber, S., Numao, S., Aebi, M. & Locher, K.P. X-ray structure of a bacterial oligosaccharyltransferase. Nature 474, 350-5 (2011).
Martin, R.W. et al. Cell-free protein synthesis from genomically recoded bacteria enables multisite incorporation of noncanonical amino acids. Nat Commun 9, 1203 (2018).
Matsuoka, K., Komori, H., Nose, M., Endo, Y. & Sawasaki, T. Simple screening method for autoantigen proteins using the N-terminal biotinylated protein library produced by wheat cell-free synthesis. J Proteome Res 9, 4264-73 (2010).
Merritt, J.H., Ollis, A.A., Fisher, A.C. & DeLisa, M.P. Glycans-by-design: engineering bacteria for the biosynthesis of complex glycans and glycoconjugates. Biotechnol Bioeng 110, 1550-64 (2013).
Meuris, L. et al. GlycoDelete engineering of mammalian cells simplifies N-glycosylation of recombinant proteins. Nat Biotechnol 32, 485-9 (2014).
Mikami, S., Kobayashi, T., Yokoyama, S. & Imataka, H. A hybridoma-based in vitro translation system that efficiently synthesizes glycoproteins. J Biotechnol 127, 65-78 (2006).
Moore, S.J. et al. Rapid acquisition and model-based analysis of cell-free transcription-translation reactions from nonmodel bacteria. Proc Natl Acad Sci U S A 115, E4340-E4349 (2018).
Moreno, S.N., Ip, H.S. & Cross, G.A. An mRNA-dependent in vitro translation system from Trypanosoma brucei. Mol Biochem Parasitol 46, 265-74 (1991).
Musumeci, M.A. et al. In vitro activity of Neisseria meningitidis PglL O-oligosaccharyltransferase with diverse synthetic lipid donors and a UDP-activated sugar. J Biol Chem 288, 10578-87 (2013).
Narang et al., 1979, Meth. Enzymol. 68:90-99.
Ollis, A.A. et al. Substitute sweeteners: diverse bacterial oligosaccharyltransferases with unique N-glycosylation site preferences. Sci Rep 5, 15237 (2015).
Ollis, A.A., Zhang, S., Fisher, A.C. & DeLisa, M.P. Engineered oligosaccharyltransferases with greatly relaxed acceptor-site specificity. Nat Chem Biol 10, 816-22 (2014).
Owczarzy et al., 2008, Biochemistry, 47: 5336-5353.
Ihssen, J., et al., Increased efficiency of Campylobacter jejuni N-oligosaccharyltransferase PglB by structure-guided engineering. Open Biol, 2015. 5(4).
Ihssen, J., et al., Production of glycoprotein vaccines in *Escherichia coli*. Microb Cell Fact, 2010. 9: p. 61.
Imberty, A. and A. Varrot, Microbial recognition of human cell surface glycoconjugates. Curr Opin Struct Biol, 2008. 18 (5): p. 567-76.
Iwashkiw, J.A., et al., Exploiting the Campylobacter jejuni protein glycosylation system for glycoengineering vaccines and diagnostic tools directed against brucellosis. Microb Cell Fact, 2012. 11: p. 13.
Jansson, P. E., et al., Structural studies of the *Escherichia coli* 078 O-antigen polysaccharide. Carbohydr Res, 1987. 165(1): p. 87-92.
Jaroentomeechai, T., et al., Single-pot glycoprotein biosynthesis using a cell-free transcription-translation system enriched with glycosylation machinery. Nat Commun, 2018. 9(1): p. 2686.
Jin, C., Gibani, M.M., Moore, M., Juel, H.B., Jones, E., Meiring, J., Harris, V., Gardner, J., Nebykova, A., Kerridge, S. A., et al. (2017). Efficacy and immunogenicity of a Vi-tetanus toxoid conjugate vaccine in the prevention of typhoid fever using a controlled human infection model of Salmonella Typhi: a randomised controlled, phase 2b trial. Lancet 390, 2472-2480.
Johnson, J.R. (1991). Virulence factors in Escherichia coli urinary tract infection. Clin Microbiol Rev 4, 80-128.
Kalynych, S., R. Morona, and M. Cygler, Progress in understanding the assembly process of bacterial O-antigen. FEMS Microbiol Rev, 2014. 38(5): p. 1048-65.

(56) References Cited

OTHER PUBLICATIONS

Kampf, M.M., et al., In vivo production of a novel glycoconjugate vaccine against Shigella flexneri 2a in recombinant Escherichia coli: identification of stimulating factors for in vivo glycosylation. Microb Cell Fact, 2015. 14: p. 12.

Kim, D.M., and Swartz, J.R. (2001). Regeneration of adenosine triphosphate from glycolytic intermediates for cell-free protein synthesis. Biotechnol Bioeng 74, 309-316.

Knapp, K.G., Goerke, A.R., and Swartz, J.R. (2007). Cell-free synthesis of proteins that require disulfide bonds using glucose as an energy source. Biotechnol Bioeng 97, 901-908.

Kowarik, M., et al., Definition of the bacterial N-glycosylation site consensus sequence. The EMBO Journal, 2006. 25 (9): p. 1957-1966.

Kubick, S., et al., In vitro synthesis of posttranslationally modified membrane proteins. Current Topics in Membranes, 2009. 63(2): p. 25-49.

Kumru, O.S., et al., Vaccine instability in the cold chain: mechanisms, analysis and formulation strategies. Biologicals, 2014. 42(5): p. 237-59.

L'vov, V.L., Shashkov, A.S., Dmitriev, B.A., Kochetkov, N.K., Jann, B., and Jann, K. (1984). Structural studies of the O- specific side chain of the lipopolysaccharide from Escherichia coli O:7. Carbohydr Res 126, 249-259.

Laine, R.A., The Information-Storing Potential of the Sugar Code. Glycosciences: Status and Perspectives, 1997: p. 1-14.

Lehle, L. and W. Tanner, Glycosyl transfer from dolichyl phosphate sugars to endogenous and exogenous glycoprotein acceptors in yeast. Eur J Biochem, 1978. 83(2): p. 563-70.

Lesinski, G.B. and M.A. Westerink, Novel vaccine strategies to T-independent antigens. J Microbiol Methods, 2001. 47 (2): p. 135-49.

Lian, Q., H. Cao, and F. Wang, The cost-efficiency realization in the *Escherichia coli*-based cell-free protein synthesis systems. Appl Biochem Biotechnol, 2014. 174(7): p. 2351-67.

Linton, D., et al., Identification of N-acetylgalactosamine-containing glycoproteins PEB3 and CgpA in Campylobacter jejuni. Mol Microbiol, 2002. 43(2): p. 497-508.

Lizak, C., et al., X-ray structure of a bacterial oligosaccharyltransferase. Nature, 2011. 474(7351): p. 350-355.

Lu, Y., J.P. Welsh, and J.R. Swartz, Production and stabilization of the trimeric influenza hemagglutinin stem domain for potentially broadly protective influenza vaccines. Proc Natl Acad Sci U S A, 2014. 111(1): p. 125-30.

Lu, Z., Madico, G., Roche, M.I., Wang, Q., Hui, J.H., Perkins, H.M., Zaia, J., Costello, C.E., and Sharon, J. (2012). Protective B-cell epitopes of Francisella tularensis O-polysaccharide in a mouse model of respiratory tularaemia. Immunology 136, 352-360.

Lydon, P., Zipursky, S., Tevi-Benissan, C., Djingarey, M.H., Gbedonou, P., Youssouf, B.O., and Zaffran, M. (2014). Economic benefits of keeping vaccines at ambient temperature during mass vaccination: the case of meningitis A vaccine in Chad. Bull World Health Organ 92, 86-92.

Ma, Z. and K. Vosseller, Cancer metabolism and elevated O-GlcNAc in oncogenic signaling. J Biol Chem, 2014. 289 (50): p. 34457-65.

Ma, Z., et al., Glycoconjugate vaccine containing *Escherichia coli* 0157:H7 O-antigen linked with maltose-binding protein elicits humoral and cellular responses. PLoS One, 2014. 9(8): p. e105215.

Marshall, L.E., Nelson, M., Davies, C.H., Whelan, A.O., Jenner, D.C., Moule, M.G., Denman, C., Cuccui, J., Atkins, T. P., Wren, B.W., et al. (2018). An O-antigen glycoconjugate vaccine produced using protein glycan coupling technology is protective in an inhalational rat model of tularemia. J Immunol Res 2018, 8087916.

Matthies, D., et al., Cell-free expression and assembly of ATP synthase. J Mol Biol, 2011. 413(3): p. 593-603.

Maue, A.C., F. Poly, and P. Guerry, A capsule conjugate vaccine approach to prevent diarrheal disease caused by Campylobacter jejuni. Hum Vaccin Immunother, 2014. 10(6): p. 1499-504.

Mescher, M.F. and J.L. Strominger, Purification and characterization of a prokaryotic glucoprotein from the cell envelope of Halobacterium salinarium. J Biol Chem, 1976. 251(7): p. 2005-14.

Murphy, T.W., Sheng, J., Naler, L.B., Feng, X., and Lu, C. (2019). On-chip manufacturing of synthetic proteins for point-of-care therapeutics. Microsyst Nanoeng 5, 13.

Murray, G.L., S.R. Attridge, and R. Morona, Altering the length of the lipopolysaccharide O antigen has an impact on the interaction of Salmonella enterica serovar Typhimurium with macrophages and complement. J Bacteriol, 2006. 188 (7): p. 2735-9.

Murray, G.L., S.R. Attridge, and R. Morona, Regulation of Salmonella typhimurium lipopolysaccharide O antigen chain length is required for virulence; identification of FepE as a second Wzz. Mol Microbiol, 2003. 47(5): p. 1395-406.

Needham, B.D., et al., Modulating the innate immune response by combinatorial engineering of endotoxin. Proc. Natl. Acad. Sci. U. S. A., 2013. 110(4): p. 1464-9.

Neuberger, A., Carbohydrates in protein: The carbohydrate component of crystalline egg albumin. Biochem J, 1938. 32 (9): p. 1435-51.

Ng, P. P., et al., A vaccine directed to B cells and produced by cell-free protein synthesis generates potent antilymphoma immunity. Proc Natl Acad Sci U S A, 2012. 109(36): p. 14526-31.

Nirenberg, M.W. and J.H. Matthaei, The dependence of cell-free protein synthesis in E. coli upon naturally occurring or synthetic polyribonucleotides. Proc Natl Acad Sci U S A, 1961. 47: p. 1588-602.

Nothaft, H., et al., Study of free oligosaccharides derived from the bacterial N-glycosylation pathway. Proc Natl Acad Sci U S A, 2009. 106(35): p. 15019-24.

Novak, R.T., Kambou, J.L., Diomande, F.V., Tarbangdo, T.F., Ouedraogo-Traore, R., Sangare, L., Lingani, C., Martin, S.W., Hatcher, C., Mayer, L.W., et al. (2012). Serogroup A meningococcal conjugate vaccination in Burkina Faso: analysis of national surveillance data. Lancet Infect Dis 12, 757-764.

Ohtsubo, K. and J.D. Marth, Glycosylation in cellular mechanisms of health and disease. Cell, 2006. 126(5): p. 855-67.

Olivier, N.B., et al., In vitro biosynthesis of UDP-N, N'-diacetylbacillosamine by enzymes of the Campylobacter jejuni general protein glycosylation system. Biochemistry, 2006. 45(45): p. 13659-69.

Oyston, P.C., A. Sjostedt, and R.W. Titball, Tularaemia: bioterrorism defence renews interest in Francisella tularensis. Nat Rev Microbiol, 2004. 2(12): p. 967-78.

Perez, C., et al., Structure and mechanism of an active lipid-linked oligosaccharide flippase. Nature, 2015. 524(7566): p. 433-8.

Perez, J.G., J.C. Stark, and M.C. Jewett, Cell-free synthetic biology: Engineering beyond the cell. Cold Spring Harb. Perspect. Biol., 2016.

Perez-Pinera, P., Han, N., Cleto, S., Cao, J., Purcell, O., Shah, K.A., Lee, K., Ram, R., and Lu, T.K. (2016). Synthetic biology and microbioreactor platforms for programmable production of biologics at the point-of-care. Nat Commun 7, 12211.

Petsch, D. and F.B. Anspach, Endotoxin removal from protein solutions. J. Biotechnol., 2000. 76(2-3): p. 97-119.

Pinho, S.S. and C.A. Reis, Glycosylation in cancer: mechanisms and clinical implications. Nat Rev Cancer, 2015. 15 (9): p. 540-55.

Poehling, K.A., Talbot, T.R., Griffin, M.R., Craig, A.S., Whitney, C.G., Zell, E., Lexau, C.A., Thomas, A.R., Harrison, L. H., Reingold, A.L., et al. (2006). Invasive pneumococcal disease among infants before and after introduction of pneumococcal conjugate vaccine. JAMA 295, 1668-1674.

Prior, J.L., et al., Characterization of the O antigen gene cluster and structural analysis of the O antigen of Francisella tularensis subsp. tularensis. J Med Microbiol, 2003. 52(Pt 10): p. 845-51.

Qadri, F., Svennerholm, A.M., Faruque, A.S., and Sack, R.B. (2005). Enterotoxigenic *Escherichia coli* in developing countries: epidemiology, microbiology, clinical features, treatment, and prevention. Clin Microbiol Rev 18, 465-483.

Raetz, C.R., and Whitfield, C. (2002). Lipopolysaccharide endotoxins. Annu Rev Biochem 71, 635-700.

(56) References Cited

OTHER PUBLICATIONS

Ravenscroft, N., et al., Purification and characterization of a Shigella conjugate vaccine, produced by glycoengineering *Escherichia coli*. Glycobiology, 2015.
Riddle, M.S., Kaminski, R.W., Di Paolo, C., Porter, C.K., Gutierrez, R.L., Clarkson, K.A., Weerts, H.E., Duplessis, C., Castellano, A., Alaimo, C., et al. (2016). Safety and immunogenicity of a candidate bioconjugate vaccine against Shigella flexneri 2a administered to healthy adults: a single blind, randomized phase I study. Clin Vaccine Immunol.
Rietschel, E.T., et al., Bacterial endotoxin: molecular relationships of structure to activity and function. FASEB J., 1994. 8(2): p. 217-25.
Roush, S.W., McIntyre, L., and Baldy, L.M. (2008). Manual for the surveillance of vaccine-preventable diseases. Atlanta: Centers for Disease Control and Prevention, 4.
Russell, J.A., Management of sepsis. N. Engl. J. Med., 2006. 355(16): p. 1699-1713.
Saldias, M.S., X. Ortega, and M.A. Valvano, Burkholderia cenocepacia O antigen lipopolysaccharide prevents phagocytosis by macrophages and adhesion to epithelial cells. J Med Microbiol, 2009. 58(Pt 12): p. 1542-8.
Salehi, A.S., et al., *Escherichia coli*-based cell-free extract development for protein-based cancer therapeutic production. Int J Dev Biol, 2016. 60(7-8-9): p. 237-243.
Sleytr, U.B., Heterologous reattachment of regular arrays of glycoproteins on bacterial surfaces. Nature, 1975. 257 (5525): p. 400-2.
Spiro, R.G., Protein glycosylation: nature, distribution, enzymatic formation, and disease implications of glycopeptide bonds. Glycobiology, 2002. 12(4): p. 43R-56R.
Stech, M., et al., A continuous-exchange cell-free protein synthesis system based on extracts from cultured insect cells. PLoS One, 2014. 9(5): p. e96635.
Stech, M., et al., Cell-free systems: functional modules for synthetic and chemical biology. Adv Biochem Eng Biotechnol, 2013. 137: p. 67-102.
Stefan, A., Conti, M., Rubboli, D., Ravagli, L., Presta, E., and Hochkoeppler, A. (2011). Overexpression and purification of the recombinant diphtheria toxin variant CRM197 in Escherichia coli. J Biotechnol 156, 245-252.
Stefanetti, G., et al., Glycoconjugate vaccine using a genetically modified O antigen induces protective antibodies to Francisella tularensis. Proc. Natl. Acad. Sci. U. S. A., 2019. 116(14): p. 7062-7070.
Szymanski, C.M., et al., Evidence for a system of general protein glycosylation in Campylobacter jejuni. Mol Microbiol, 1999. 32(5): p. 1022-30.
Thanka Christlet, T.H. and K. Veluraja, Database analysis of O-glycosylation sites in proteins. Biophys J, 2001. 80(2): p. 952-60.
The Review on Antimicrobial Resistance, C.b.J.O.N. (2014). Antimicrobial Resistance: Tackling a crisis for the health and wealth of nations.
Theodoratou, E., et al., The role of glycosylation in IBD. Nat Rev Gastroenterol Hepatol, 2014. 11(10): p. 588-600.
Trotter, C.L., McVernon, J., Ramsay, M.E., Whitney, C.G., Mulholland, E.K., Goldblatt, D., Hombach, J., and Kieny, M. P. (2008). Optimising the use of conjugate vaccines to prevent disease caused by Haemophilus influenzae type b, Neisseria meningitidis and Streptococcus pneumoniae. Vaccine 26, 4434-4445.
Valvano, M.A., and Crosa, J.H. (1989). Molecular cloning and expression in *Escherichia coli* K-12 of chromosomal genes determining the 07 lipopolysaccharide antigen of a human invasive strain of *E. coli* 07:K1. Infect Immun 57, 937-943.
Varki, A., Biological roles of oligosaccharides: all of the theories are correct. Glycobiology, 1993. 3(2): p. 97-130.
Wacker, M., et al., Prevention of Staphylococcus aureus infections by glycoprotein vaccines synthesized in *Escherichia coli*. J Infect Dis, 2014. 209(10): p. 1551-61.

Wahl, B., O'Brien, K.L., Greenbaum, A., Majumder, A., Liu, L., Chu, Y., Luksic, I., Nair, H., McAllister, D.A., Campbell, H., et al. (2018). Burden of Streptococcus pneumoniae and Haemophilus influenzae type b disease in children in the era of conjugate vaccines: global, regional, and national estimates for 2000-15. Lancet Glob Health 6, e744-e757.
Walt, D., et al., Transforming Glycoscience: A Roadmap for the Future. 2012: The National Academies Press.
Wang, J.Z., I. Grundke-Iqbal, and K. Iqbal, Glycosylation of microtubule-associated protein tau: an abnormal posttranslational modification in Alzheimer's disease. Nat Med, 1996. 2(8): p. 871-5.
Wang, L.X. and B.G. Davis, Realizing the Promise of Chemical Glycobiology. Chem Sci, 2013. 4(9): p. 3381-3394.
Wang, X., et al., Peptide surfactants for cell-free production of functional G protein-coupled receptors. Proc Natl Acad Sci U S A, 2011. 108(22): p. 9049-54.
Weintraub, A. (2003). Immunology of bacterial polysaccharide antigens. Carbohydr Res 338, 2539-2547.
Wetter, M., Kowarik, M., Steffen, M., Carranza, P., Corradin, G., and Wacker, M. (2013). Engineering, conjugation, and immunogenicity assessment of *Escherichia coli* 0121 O antigen for its potential use as a typhoid vaccine component. Glycoconj J 30, 511-522.
WHO (2014). Temperature Sensitivity of Vaccines.
Wilson, I.B., Y. Gavel, and G. von Heijne, Amino acid distributions around O-linked glycosylation sites. Biochem J, 1991. 275 ( Pt 2): p. 529-34.
Xu, Y., et al. Production of bispecific antibodies in "Knobs-into-Holes" using a cell-free expression system. in mAbs. 2014. Taylor & Francis.
Young, N.M., et al., Structure of the N-linked glycan present on multiple glycoproteins in the Gram-negative bacterium, Campylobacter jejuni. Journal of Biological Chemistry, 2002. 277(45): p. 42530-9.
Zalkin, H., C. Yanofsky, and C.L. Squires, Regulated in vitro synthesis of *Escherichia coli* tryptophan operon messenger ribonucleic acid and enzymes. J Biol Chem, 1974. 249(2): p. 465-75.
Zawada, J.F., et al., Microscale to manufacturing scale-up of cell-free cytokine production—a new approach for shortening protein production development timelines. Biotechnol Bioeng, 2011. 108(7): p. 1570-8.
Zimmerman, E.S., et al., Production of Site-Specific Antibody-Drug Conjugates Using Optimized Non-Natural Amino Acids in a Cell-Free Expression System. Bioconjugate Chemistry, 2014. 25(2): p. 351-361.
Forsgren et al., Protein D of Haemophilus influenzae: A Protective Nontypeable H. influenzae Antigen and a Carrier for Pneumococcal Conjugate Vaccines, Clinical Infectious Diseases, vol. 46, No. 5,Mar. 1, 2008 (Mar. 1, 2008), pp. 726-731.
International Search Report, corresponding to PCT/US2020/013207, Apr. 30, 2020, 2 ppgs.
Office Action, corresponding to JP 2021-540255, dated Dec. 12, 2023.
Schwarz, F., et al., Relaxed acceptor site specificity of bacterial oligosaccharyltransferase in vivo. Glycobiology, 2011. 21(1): p. 45-54.
Abu-Qarn, M., J. Eichler, and N. Sharon, Not just for Eukarya anymore: protein glycosylation in Bacteria and Archaea. Curr Opin Struct Biol, 2008. 18(5): p. 544-50.
Adiga, R., Al-adhami, M., Andar, A., Borhani, S., Brown, S., Burgenson, D., Cooper, M.A., Deldari, S., Frey, D.D., Ge, X., et al. (2018). Point-of-care production of therapeutic proteins of good-manufacturing-practice quality. Nat Biomed Eng.
Albrecht, S., et al., Glycosylation as a marker for inflammatory arthritis. Cancer Biomark, 2014. 14(1): p. 17-28.
Anderson, P., Antibody responses to Haemophilus influenzae type b and diphtheria toxin induced by conjugates of oligosaccharides of the type b capsule with the nontoxic protein CRM197. Infect Immun, 1983. 39(1): p. 233-8.
Ashok, A., Brison, M., and LeTallec, Y. (2017). Improving cold chain systems: Challenges and solutions. Vaccine 35, 2217-2223.
Axford, U.S., Glycosylation and rheumatic disease. Biochim Biophys Acta, 1999. 1455(2-3): p. 219-29.

(56) References Cited

OTHER PUBLICATIONS

Bacon, D.J., et al., A phase-variable capsule is involved in virulence of Campylobacter jejuni 81-176. Mol Microbiol, 2001. 40(3): p. 769-77.
Baudoin, L. and T. Issad, O-GlcNAcylation and Inflammation: A Vast Territory to Explore. Front Endocrinol (Lausanne), 2014. 5: p. 235.
Bayburt, T.H., and Sligar, S.G. (2010). Membrane protein assembly into Nanodiscs. FEBS Lett 584, 1721-1727.
Bernhard, F. and Y. Tozawa, Cell-free expression—making a mark. Curr Opin Struct Biol, 2013. 23(3): p. 374-80.
Bhushan, R., Anthony, B.F., and Frasch, C.E. (1998). Estimation of group B streptococcus type III polysaccharide-specific antibody concentrations in human sera is antigen dependent. Infect Immun 66, 5848-5853.
Bogaert, D., Hermans, P.W., Adrian, P.V., Rumke, H.C., and de Groot, R. (2004). Pneumococcal vaccines: an update on current strategies. Vaccine 22, 2209-2220.
Boles, K.S., Kannan, K., Gill, J., Felderman, M., Gouvis, H., Hubby, B., Kamrud, K.I., Venter, J.C., and Gibson, D.G. (2017). Digital-to-biological converter for on-demand production of biologics. Nat Biotechnol 35, 672-675.
Brito, L.A., and Singh, M. (2011). Acceptable levels of endotoxin in vaccine formulations during preclinical research. J Pharm Sci 100, 34-37.
Brodel, A.K., D.A. Wustenhagen, and S. Kubick, Cell-free protein synthesis systems derived from cultured Mammalian cells. Methods Mol Biol, 2015. 1261: p. 129-40.
Bundy, B.C., M.J. Franciszkowicz, and J.R. Swartz, Escherichia coli-based cell-free synthesis of virus-like particles. Biotechnol Bioeng, 2008. 100(1): p. 28-37.
Calhoun, K.A. and J.R. Swartz, An economical method for cell-free protein synthesis using glucose and nucleoside monophosphates. Biotechnol Prog, 2005. 21(4): p. 1146-53.
Calhoun, K.A. and J.R. Swartz, Energizing cell-free protein synthesis with glucose metabolism. Biotechnol Bioeng, 2005. 90(5): p. 606-13.
Caschera, F. and V. Noireaux, Synthesis of 2.3 mg/ml of protein with an all Escherichia coli cell-free transcription-translation system. Biochimie, 2014. 99: p. 162-8.
Casella, C.R., and Mitchell, T.C. (2008). Putting endotoxin to work for US: monophosphoryl lipid A as a safe and effective vaccine adjuvant. Cell Mol Life Sci 65, 3231-3240.
CDC (2019). CDC Vaccine Price List.
Celik, E., Ollis, A.A., Lasanajak, Y., Fisher, A.C., Gur, G., Smith, D.F., and DeLisa, M.P. (2015). Glycoarrays with engineered phages displaying structurally diverse oligosaccharides enable high-throughput detection of glycan-protein interactions. Biotechnol J 10, 199-209.
Chambers, D.A. and G. Zubay, The stimulatory effect of cyclic adenosine 3'5'-monophosphate on DNA-directed synthesis of beta-galactosidase in a cell-free system. Proc Natl Acad Sci U S A, 1969. 63(1): p. 118-22.
Chauhan, U.S., A. Rao, and G.P. Raghava, In silico platform for prediction of N-, O- and C-glycosites in eukaryotic protein sequences. PLoS One, 2013. 8(6): p. e67008.
Chen, D.J., Osterrieder, N., Metzger, S.M., Buckles, E., Doody, A.M., DeLisa, M.P., and Putnam, D. (2010). Delivery of foreign antigens by engineered outer membrane vesicle vaccines. Proc Natl Acad Sci U S A 107, 3099-3104.
Chen, M.M., K.J. Glover, and B. Imperiali, From peptide to protein: comparative analysis of the substrate specificity of N-linked glycosylation in C. jejuni. Biochemistry, 2007. 46(18): p. 5579-85.
Chong, S., Overview of cell-free protein synthesis: historic landmarks, commercial systems, and expanding applications. Curr Protoc Mol Biol, 2014. 108: p. 16 30 1-11.
Crowell, L.E., Lu, A.E., Love, K.R., Stockdale, A., Timmick, S.M., Wu, D., Wang, Y.A., Doherty, W., Bonnyman, A., Vecchiarello, N., et al. (2018). On-demand manufacturing of clinical-quality biopharmaceuticals. Nat Biotechnol.

Cuccui, J., et al., Exploitation of bacterial N-linked glycosylation to develop a novel recombinant glycoconjugate vaccine against Francisella tularensis. Open Biol, 2013. 3(5): p. 130002.
Daniels, M.A., K.A. Hogquist, and S.C. Jameson, Sweet 'n' sour: the impact of differential glycosylation on T cell responses. Nat Immunol, 2002. 3(10): p. 903-10.
Dennis, D.T., et al., Tularemia as a biological weapon: medical and public health management. Jama, 2001. 285(21): p. 2763-73.
Dube, D.H. and A.R. Bertozzi, Glycans in cancer and inflammation—potential for therapeutics and diagnostics. Nat Rev Drug Discov, 2005. 4: p. 477-88.
Dudley, Q.M., A.S. Karim, and M.C. Jewett, Cell-free metabolic engineering: Biomanufacturing beyond the cell. Biotechnology Journal, 2015. 10(1): p. 69-82.
Duerr, C.U., et al., O-antigen delays lipopolysaccharide recognition and impairs antibacterial host defense in murine intestinal epithelial cells. PLoS Pathog, 2009. 5(9): p. e1000567.
Fernandez, S., Palmer, D.R., Simmons, M., Sun, P., Bisbing, J., McClain, S., Mani, S., Burgess, T., Gunther, V., and Sun, W. (2007). Potential role for Toll-like receptor 4 in mediating Escherichia coli maltose-binding protein activation of dendritic cells. Infect Immun 75, 1359-1363.
Figueiredo, D., Turcotte, C., Frankel, G., Li, Y., Dolly, O., Wilkin, G., Marriott, D., Fairweather, N., and Dougan, G. (1995). Characterization of recombinant tetanus toxin derivatives suitable for vaccine development. Infect Immun 63, 3218-3221.
Fisher, A.C., et al., Production of secretory and extracellular N-linked glycoproteins in Escherichia coli. Appl Environ Microbiol, 2011. 77(3): p. 871-81.
Frasch, C.E. (2009). Preparation of bacterial polysaccharide-protein conjugates: analytical and manufacturing challenges. Vaccine 27, 6468-6470.
Fulop, M., et al., Role of antibody to lipopolysaccharide in protection against low- and high-virulence strains of Francisella tularensis. Vaccine, 2001. 19(31): p. 4465-72.
Garcia-Quintanilla, F., et al., Production of a recombinant vaccine candidate against Burkholderia pseudomallei exploiting the bacterial N-glycosylation machinery. Front Microbiol, 2014. 5: p. 381.
Gavel, Y. and G. von Heijne, Sequence differences between glycosylated and non-glycosylated Asn-X-Thr/Ser acceptor sites: implications for protein engineering. Protein Eng, 1990. 3(5): p. 433-42.
Glover, K.J., E. Weerapana, and B. Imperiali, In vitro assembly of the undecaprenylpyrophosphate-linked heptasaccharide for prokaryotic N-linked glycosylation. Proc Natl Acad Sci U S A, 2005. 102(40): p. 14255-9.
Glover, K.J., et al., Direct biochemical evidence for the utilization of UDP-bacillosamine by PglC, an essential glycosyl-1-phosphate transferase in the Campylobacter jejuni N-linked glycosylation pathway. Biochemistry, 2006. 45 (16): p. 5343-50.
Guerry, P., et al., Campylobacter polysaccharide capsules: virulence and vaccines. Front Cell Infect Microbiol, 2012. 2: p. 7.
Haghi, F., Peerayeh, S.N., Siadat, S.D., and Montajabiniat, M. (2011). Cloning, expression and purification of outer membrane protein PorA of Neisseria meningitidis serogroup B. J Infect Dev Ctries 5, 856-862.
Hatz, C.F., Bally, B., Rohrer, S., Steffen, R., Kramme, S., Siegrist, C.A., Wacker, M., Alaimo, C., and Fonck, V.G. (2015). Safety and immunogenicity of a candidate bioconjugate vaccine against Shigella dysenteriae type 1 administered to healthy adults: A single blind, partially randomized Phase I study. Vaccine 33, 4594-4601.
Hodgman, C.E. and M.C. Jewett, Cell-free synthetic biology: thinking outside the cell. Metab Eng, 2012. 14(3): p. 261-9.
Hong, S.H., Ntai, I., Haimovich, A.D., Kelleher, N.L., Isaacs, F.J., and Jewett, M.C. (2014). Cell-free protein synthesis from a release factor 1 deficient Escherichia coli activates efficient and multiple site-specific nonstandard amino acid incorporation. ACS Synth Biol 3, 398-409.
Humphreys, G. (2011). Vaccination: rattling the supply chain (Bulletin of the World Health Organization: World Health Organization).
Huttner, A., Hatz, C., van den Dobbelsteen, G., Abbanat, D., Hornacek, A., Frolich, R., Dreyer, A.M., Martin, P., Davies, T., Fae, K., et al. (2017). Safety, immunogenicity, and preliminary clinical efficacy of a vaccine against extraintestinal pathogenic Escherichia

(56) References Cited

OTHER PUBLICATIONS

*coli* in women with a history of recurrent urinary tract infection: a randomised, single-blind, placebo-controlled phase 1b trial. Lancet Infect Dis.

* cited by examiner

CELL-FREE GLYCOPROTEIN SYNTHESIS (CFGPS) IN PROKARYOTIC CELL LYSATES ENRICHED WITH COMPONENTS FOR GLYCOSYLATION

CROSS-REFERENCE TO RELATED PATENT APPLICATIONS

The present application is a divisional of U.S. Ser. No. 16/023,134, filed Jun. 29, 2018, which is a continuation-in-part of International Application PCT/2016/069512, filed Dec. 30, 2016, which claims the benefit of priority under 35 U.S.C. § 119(e) to U.S. Provisional Patent Application 62/273,124, filed Dec. 30, 2015, the content of each are incorporated herein by reference in their entireties.

STATEMENT REGARDING FEDERALLY SPONSORED RESEARCH OR DEVELOPMENT

This invention was made with government support under grant number MCB 1413563 awarded by the National Science Foundation. The government has certain rights in the invention.

REFERENCE TO AN ELECTRONIC SEQUENCE LISTING

The contents of the electronic sequence listing (702581.02142_Sequence listing.xml; Size: 19,848 bytes; and Date of Creation: Dec. 23, 2022) is herein incorporated by reference in its entirety.

BACKGROUND

The present invention generally relates to components and systems for cell-free protein synthesis. In particular, the present invention relates to components and systems for cell-free glycoprotein synthesis (CFGpS) that involve prokaryotic cell lysates from engineered prokaryotic cell strains.

Glycosylation, or the attachment of glycans (sugars) to proteins, is the most abundant post-translational modification in nature and plays a pivotal role in protein folding, sorting, and activity. In molecular medicine, the compositions and patterns of glycans on recombinant therapeutic glycoproteins are known to impact pharmacokinetics and drug activity. The inability to precisely control protein glycosylation with current technologies represents a key challenge in the fields of glycoprotein synthesis and glycoprotein therapeutics.

Here, the inventors describe a CFGpS platform system with the potential to enable controllable glycosylation of therapeutic proteins in which i) all the biosynthetic machinery for protein synthesis and glycosylation is supplied by one or more E. coli lysate(s) and ii) transcription, translation, and glycosylation may be performed in an all-in-one in vitro reaction. The inventors have engineered glycosylation chassis strains that are optimized for glycosylation and produce up to 1-1.5 g/L protein in cell-free protein synthesis, which represents a 50% increase in potential glycoprotein yields compared to the state-of-the-art. This technology is a valuable addition to the CFPS and glycoengineering communities and complements previously developed in vivo glycosylation activity assays.

SUMMARY

Disclosed are non-naturally occurring strains of E. coli and methods of using lysates from the non-naturally occurring strains of E. coli in methods for cell-free glycoprotein synthesis (CFGpS). The disclosed non-naturally occurring strains of E. coli may be utilized as chassis strains for producing lysates that may be used for producing glycosylated proteins in vitro in cell-free glycosylated protein systems (CFGps). Lysates from the disclosed E. coli glycosylation chassis strains produce >50% higher yields of proteins in vitro compared to lysates from existing glycosylation chassis strains.

The non-naturally occurring strains of E. coli strains disclosed herein may be modified to overexpress glycosyltransferases and/or oligosaccharyltransferases. As such, the disclosed strains may be utilized to produce a lysate for in vitro protein synthesis that is enriched in glycosylation components relative to a strain that has not been thusly modified. Glycosylation components that are enriched in lysates produced from the modified strains may include, but are not limited to lipid-linked oligosaccharides (LLOs), oligosaccharyltransferases (OSTs), or both LLOs and OSTs. Novel lysates may be prepared by mixing and matching different lysates from the disclosed strains that comprise different LLOs, OSTs, and other components in cell-free cocktails to enable glycoprotein synthesis. Other components of CFGpS reactions may include plasmids encoding target proteins for glycoprotein synthesis.

Individual crude lysates and mixtures of crude lysates of the disclosed strains are shown herein to carry out one-pot glycoprotein synthesis in CFGpS reactions, demonstrating that glycosylation components are present in the crude lysates and participate in N-linked glycosylation. The in vitro activity of four OST homologs with natural sequence variation compared to the archetypal C. jejuni OST were characterized and compared using CFGpS. The disclosed CFGpS technology is modular, flexible, and has promising applications as a high-throughput prototyping platform for glycoproteins of biotechnological interest.

The disclosed CFGpS system has a number of advantages and applications, including but not limited to: (i) being the first prokaryotic cell-free system capable of one-pot, cell-free transcription, translation, and glycosylation of proteins, (ii) on demand expression of glycoprotein therapeutics with potentially controllable glycosylation; (iii) discovery methods for novel glycosyltransferases and oligosaccharyltransferases; (iv) prototyping of novel synthetic glycosylation pathways; (v) production of glycoprotein libraries for screening or functional genomics; and (vi) improved methods for production of glycoproteins for crystallography studies. The disclosed system also is modular in that different lysates from different modified strains may be combined to provide engineered lysate mixtures for rapid production of user-specified glycoproteins in CFGpS reactions.

DETAILED DESCRIPTION

Figure 1:
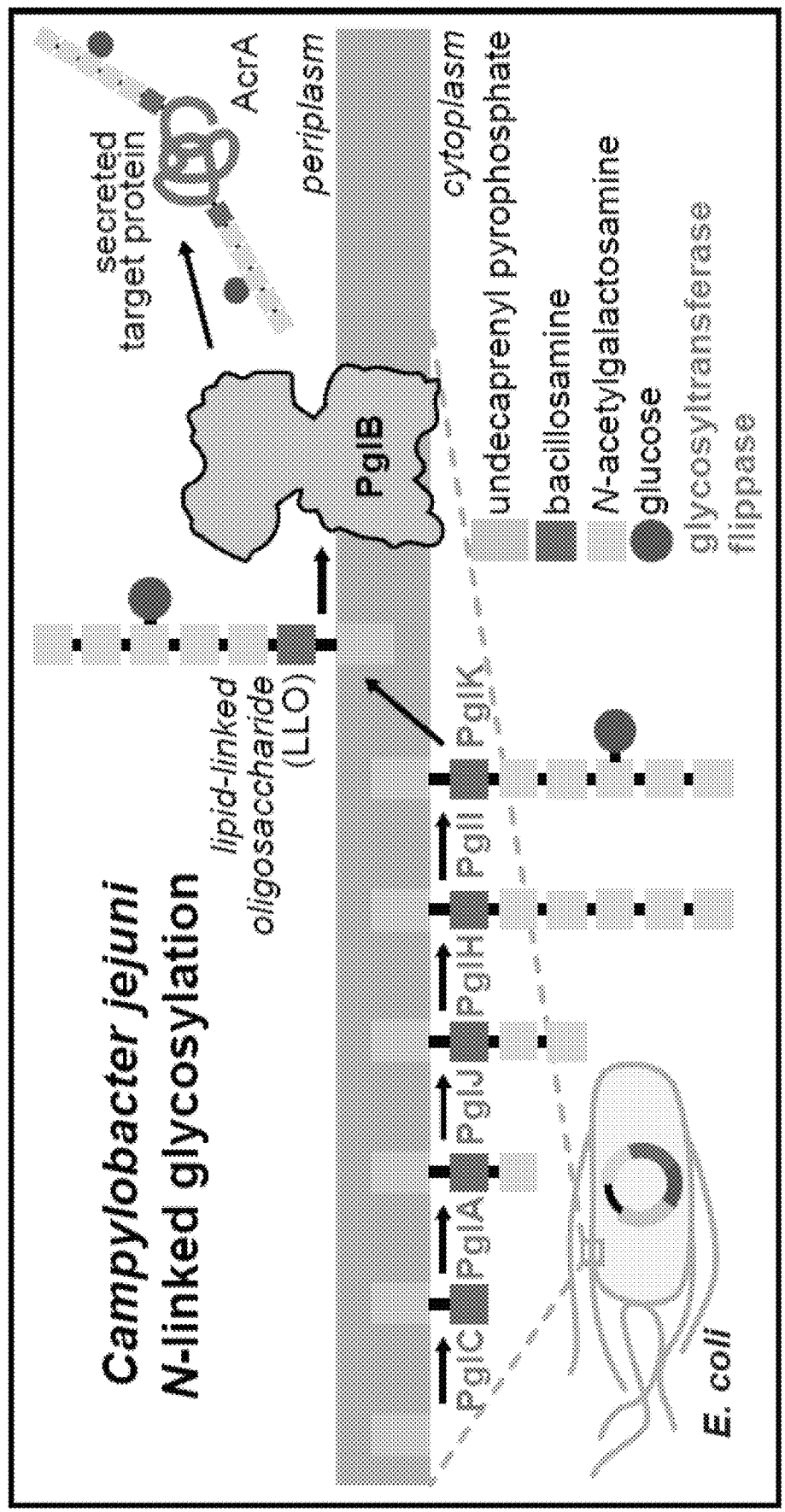
FIG. 1. Schematic depicting function of C. jejuni N-linked glycosylation pathway expressed in E. coli (adapted from Guarino & DeLisa, 2012).

Disclosed are cell-free glycoprotein synthesis (CFGpS) systems with the potential to enable controllable glycosylation of therapeutic proteins in which i) all the biosynthetic components for protein synthesis and glycosylation are supplied by an E. coli lysate and ii) transcription, translation, and glycosylation occur in an all-in-one in vitro reaction (e.g., a single reaction vessel). The E. coli lysate used in the disclosed systems may be prepared from engineered glycosylation chassis strains that are optimized for glycosylation and produce up to 1-1.5 g/L protein in cell-free protein synthesis, which represents a >50% increase in potential glycoprotein yields compared to the state-of-the-art cell-free protein synthesis systems.

The majority of glycoproteins for research and therapeutic applications are currently produced in systems that utilize eukaryotic cells. However, these eukaryotic cell systems are limited as compared to systems that utilize prokaryotic cells because: i) eukaryotic cells grow more slowly than prokaryotic cells, and as such, eukaryotic cell systems are relatively more time consuming than prokaryotic cell systems; and ii) the resulting glycosylation patterns in eukaryotic systems are not controllable because they utilize endogenous machinery to carry out the glycosylation process. The presently disclosed strains and cell-free systems for glycoprotein synthesis can be used to produce glycoproteins more quickly than existing strains and systems and provide for greater control over the glycosylation process compared to existing strains and systems.

The present inventors are unaware of any prokaryotic cell-free system with the capability to produce glycoproteins that involves overexpression of orthogonal glycosylation components. Commercial eukaryotic cell lysate systems for cell-free glycoprotein production exist, but these systems do not involve overexpression of orthogonal glycosylation components and do not enable user-specified glycosylation in contrast to the presently disclosed strains and cell-free systems for glycoprotein synthesis.

Definitions and Terminology

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a gene" or "an oligosaccharide" should be interpreted to mean "one or more genes" and "one or more oligosaccharides," respectively, unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the terms "bind," "binding," "interact," "interacting," "occupy" and "occupying" refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in Molecular Biology of the Cell, 3d edition, Garland Publishing, 1994. Steric interactions are generally understood to include those where the structure of the compound is such that it is capable of occupying a site by virtue of its three dimensional structure, as opposed to any attractive forces between the compound and the site.

Polynucleotides and Synthesis Methods

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and refer to a region or sequence of a nucleic acid which is to be amplified, sequenced, or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, Biochemistry, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

In certain exemplary embodiments, vectors such as, for example, expression vectors, containing a nucleic acid encoding one or more rRNAs or reporter polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif (1990).

Oligonucleotides and polynucleotides may optionally include one or more nonstandard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

As utilized herein, a "deletion" means the removal of one or more nucleotides relative to the native polynucleotide sequence. The engineered strains that are disclosed herein may include a deletion in one or more genes (e.g., a deletion in gmd and/or a deletion in waaL). Preferably, a deletion results in a non-functional gene product. As utilized herein, an "insertion" means the addition of one or more nucleotides to the native polynucleotide sequence. The engineered strains that are disclosed herein may include an insertion in one or more genes (e.g., an insertion in gmd and/or an insertion in waaL). Preferably, a deletion results in a non-functional gene product. As utilized herein, a "substitution" means replacement of a nucleotide of a native polynucleotide sequence with a nucleotide that is not native to the polynucleotide sequence. The engineered strains that are disclosed herein may include a substitution in one or more genes (e.g., a substitution in gmd and/or a substitution in waaL). Preferably, a substitution results in a non-functional gene product, for example, where the substitution introduces a premature stop codon (e.g., TAA, TAG, or TGA) in the coding sequence of the gene product. In some embodiments, the engineered strains that are disclosed herein may include two or more substitutions where the substitutions introduce multiple premature stop codons (e.g., TAATAA, TAGTAG, or TGATGA).

In some embodiments, the engineered strains disclosed herein may be engineered to include and express one or heterologous genes. As would be understood in the art, a heterologous gene is a gene that is not naturally present in the engineered strain as the strain occurs in nature. A gene that is heterologous to *E. coli* is a gene that does not occur in *E. coli* and may be a gene that occurs naturally in another microorganism (e.g. a gene from *C. jejuni*) or a gene that does not occur naturally in any other known microorganism (i.e., an artificial gene).

Peptides, Polypeptides, Proteins, and Synthesis Methods

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard or unnatural amino acids. The term "amino acid residue" may include alpha-, beta-, gamma-, and delta-amino acids.

In some embodiments, the term "amino acid residue" may include nonstandard or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard or unnatural amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 23ufa23hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length>100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

As used herein, "translation template" refers to an RNA product of transcription from an expression template that can be used by ribosomes to synthesize polypeptides or proteins.

The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

The steps of the methods described herein can be performed in any suitable order unless otherwise indicated herein or otherwise clearly contradicted by context. The steps may be repeated or reiterated any number of times to achieve a desired goal unless otherwise indicated herein or otherwise clearly contradicted by context.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Cell-Free Protein Synthesis (CFPS)

The strains and systems disclosed herein may be applied to cell-free protein synthesis methods as known in the art. See, for example, U.S. Pat. Nos. 5,478,730; 5,556,769; 5,665,563; 6,168,931; 6,869,774; 6,994,986; 7,118,883; 7,189,528; 7,338,789; 7,387,884; 7,399,610; 8,703,471; and 8,999,668. See also U.S. Published Application Nos. 2015-0259757, 2014-0295492, 2014-0255987, 2014-0045267, 2012-0171720, 2008-0138857, 2007-0154983, 2005-0054044, and 2004-0209321. See also U.S Published Application Nos. 2005-0170452; 2006-0211085; 2006-0234345; 2006-0252672; 2006-0257399; 2006-0286637; 2007-

0026485; 2007-0178551; and 2018-0016612. See also Published PCT International Application Nos. 2003/056914; 2004/013151; 2004/035605; 2006/102652; 2006/119987; and 2007/120932. See also Jewett, M. C., Hong, S. H., Kwon, Y. C., Martin, R. W., and Des Soye, B. J. 2014, "Methods for improved in vitro protein synthesis with proteins containing non standard amino acids," U.S. Patent Application Ser. No. 62/044,221; Jewett, M. C., Hodgman, C. E., and Gan, R. 2013, "Methods for yeast cell-free protein synthesis," U.S. Patent Application Ser. No. 61/792,290; Jewett, M. C., J. A. Schoborg, and C. E. Hodgman. 2014, "Substrate Replenishment and Byproduct Removal Improve Yeast Cell-Free Protein Synthesis," U.S. Patent Application Ser. No. 61/953,275; and Jewett, M. C., Anderson, M. J., Stark, J. C., Hodgman, C. E. 2015, "Methods for activating natural energy metabolism for improved yeast cell-free protein synthesis," U.S. Patent Application Ser. No. 62/098, 578. See also Guarino, C., & DeLisa, M. P. (2012). A prokaryote-based cell-free translation system that efficiently synthesizes glycoproteins. Glycobiology, 22(5), 596-601. The contents of all of these references are incorporated in the present application by reference in their entireties.

In certain exemplary embodiments, one or more of the methods described herein are performed in a vessel, e.g., a single, vessel. The term "vessel," as used herein, refers to any container suitable for holding on or more of the reactants (e.g., for use in one or more transcription, translation, and/or glycosylation steps) described herein. Examples of vessels include, but are not limited to, a microtitre plate, a test tube, a microfuge tube, a beaker, a flask, a multi-well plate, a cuvette, a flow system, a microfiber, a microscope slide and the like.

In certain exemplary embodiments, physiologically compatible (but not necessarily natural) ions and buffers are utilized for transcription, translation, and/or glycosylation, e.g., potassium glutamate, ammonium chloride and the like. Physiological cytoplasmic salt conditions are well-known to those of skill in the art.

The strains and systems disclosed herein may be applied to cell-free protein methods in order to prepare glycosylated macromolecules (e.g., glycosylated peptides, glycosylated proteins, and glycosylated lipids). Glycosylated proteins that may be prepared using the disclosed strains and systems may include proteins having N-linked glycosylation (i.e., glycans attached to nitrogen of asparagine and/or arginine side-chains) and/or O-linked glycosylation (i.e., glycans attached to the hydroxyl oxygen of serine, threonine, tyrosine, hydroxylysine, and/or hydroxyproline). Glycosylated lipids may include O-linked glycans via an oxygen atom, such as ceramide.

The glycosylated macromolecules disclosed herein may include unbranched and/or branched sugar chains composed of monomers as known in the art such as glucose (e.g., β-D-glucose), galactose (e.g., β-D-galactose), mannose (e.g., β-D-mannose), fucose (e.g., α-L-fucose), N-acetyl-glucosamine (GlcNAc), N-acetyl-galactosamine (GalNAc), neuraminic acid, N-acetylneuraminic acid (i.e., sialic acid), and xylose, which may be attached to the glycosylated macromolecule, growing glycan chain, or donor molecule (e.g., a donor lipid and/or a donor nucleotide) via respective glycosyltransferases (e.g., oligosaccharyltransferases, GlcNAc transferases, GalNAc transferases, galactosyltransferases, and sialyltransferases). The glycosylated macromolecules disclosed herein may include glycans as known in the art including but not limited to $Man_3GlcNAc_2$ glycan, $Man_5GlcNAc_3$ glycan, and the fully sialylated human glycan $Man_3GlcNAc_4Gal_2Neu_5Ac_2$. As such, the disclosed engineered strains may be enriched in glycans and/or lipid-linked oligosaccharides (LLOs) such as, but not limited to, $Man_3GlcNAc_2$ glycan, $Man_5GlcNAc_3$ glycan, and/or $Man_3GlcNAc_4Gal_2Neu_5Ac_2$ glycan, and the engineered strains may be utilized to prepare lysates that are enriched in glycans and/or lipid-linked oligosaccharides (LLOs) such as, but not limited to, $Man_3GlcNAc_2$ glycan, $Man_5GlcNAc_3$ glycan, and/or $Man_3GlcNAc_4Gal_2Neu_5Ac_2$ glycan.

The disclosed cell-free protein synthesis systems may utilize components that are crude and/or that are at least partially isolated and/or purified. As used herein, the term "crude" may mean components obtained by disrupting and lysing cells and, at best, minimally purifying the crude components from the disrupted and lysed cells, for example by centrifuging the disrupted and lysed cells and collecting the crude components from the supernatant and/or pellet after centrifugation. The term "isolated or purified" refers to components that are removed from their natural environment, and are at least 60% free, preferably at least 75% free, and more preferably at least 90% free, even more preferably at least 95% free from other components with which they are naturally associated.

Cell-Free Glycoprotein Synthesis (CFGpS) in Prokaryotic Cell Lysates Enriched with Components for Glycosylation Disclosed are compositions and methods for performing cell-free glycoprotein synthesis (CFGpS). In some embodiments, the composition and methods include or utilize prokaryotic cell lysates enriched with components for glycosylation and prepared from genetically modified strains of prokaryotes. Compositions and methods for performing cell-free glycoprotein synthesis (CFGpS) and for in vitro synthesis of bioconjugates and uses thereof (e.g., as vaccines) via recombinant production of N-glycosylated proteins in prokaryotic lysates are known in the art. (See, e.g., U.S. Published Application No. 2018-0016612, the content of which is incorporated herein by reference in its entirety). Disclosed herein are improved compositions and methods for performing cell-free glycoprotein synthesis (CFGpS).

In some embodiments, the genetically modified prokaryote is a genetically modified strain of *Escherichia coli* or any other prokaryote suitable for preparing a lysate for CFGpS. Optionally, the modified strain of *Escherichia coli* is derived from rEc.C321. Preferably, the modified strain includes genomic modifications (e.g., deletions of genes rendering the genes inoperable) that preferably result in lysates capable of high-yielding cell-free protein synthesis. Also, preferably, the modified strain includes genomic modification (e.g., deletions of genes rendering the genes inoperable) that preferably result in lysates comprising sugar precursors for glycosylation at relatively high concentrations (e.g., in comparison to a strain not having the genomic modification). In some embodiments, a lysate prepared from the modified strain comprises sugar precursors at a concentration that is at least 20%, 30%, 40%, 50%, 60%, 70%, 80%, 90%, 100%, 150%, 200%, or higher than a lysate prepared from a strain that is not modified.

In some embodiments, the modified strain includes a modification that results in an increase in the concentration of a monosaccharide utilized in glycosylation (e.g., glucose, mannose, N-acetyl-glucosamine (GlcNAc), N-acetyl-galactosamine (GalNAc), galactose, sialic acid, neuraminic acid, fucose). As such, the modification may inactivate an enzyme that metabolizes a monosaccharide or polysaccharide utilized in glycosylation. In some embodiments, the modification inactivates a dehydratase or carbon-oxygen lyase enzyme (EC 4.2) (e.g., via a deletion of at least a portion of the gene encoding the enzyme). In particular, the modification may inactivate a GDP-mannose 4,6-dehydratase (EC 4.2.1.47). When the modified strain is *E. coli*, the modification may include an inactivating modification in the gmd gene (e.g., via a deletion of at least a portion of the gmd gene). The sequence of the *E. coli* gmd gene is provided herein as SEQ ID NO:1 and the amino acid sequence of *E. coli* GDP-mannose 4,6-dehydratase is provided as SEQ ID NO:2.

In some embodiments, the modified strain includes a modification that inactivates an enzyme that is utilized in the glycosyltransferase pathway. In some embodiments, the modification inactivates an oligosaccharide ligase enzyme (e.g., via a deletion of at least a portion of the gene encoding the enzyme). In particular, the modification may inactivate an O-antigen ligase that optionally conjugates an O-antigen to a lipid A core oligosaccharide. The modification may include an inactivating modification in the waaL gene (e.g., via a deletion of at least a portion of the waaL gene). The sequence of the *E. coli* waaL gene is provided herein as SEQ ID NO:3 and the amino acid sequence of *E. coli* O-antigen ligase is provided as SEQ ID NO:4.

In some embodiments, the modified strain includes a modification that inactivates a dehydratase or carbon-oxygen lyase enzyme (e.g., via a deletion of at least a portion of the gene encoding the enzyme) and also the modified strain includes a modification that inactivates an oligosaccharide ligase enzyme (e.g., via a deletion of at least a portion of the gene encoding the enzyme). The modified strain may include an inactivation or deletion of both gmd and waaL.

In some embodiments, the modified strain may be modified to express one or more orthogonal or heterologous genes. In particular, the modified strain may be genetically modified to express an orthogonal or heterologous gene that is associated with glycoprotein synthesis such as a glycosyltransferase (GT) which is involved in the lipid-linked oligosaccharide (LLO) pathway. In some embodiments, the modified strain may be modified to express an orthogonal or heterologous oligosaccharyltransferase (EC 2.4.1.119) (OST). Oligosaccharyltransferases or OSTs are enzymes that transfer oligosaccharides from lipids to proteins.

In particular, the modified strain may be genetically modified to express an orthogonal or heterologous gene in a glycosylation system (e.g., an N-linked glycosylation system and/or an O-linked glycosylation system). The N-linked glycosylation system of *Campylobacter jejuni* has been transferred to *E. coli*. (See Wacker et al., "N-linked glycosylation in *Campylobacter jejuni* and its functional transfer into *E. coli*," *Science* 2002 Nov. 29; 298(5599):1790-3, the content of which is incorporated herein by reference in its entirety). In particular, the modified strain may be modified to express one or more genes of the pgl locus of *C. jejuni* or one or more genes of a homologous pgl locus. The genes of the pgl locus include pglG, pglF, pglE, wlaJ, pglD, pglC, pglA, pglB, pglJ, pglI, pglH, pglK, and gne, and are used to synthesize lipid-linked oligosaccharides (LLOs) and transfer the oligosaccharide moieties of the LLOs to a protein via an oligosaccharyltransferase.

Suitable orthogonal or heterologous oligosaccharyltransferases (OST) which may be expressed in the genetically modified strains may include *Campylobacter jejuni* oligosaccharyltransferase PglB. The gene for the *C. jejuni* OST is referred to as pglB, which sequence is provided as SEQ ID NO:11 and the amino acid sequence of *C. jejuni* PglB is provided as SEQ ID NO:12. PglB catalyzes transfer of an oligosaccharide to a D/E-Y-N-X-S/T motif (Y, X≠P) present on a protein.

Crude cell lysates may be prepared from the modified strains disclosed herein. The crude cell lysates may be prepared from different modified strains as disclosed herein and the crude cell lysates may be combined to prepare a mixed crude cell lysate. In some embodiments, one or more crude cell lysates may be prepared from one or more modified strains including a genomic modification (e.g., deletions of genes rendering the genes inoperable) that preferably result in lysates comprising sugar precursors for glycosylation at relatively high concentrations (e.g., in comparison to a strain not having the genomic modification). In some embodiments, one or more crude cell lysates may be prepared from one or more modified strains that have been modified to express one or more orthogonal or heterologous genes or gene clusters that are associated with glycoprotein synthesis. Preferably, the crude cell lysates or mixed crude cell lysates are enriched in glycosylation components, such as lipid-linked oligosaccharides (LLOs), glycosyltransferases (GTs), oligosaccharyltransferases (OSTs), or any combination thereof. More preferably, the crude cell lysates or mixed crude cell lysates are enriched in $Man_3GlcNAc_2$ LLOs representing the core eukaryotic glycan and/or $Man_3GlcNAc_4Gal_2Neu_5Ac_2$ LLOs representing the fully sialylated human glycan.

The disclosed crude cell lysates may be used in cell-free glycoprotein synthesis (CFGpS) systems to synthesize a variety of glycoproteins. The glycoproteins synthesized in the CFGpS systems may include prokaryotic glycoproteins and eukaryotic proteins, including human proteins. The CFGpS systems may be utilized in methods for synthesizing glycoproteins in vitro by performing the following steps using the crude cell lysates or mixtures of crude cell lysates disclosed herein: (a) performing cell-free transcription of a gene for a target glycoprotein; (b) performing cell-free translation; and (c) performing cell-free glycosylation. The methods may be performed in a single vessel or multiple vessels. Preferably, the steps of the synthesis method may be performed using a single reaction vessel. The disclosed methods may be used to synthesis a variety of glycoproteins, including prokaryotic glycoproteins and eukaryotic glycoproteins. The disclosed glycoproteins may be utilized in a variety of applications including vaccines and immunological compositions. The vaccines and immunological compositions including the disclosed glycoproteins may be lyophilized to extend their shelf life.

ILLUSTRATIVE EMBODIMENTS

The following embodiments are illustrative and should not be interpreted to limit the scope of the claimed subject matter.

Embodiment 1. A genetically modified strain of *Escherichia coli*, optionally derived from rEc.C321, with genomic modifications that preferably result in lysates capable of high-yielding cell-free protein synthesis and which preferably comprise sugar precursors for glycosylation at relatively high concentration.

Embodiment 2. The strains described in embodiment 1, in which the genomic modification is an inactivation or deletion of gmd.

Embodiment 3. The strains described in embodiment 1 or 2, in which the genomic modification is an inactivation or deletion of waaL.

Embodiment 4. The strains described in any of the foregoing embodiments, in which the genomic modification is an inactivation or deletion of both gmd and waaL Embodiment 5. A crude cell lysate prepared from one or more source strains of *E. coli* in which orthogonal or heterologous genes or gene clusters are expressed in the one or more source strains and the lysate optionally is enriched with glycosylation components (lipid-linked oligosaccharides (LLOs), glycosyltransferases (GTs), oligosaccharyltransferases (OSTs), or any combination of LLOs, GTs, and OSTs), and optionally the crude cell lysate is preserved by freeze-drying or lyophilization.

Embodiment 6. The crude cell lysate of embodiment 5, in which the one or more source strains overexpress an orthogonal or heterologous glycosyltransferase pathway from *C. jejuni*, resulting in the production of *C. jejuni* lipid-linked oligosaccharides (LLOs), and optionally the crude cell lysate is preserved by freeze-drying or lyophilization.

Embodiment 7. The crude cell lysate of embodiment 5 or 6, in which the one or more source strains overexpress a gene encoding an oligosaccharyltransferase (OST), and optionally the crude cell lysate is preserved by freeze-drying or lyophilization.

Embodiment 8. The crude cell lysate of any of embodiments 5-7, in which the one or more source strains overexpress a synthetic glycosyltransferase pathway, resulting in the production of a glycosylation intermediates, such as, but not limited to $Man_3GlcNAc_2$ and/or lipid-linked oligosaccharides (LLOs) comprising $Man_3GlcNAc_2$, and/or $Man_3GlcNAc_4Gal_2Neu_5Ac_2$ and/or lipid-linked oligosaccharides (LLOs) comprising $Man_3GlcNAc_4Gal_2Neu_5Ac_2$, and optionally the crude cell lysate is preserved by freeze-drying or lyophilization.

Embodiment 9. The crude cell lysate of any of embodiments 5-8, in which the one or more source strains overexpress a glycosyltransferase pathway and an OST, resulting in the production of LLOs and OST, and optionally the crude cell lysate is preserved by freeze-drying or lyophilization.

Embodiment 10. The crude cell lysate of any of embodiments 5-9, in which the one or more source strains overexpress a glycosyltransferase pathway from any organism, such as a heterologous glycosyltransferase pathway, resulting in the production of various lipid-linked oligosaccharides (LLOs) to enable synthesis of glycoproteins on demand of different glycan patterns, including human glycans, and optionally the crude cell lysate is preserved by freeze-drying or lyophilization.

Embodiment 11. The crude cell lysate of any of embodiments 5-10, in which the one or more source strains overexpress an OST from any organism, such as a heterologous OST, and optionally the crude cell lysate is preserved by freeze-drying or lyophilization.

Embodiment 12. An in vitro reaction composition comprising a mixture of crude cell lysates of any of embodiments 5-11 enriched with different glycosylation pathway components (e.g., LLOs, OSTs, and GTs), such as orthogonal or heterologous pathway components that synthesizes a biological macromolecule, and optionally the composition is preserved by freeze-drying or lyophilization.

Embodiment 13. The in vitro reaction composition of embodiment 12, in which the biological macromolecule synthesized in the in vitro reaction composition is a protein, and optionally the composition is preserved by freeze-drying or lyophilization.

Embodiment 14. The in vitro reaction composition of embodiment 12, in which the biological macromolecule synthesized in the in vitro reaction composition is a peptide, and optionally the composition is preserved by freeze-drying or lyophilization.

Embodiment 15. A method for cell-free production of glycosylated biological macromolecules, the method comprising producing the glycosylated biological macromolecules using a crude cell lysate, or mixtures of crude cell lysates, of any of embodiments 5-11 or the in vitro reaction composition of any of embodiments 12-14.

Embodiment 16. The method of embodiment 15, wherein the method comprises performing cell-free transcription, cell-free translation, and cell-free glycosylation in a single vessel comprising the crude cell lysate, or mixtures of crude cell lysates, of any of embodiments 5-11 or the in vitro reaction composition of any of embodiments 12-14.

Embodiment 17. The method of embodiment 16, in which the glycosylated biological macromolecule is a protein or peptide.

Embodiments 18. A method comprising: (a) preparing a set of N cell-free compositions comprising glycosylation machinery where N is 1-20 by (i) performing cell-free protein synthesis to obtain one or more of the N cell-free compositions or by (ii) overexpressing glycosylation pathway components in cells, lysing these cells, and preparing lysates to obtain one or more of the N cell-free compositions; (b) assembling components for a specific glycosylation reaction by combinatorially adding two or more of the N cell-free compositions to a cell-free protein synthesis reaction mixture comprising a cellular extract, a translation template encoding a glycosylated target protein, and cell-free glycoprotein synthesis reagents; and (c) expressing the translation template in the cell-free protein synthesis reaction mixture to prepare the glycosylated target protein.

Embodiments 19. A kit comprising as components: (a) a solution, the solution comprising one or more of: (i) a nucleoside triphosphate solution, (ii) a tRNA solution, (iii) a salt solution, (iv) an amino acid solution, (v) a cofactor solution, (vi) a protein helper factor solution, (vii) a glycosylation substrate solution, (viii) a glycosylation component solution, (ix) a glycosylation master mix, and mixtures thereof, and (b) a cell-free protein synthesis reaction mixture or mixtures, the cell-free protein synthesis reaction mixture(s) containing a cellular extract enriched with glycosylation components, optionally wherein components (a) and/or (b) are preserved by freeze-drying or lyophilization.

Embodiment 20. A vaccine comprising a glycoprotein as prepared using the genetically modified strains, crude cell lysates, compositions, methods or kits of any of embodiments 1-19, wherein the vaccine optionally is lyophilized.

EXAMPLES

The following Examples are illustrative and are not intended to limit the scope of the claimed subject matter.

Example 1—Cell-Free Glycoprotein Synthesis (CFGpS) in Prokaryotic Cell Lysates Enriched with Bacterial Glycosylation Machinery Background and Significance Glycosylation, or the attachment of glycans (sugars) to proteins, is the most abundant post-translational modification in nature and plays a pivotal role in protein folding and activity [1-4]. When it was first discovered in the 1930s [1], glycosylation was thought to be exclusive to eukarya. However, glycoproteins were also discovered in archaea in the 1970s [2, 3], and in bacteria in the late 1990s and early 2000s [4, 5], establishing glycosylation as a central post-translational modification in all domains of life. A vast diversity of glycan structures, including both linear and highly branched polysaccharide chains, have been described [6], giving rise to exponentially increased information content compared to other polypeptide modifications [7].

As a consequence of its role in protein structure and information storage, glycosylation is involved in a variety of biological processes. In eukaryotes, glycoproteins are involved in immune recognition and response, intracellular trafficking, and intercellular signaling [8-11]. Furthermore, changes in glycosylation have been shown to correlate with disease states, including cancer [12-14], inflammation [15-18], and Alzheimer's disease [19]. In prokaryotes, glycosylation is known to play important roles in virulence and host invasion [20-22]. Based on the vital role of glycosylation in numerous biological processes, it has been proposed that the central dogma of biology be adapted to include glycans as a central component [23].

Glycosylation in Nature. Despite the importance of glycans in biology, glycoscience was recently identified as an understudied field. A 2012 National Research Council of the U.S. National Academies report highlighted the critical need for transformational advances in glycoscience [24]. A key challenge preventing the advancement of glycoscience is the inability to precisely control protein glycosylation. Glycoproteins produced in cells are structurally heterogeneous; with diverse glycan patterns resulting from differentially occupied glycosylation sites on a single protein [25]. The discovery of glycosylation pathways in bacteria is enabling new discoveries about this important post-translational modification [26, 27], but production of homogeneous glycoproteins is an outstanding challenge in the field.

Eukaryotic Glycosylation. Glycosylation is ubiquitous in eukaryotes; it is estimated that more than two-thirds of all eukaryotic proteins are glycosylated [28]. The most common forms of glycosylation are asparagine linked (N-linked) and serine (Ser) or threonine (Thr) linked (O-linked) [29]. N-linked glycosylation is characterized by the addition of a glycan moiety to the side chain nitrogen of asparagine (Asn) residues by an oligosaccharyltransferase (OST) that recognizes the consensus sequence Asn-X-Ser/Thr, where X is any amino acid except proline [30, 31]. This process occurs in the endoplasmic reticulum and aids in protein folding, quality control, and trafficking [32]. O-linked glycosylation occurs in the Golgi apparatus following the attachment of N-glycans. Unlike N-linked glycosylation, there is no known consensus sequence for O-linked glycosylation [33, 34]. The ability to site-specifically install N- and O-linked glycans on recombinant proteins to yield homogeneous glycoforms would help us decode the structural and functional consequences of glycan attachment. In other words, the ability to produce homogeneous glycoproteins identical to those found in nature will help us understand nature's need for heterogeneous glycosylation.

Bacterial Glycosylation. Since the recent discovery of bacterial glycosylation, proteins bearing N- and O-linked glycans have been found in a number of bacteria [35, 36]. The best-studied bacterial glycosylation system is the pgl pathway from *Campylobacter jejuni*, which has been shown to express functionally in *Escherichia coli* (FIG. 1) [37]. In *C. jejuni*, proteins are N-glycosylated with the 1.406 kDa GlcGalNAc5Bac heptasaccharide (Glc: glucose, GalNAc: N-acetylgalactosamine, Bac: bacillosamine). GTs assemble the heptasaccharide onto the lipid anchor undecaprenol pyrophosphate (Und-PP), which is then used as a substrate for the OST (PglB) for N-linked glycosylation [36, 38, 39]. This pathway is significantly simpler than eukaryotic glycosylation pathways, and has been leveraged to increase our understanding of the mechanism of N-linked glycosylation [26, 27].

Glycosylated Protein Therapeutics. Glycosylation is critically important for the production of recombinant protein therapeutics. Approximately 70% of the >100 protein products approved by U.S. and European regulatory agencies and the ~500 candidates in clinical trials are glycosylated. Glycans impact many therapeutically relevant protein properties including pharmacokinetics, immunogenicity, and biological activity [40-42]. In fact, recent studies have shown that engineering of a protein's glycosylation pattern can produce drugs with improved efficacy [43, 44]. Further efforts have been made to engineer yeast [45-47] and Chinese Hamster Ovary (CHO) [48, 49] cells to produce homogeneous glycoprotein products with superior therapeutic efficacy. However, this work is limited by cell viability constraints: deletion of unwanted native glycosylation machinery may not be possible due to the lethality of the gene deletion [50]. The inability to produce homogeneous glycoforms in eukaryotic hosts has prompted recent efforts to enable glycoprotein production in *E. coli* through the addition of orthogonal glycosylation machinery.

Bacterial Glycoengineering. Bacterial glycoengineering is an emerging field that aims to harness bacterial glycosylation systems for the creation of novel therapeutics, vaccines, and diagnostics [51, 52]. Bacterial glycoengineering takes advantage of the recent discovery that orthogonal glycosylation machinery can be can be transferred into *E. coli* [37, 53]. Bacteria like *E. coli* provide a blank canvas for which to study glycosylation and engineer synthetic glycosylation pathways, as they lack native glycosylation machinery. To date, the DeLisa lab has recreated the initial steps of human N-linked glycosylation in *E. coli*, demonstrating production of glycoproteins bearing the eukaryotic trimannosyl core glycan with very low glycoform heterogeneity [54]. This is a significant development and opens the door to production of homogeneously glycosylated eukaryotic glycoproteins in bacterial systems.

Cell-Free Protein Synthesis. Cell-free protein synthesis (CFPS) is an emerging technology that allows for the production of proteins in crude cell lysates [55, 56]. CFPS technology was first used over 50 years ago by Nirenberg and Matthaei to decipher the genetic code [57]. In the late 1960s and early 1970s, CFPS was employed to help elucidate the regulatory mechanisms of the *E. coli* lactose [58] and tryptophan [59] operons. In the last two decades, CFPS platforms have experienced a surge in development to meet the increasing demand for recombinant protein expression technologies [55].

CFPS offers several advantages for recombinant protein expression. In particular, the open reaction environment allows for addition or removal of substrates for protein synthesis, as well as precise, on-line reaction monitoring. Additionally, the CFPS reaction environment can be wholly directed toward and optimized for production of the protein product of interest. CFPS effectively decouples the cell's objectives (growth & reproduction) from the engineer's objectives (protein overexpression & simple product purification). Overall, CFPS technology allows for shortened protein synthesis timelines and increased flexibility for addition or removal of substrates compared to in vivo approaches. The *E. coli* CFPS system in particular has been widely adopted because of i) its high batch yields, with up to 2.3 g/L of green fluorescent protein (GFP) reported [60], ii) inexpensive required substrates [61-63], and iii) the ability to linearly scale reaction volumes over $10^6$ L [64].

Glycosylation is possible in some eukaryotic CFPS systems, including ICE, CHO extract, and a human leukemia cell line extract [65-68]. However, these platforms harness the endogenous machinery to carry out glycosylation, meaning that i) the possible glycan structures are restricted to those naturally synthesized by the host cells and ii) the glycosylation process is carried out in a "black box" and thus difficult to engineer or control. The development of a highly active E. coli CFPS platform has prompted recent efforts to enable glycoprotein production in E. coli lysates through the addition of orthogonal glycosylation components. In one study, Guarino and DeLisa demonstrated the ability to produce glycoproteins in E coli CFPS by adding purified lipid-linked oligosaccharides (LLOs) and the C. jejuni OST to a CFPS reaction. Yields of between 50-100 µg/mL of AcrA, a C. jejuni glycoprotein, were achieved [69]. Despite these recent advances, bacterial cell-free glycosylation systems have been limited by their inability to co-activate efficient protein synthesis and glycosylation. Addressing this gap would have a transformative effect on CFPS, glycoengineering, glycoscience, and therapeutic development.

Results and Discussion

Figure 2:
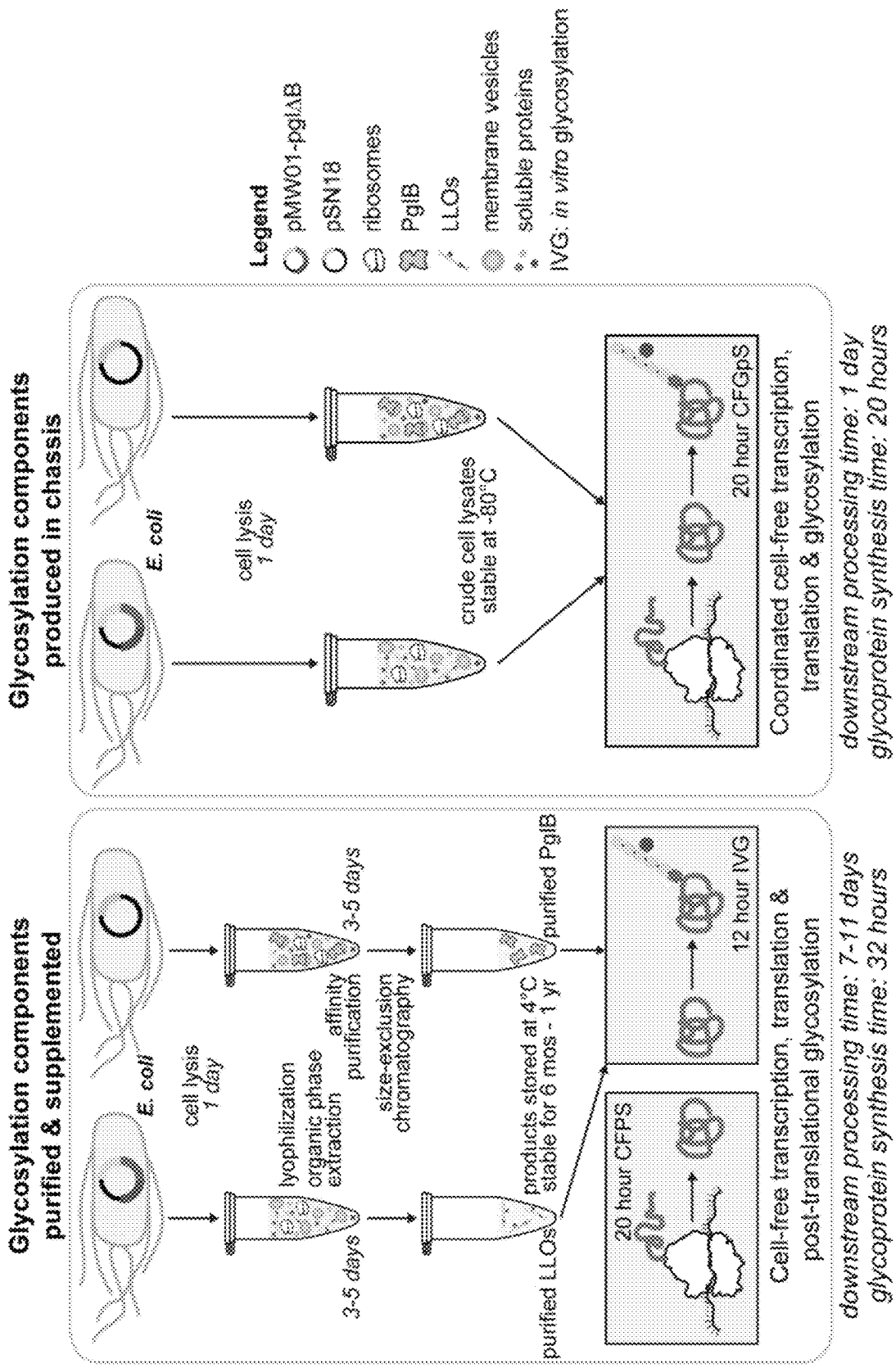
FIG. 2. Production of glycosylation machinery in the chassis strain enables co-translational glycosylation in crude E. coli lysates. The CFGpS system (right) reduces both the downstream processing time and glycoprotein synthesis time compared to the state-of-the-art cell-free glycosylation system (left).

Recent work demonstrated the production of glycoproteins in E. coli lysates by adding purified lipid-linked oligosaccharides (LLOs) and the OST from C. jejuni (PglB) to a CFPS reaction [69] (FIG. 2, left). However, this system depends on the use of purified LLOs and PglB, which are both membrane bound in vivo. As a result, complete purification of both of LLOs and OSTs is time-consuming and results in products that are relatively unstable (FIG. 2, left). Further, glycoproteins were produced using a sequential translation/glycosylation strategy, which prolongs the CFPS reaction time by an additional 12 hours. A CFGpS system in which i) all the biosynthetic machinery for protein synthesis and glycosylation is supplied by the E. coli lysate and ii) glycosylation and translation occur in an all-in-one reaction would greatly simplify in vitro glycoprotein production (FIG. 2, right).

We have developed a cell-free glycoprotein synthesis (CFGpS) system capable of coordinated in vitro transcription, translation, and glycosylation in crude E. coli lysates via selective enrichment of lysates with glycosylation components. We hypothesized that co-translational glycosylation can be achieved in crude E. coli lysates via overexpression of LLO biosynthesis machinery and OSTs in the glycosylation and produce up to 1-1.5 g/L protein in CFPS using multiplexed automated genome engineering (MAGE) [70, 71]. We used purified C. jejuni LLOs and PglB to show that glycosylation components are present in crude lysates and participate in N-linked glycosylation. Next, we used these lysates to carry out co-translational glycosylation of proteins in crude E. coli lysates and characterize the in vitro activity of four PglB homologs with natural sequence variation compared to the archetypal CjPglB. The CFGpS platform is modular, flexible, and has promising applications as a high-throughput prototyping platform for glycoproteins of biotechnological interest. This technology is a valuable addition to the CFPS and glycoengineering communities and complements previously developed in vivo glycosylation activity assays.

Genome engineering chassis strains for CFGpS. We first engineered novel glycosylation chassis strains to enable CFGpS. rEcoli 705 was selected as a base strain for this work because it lacks several endogenous nucleases and proteases, enabling in vitro protein synthesis yields of up to 2 mg/mL (Martin, et. al., in prep). Additionally, 705 is derived from E. coli K12, which lacks endogenous N-linked glycosylation machinery, providing a "clean chassis" for glycoengineering.

Two gene candidates were selected for deletion in the 705-based glycosylation host strains. The E. coli waaL gene encodes the WaaL O antigen ligase in the LPS biosynthesis pathway, which catalyzes the transfer of LLOs to lipid A [72]. The waaL genomic deletion increases the availability of LLO substrates for glycosylation. An additional genetic knockout was identified to increase the accumulation of Man3GlcNAc2 (Man3GlcNAc2, Man: mannose, GlcNAc: N-acetylglucosamine) LLOs. The gmd gene in E. coli encodes GDP-mannose dehydratase, which catalyzes the conversion of GDP-mannose to GDP-4-keto-6-deoxymannose [73]. Deletion of gmd increases the availability of GDP-mannose substrates for the assembly of the Man3GlcNAc2 LLOs.

Figure 3:
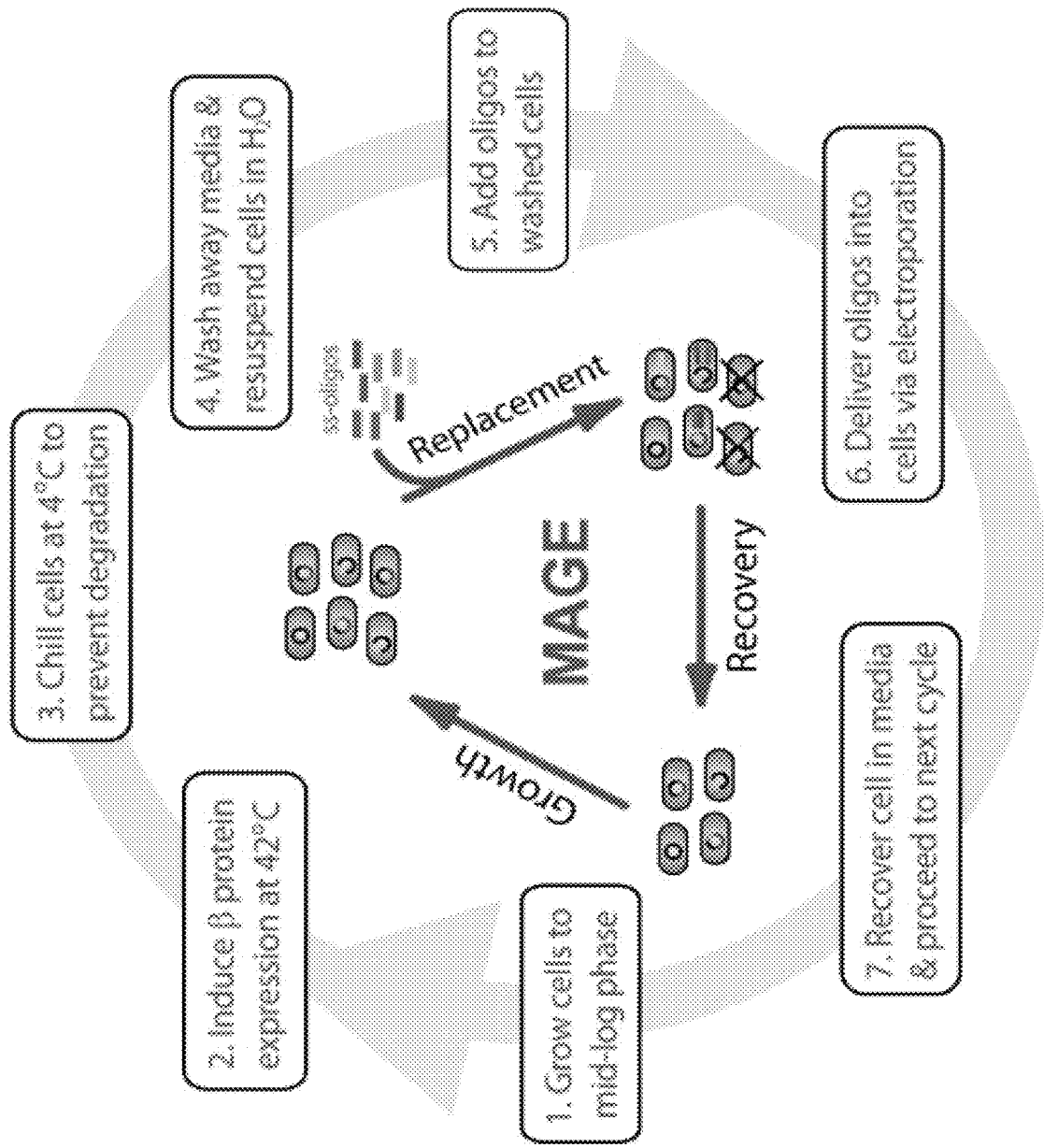
FIG. 3. Engineering high-yielding glycosylation chassis strains using MAGE. (A) Schematic depicting MAGE experimental procedure. MAGE enables rapid insertion of multiple genetic modifications. (B) Verification of engineered chromosomal mutations using multiplexed allele-specific PCR. Mutant alleles were amplified using forward primers specific to the designed chromosomal mutations. PCR and sequencing results confirmed the desired 705ΔwaaL and 705ΔgmdΔwaaL genotypes. (C) Lysates were produced from 705, 705ΔwaaL, 705ΔgmdΔwaaL, and BL21(DE3) and used to synthesize sfGFP in CFPS reactions lasting 20 hours. Active sfGFP was quantified by fluorescence. Values shown are means with error bars representing the standard deviation of at least three independent experiments.
Figure 3:
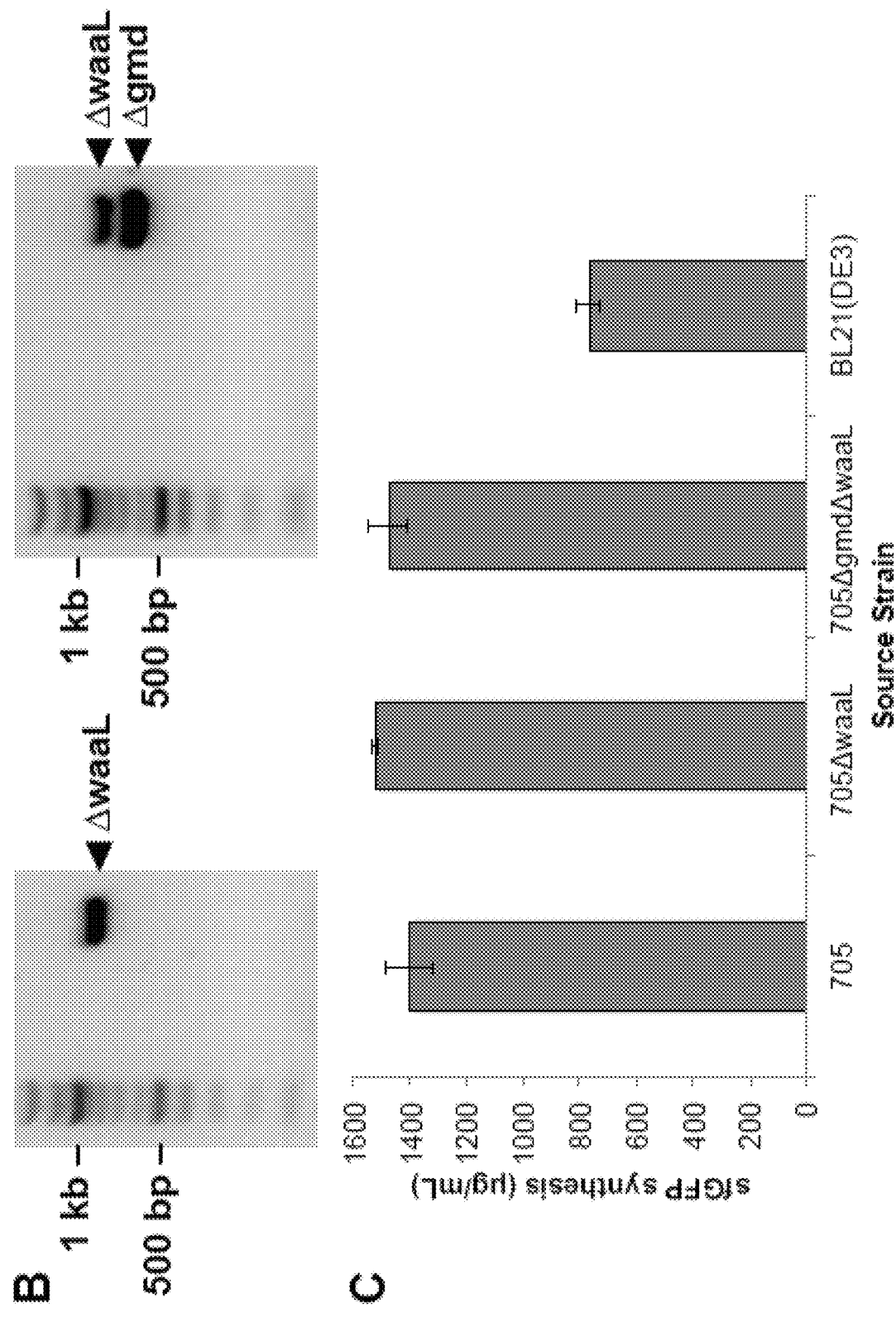

We used MAGE to simultaneously engineer both 705ΔwaaL and 705ΔgmdΔwaaL knockout strains [71]. I designed MAGE oligos to introduce a stop codon (TAA), a frame-shift mutation, and a second (in frame) stop codon within 200 bp of the 5' end of the gmd and waaL genes [70]. Colonies with the single ΔwaaL knockout as well as the double knockout ΔgmdΔwaaL we isolated after 15 rounds of MAGE and screening of 96 colonies. The 705ΔwaaL and 705ΔgmdΔwaaL strains reach yields of 1-1.5 mg/mL sfGFP in 20-hour CFPS reactions (FIG. 3). Furthermore, lysates from these strains yield approximately 400 µg/mL AcrA, a C. jejuni glycoprotein, in CFPS (data not shown). This is significantly higher than the 50-100 µg/mL AcrA produced using the state-of-the-art CFGpS system [69]. Thus, I have developed E. coli glycosylation chassis strains capable of in vitro protein synthesis at yields higher than any previously reported.

Coordinated cell-free transcription/translation/glycosylation of diverse glycoproteins using lysate-derived glycosylation components. The N-linked glycosylation pathway from C. jejuni is the best-studied prokaryotic glycosylation system to date, and has been shown to express functionally in E. coli [37]. We hypothesized that C. jejuni LLOs and OST could be enriched in S30 lysates via overexpression of C. jejuni glycosylation machinery in an E. coli CFGpS chassis strain. To test this hypothesis, we produced lysates from cells overexpressing either the C. jejuni LLO biosynthesis pathway (CjLLO lysate) or the C. jejuni OST (CjOST lysate). CjLLO lysates were prepared from CLM24 cells expressing vector pMW07-pglΔB, which encodes the C. jejuni pgl pathway with a truncated and non-functional PglB gene [74]. CjOST lysates were prepared from CLM24 cells expressing vector pSF CjPglB, which encodes the C. jejuni OST, PglB (CjPglB). CLM24 was chosen initially as a chassis because it has been previously used as an in vivo glycosylation chassis strain [53]. Lysates were prepared via high-pressure homogenization, to encourage formation of soluble inverted membrane vesicles, which carry membrane-bound components, such as LLOs and PglB, into the crude lysate. LLOs and OST were produced in separate host strains for three reasons: i) to decrease the metabolic burden of protein overexpression on the CFGpS chassis strain, ii) to prevent premature release of glycans by the OST, which has been observed when the OST and LLOs are overexpressed in vivo in the absence of target protein (DeLisa laboratory, unpublished data), and iii) to enable identification of LLOs or OST as the limiting reagent for glycoprotein synthesis.

Figure 5:
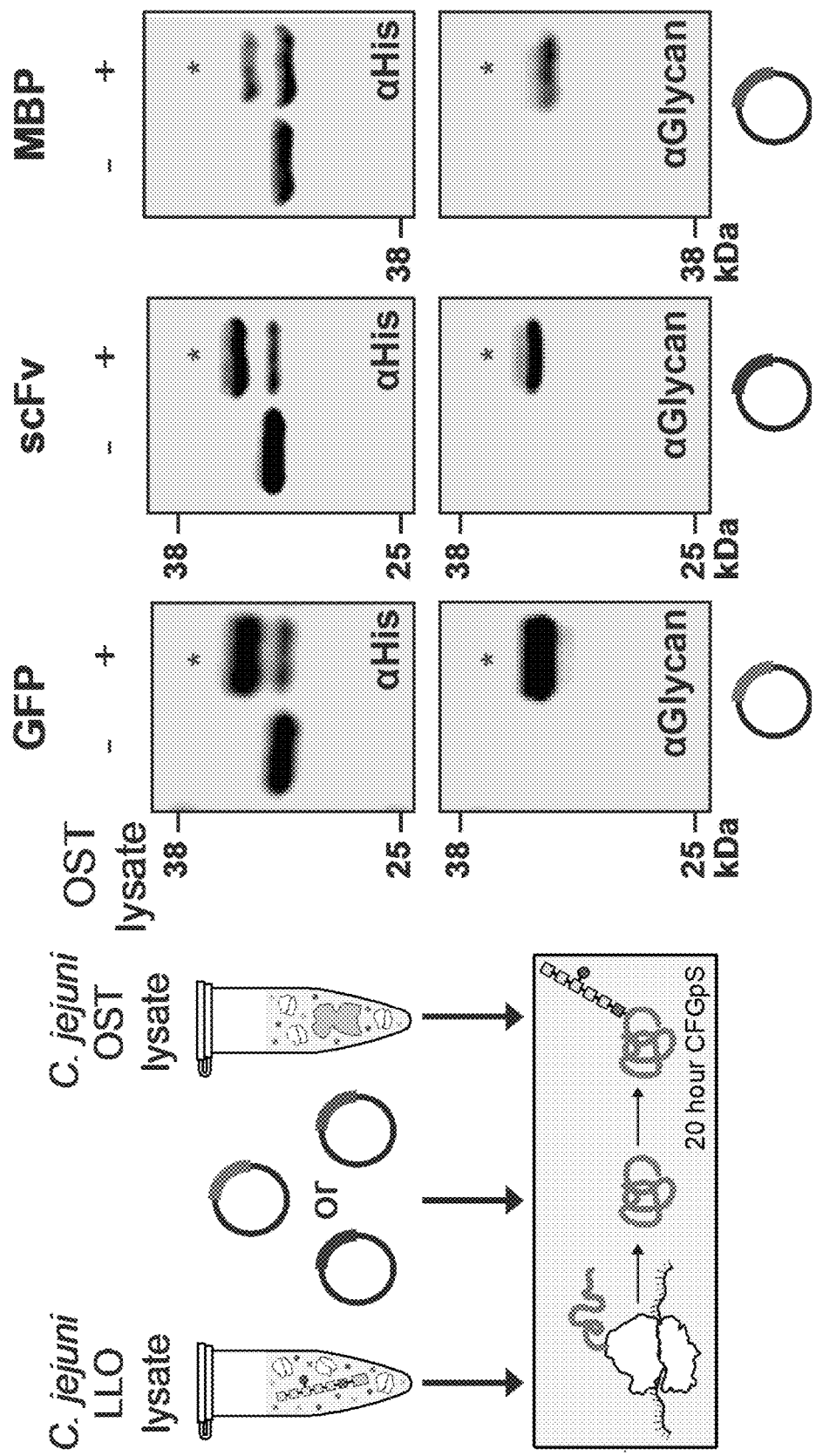
FIG. 5. One-pot protein synthesis and glycosylation in S30 lysates enriched with *C. jejuni* glycosylation machinery. S30 lysates were prepared from CLM24 cells expressing the *C. jejuni* glycan biosynthesis pathway (CjLLO lysate) and cells expressing *C. jejuni* OST (CjOST lysate). Lysates were mixed and used to produce sfGFP-21-DQNAT-6×His (left), scFv13-R4-DQNAT-6×His (middle), and MBP-4×DQNAT-6×His (right) in CFGpS reactions lasting 20 hours. Glycosylated sfGFP-21-DQNAT, R4-DQNAT, and MBP-4×DQNAT are produced only when both the CjLLO and CjOST lysates are both added to the reaction, as evidenced by an increase in protein molecular weight corresponding to the covalent addition of the 1.4 kDa *C. jejuni* heptasaccharide to the target protein, as well as the cross-reactivity of the glycosylated protein band with both anti-His and anti-Glycan antibodies (asterisks). Abbreviations: OST lysate: CLM24 pSF_CjPglB; MBP: maltose binding protein; αGlycan: rabbit antiserum specific for *C. jejuni* N-linked glycan.

Based on previous work in the Jewett lab, which demonstrated that metabolic pathways can be reconstituted in vitro via lysate mixing (Dudley, et al. "Cell-Free Mixing of *Escherichia Coli* Crude Extracts to Prototype and Rationally Engineer High-Titer Mevalonate Synthesis," ACS Synth Biol 5 (12), 1578-1588. 2016 Aug. 22, the content of which is incorporated herein by reference in its entirety), we hypothesized that the full *C. jejuni* glycosylation pathway could be reconstituted in vitro by mixing the CjLLO and CjOST lysates. This lysate mixing approach retains the advantage of reduced metabolic burden on the chassis strain and eliminates the possibility of glycan hydrolysis in the absence of glycosylation acceptor protein. To test this hypothesis, the CjLLO and CjPglB lysates were mixed and supplied with DNA template encoding: i) super-folder green fluorescent protein engineered to include a DQNAT glycosylation site (sequon) in a 21-amino acid flexible linker inserted at residue T216 and a C-terminal His tag (sfGFP-21-DQNAT-6×His; FIG. 5, left), ii) a short chain antibody fragment with a C-terminal DQNAT (SEQ ID NO:6) sequon followed by a His tag (scFv13-R4-DQNAT-6×His; FIG. 5, middle), or iii) an engineered maltose binding protein construct with four C-terminal repeats of the DQNAT (SEQ ID NO:6) sequon and a C-terminal His tag (MBP-4×DQNAT-6×His; FIG. 5, right). Within the first hour of the CFGpS reaction, reaction mixtures were spiked with manganese chloride ($MnCl_2$) and n-dodecyl-β-D-maltopyranoside (DDM) detergent at final concentrations of 25 mM $MnCl_2$, 0.1% w/v DDM to optimize CjPglB activity (Jewett lab, unpublished data). Glycosylated sfGFP-21-DQNAT, R4-DQNAT, and MBP-4×DQNAT are produced in CFGpS reactions lasting 20 hours only when both the CjLLO and CjOST lysates are both added to the reaction (FIG. 5). These results show, for the first time, i) it is possible to enrich crude *E. coli* lysates with active LLOs and OSTs via engineering of the chassis strain and ii) that it is possible to co-activate in vitro transcription, translation, and glycosylation of proteins. Additionally, by demonstrating production of multiple glycoprotein targets, this work demonstrates the flexibility of mixed lysate CFGpS for synthesis of diverse glycoproteins in rapid 20 hour reactions.

Figure 4:
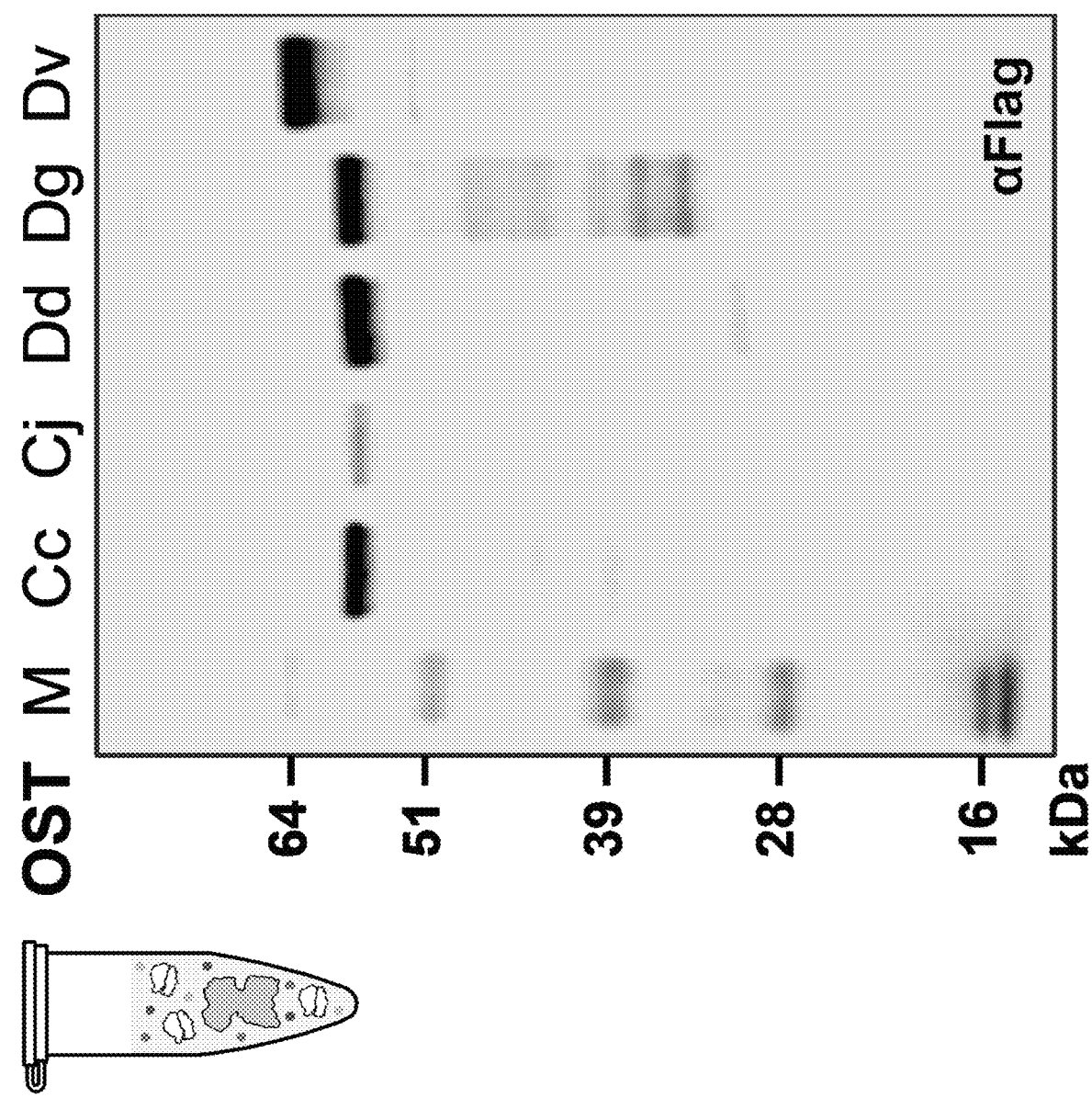
FIG. 4. S30 lysates from CLM24 cells overexpressing bacterial OSTs are selectively enriched with enzymes. S30 lysates prepared from CLM24 cells expressing Flag-tagged PglB homologs from *C. jejuni* (CjOST lysate), *C. coli* (CcOST lysate), *D. desulfuricans* (DdOST lysate), *D. gigas* (DgOST lysate), & *D. vulgaris* (DvOST lysate) were analyzed by SDS-PAGE. Full-length OST products were observed between 51 and 64 kDa. Abbreviations: M: protein ladder, Cc: *C. coli*, Cj: *C. jejuni*, Dd: *D. desulfuricans*, Dg: *D. gigas*, Dv: *D. vulgaris*.
Figure 6:
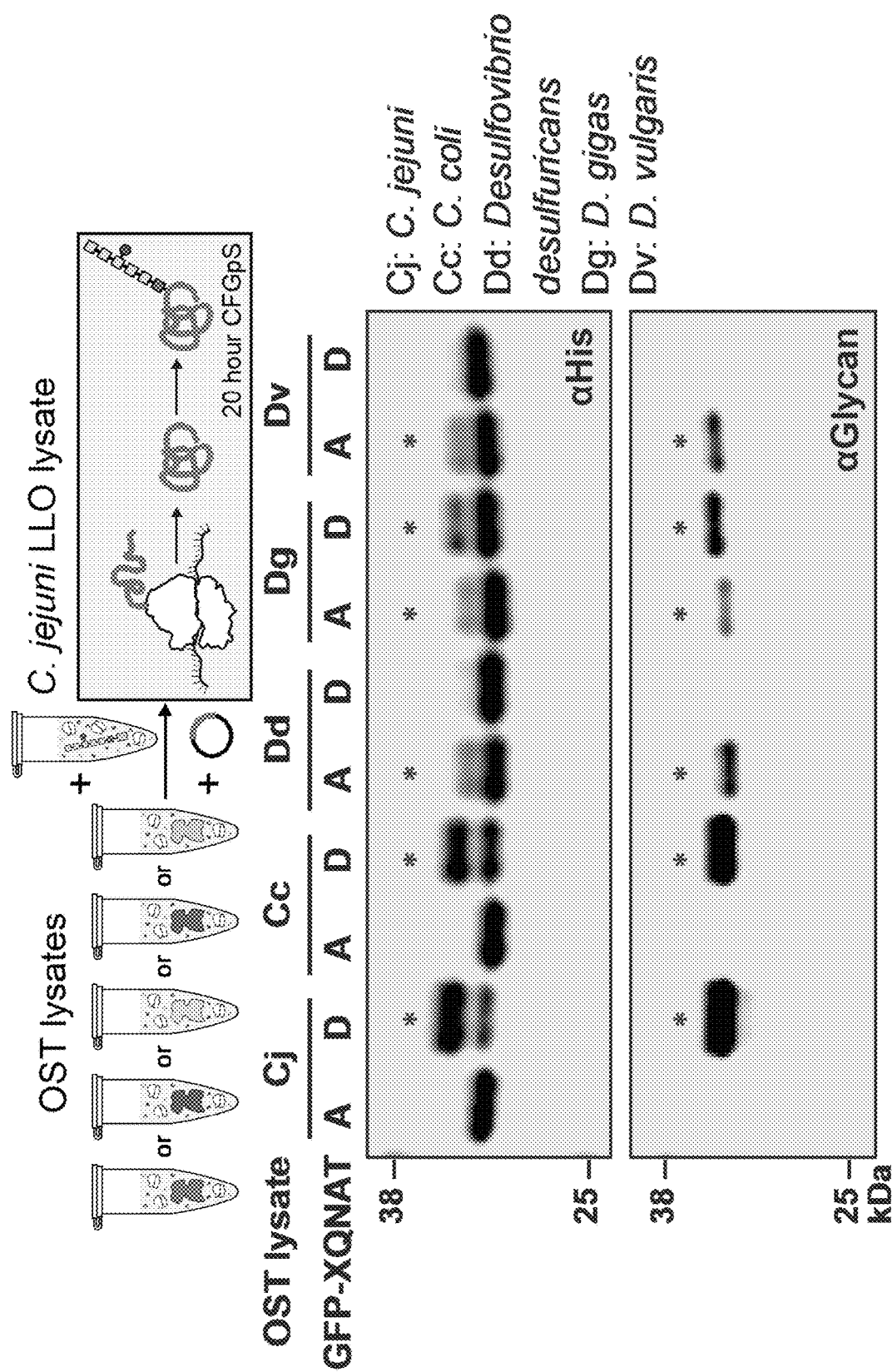
FIG. 6. Prototyping activities of OST homologs for *C. jejuni* glycan in CFGpS. Schematic showing lysate mixing strategy for rapid prototyping of OST lysates with CjLLO lysate via CFGpS (top). S30 lysates were prepared from CLM24 cells expressing OST homologs from *C. jejuni* (CjOST lysate), *C. coli* (CcOST lysate), *D. desulfuricans* (DdOST lysate), *D. gigas* (DgOST lysate), & *D. vulgaris* (DvOST lysate). These lysates were mixed with CjLLO lysates in CFGpS reactions containing DNA template for either sfGFP-21-AQNAT-6×His or -DQNAT-6×His. *C. jejuni* & *C. coli* OSTs show glycosylation activity on the DQNAT glycosylation sequence (asterisks; lanes 2, 4). *D. gigas* OST glycosylates both the AQNAT and DQNAT constructs (asterisks; lanes 7, 8). *D. desulfuricans* and *D. vulgaris* OSTs preferentially glycosylate the AQNAT (SEQ ID NO:5) sequon (asterisks; lanes 5, 9). Abbreviations: αGlycan: rabbit antiserum specific for *C. jejuni* N-linked glycan.

Prototype OST activity in CFGpS. In order to identify OSTs with potentially improved glycosylation efficiency compared to CjPglB, we used CFGpS to prototype the in vitro activity of four additional bacterial OSTs with both low (<25%) and high (>65%) sequence homology to CjPglB that have recently been studied in vivo in *E. coli* (Ollis et al. "Substitute sweetener: diverse bacterial oligosaccharyltransferases with unique N-glycosylation site preferences," *Sci. Rep.* 2015 Oct. 20; 5:15237). Crude lysates were prepared from CLM24 cells expressing the pSF vector encoding homologs of CjPglB from *C. jejuni*, *C. coli*, *Desulfovibrio desulfuricans*, *Desulfovibrio gigas*, and *Desulfovibrio vulgaris* under the control of the araC transcriptional regulator. Western blot analysis showed that the OSTs were present in the crude cell lysates (FIG. 4). The OST lysates were mixed with CjLLO lysate and used to synthesize either scFv13-R4-AQNAT or DQNAT in CFGpS reactions. *C. jejuni* & *C. coli* PglB show glycosylation activity on the DQNAT glycosylation sequence, *D. gigas* PglB glycosylates both the DQNAT and AQNAT sequences, and *D. desulfuricans* & *D. vulgaris* PglB preferentially glycosylate the AQNAT sequence (FIG. 6). Importantly, the glycosylation activities observed in vitro largely (80-90%) correspond to the reported in vivo activities [2]. This validates the use of the CFGpS platform for prototyping OST activities or potentially for novel OST discovery and functional characterization.

Figure 7:
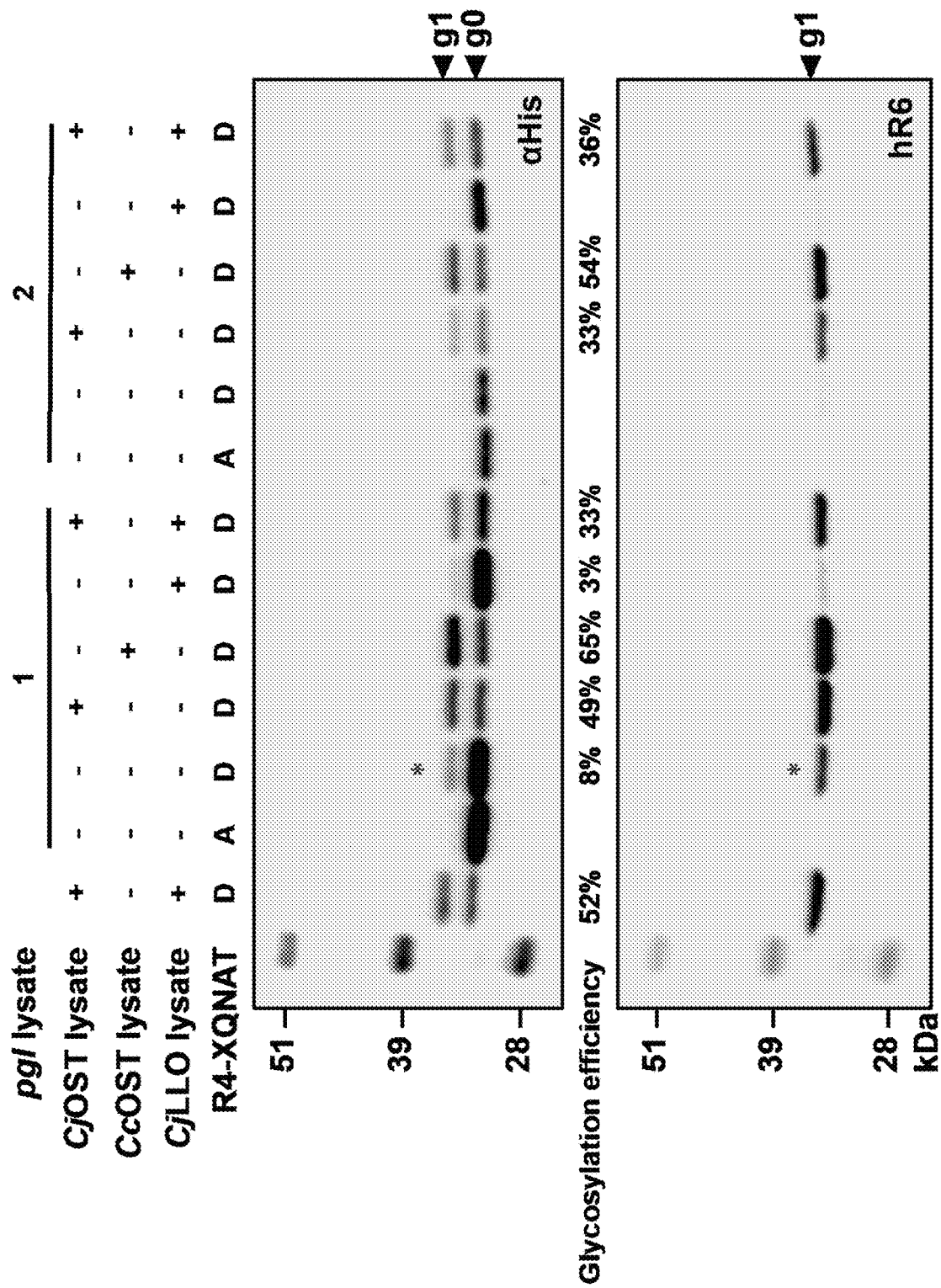
FIG. 7. Overexpression of full *C. jejuni* glycosylation pathway in chassis results in an all-in-one lysate for CFGpS. S30 lysate was prepared from 705 waaL- or CLM24 cells expressing the pgl locus from *C. jejuni* (pgl lysate). The pgl lysate was used directly or supplemented with CjLLO lysate and/or CjOST and/or CcOST lysate, as noted, in CFGpS reactions lasting 20-24 hours and containing DNA template for either scFv13-R4-AQNAT-6×His or -DQNAT-6×His. Glycosylation efficiencies were determined via densitometry. Notably, the 705 waaL$^-$ lysate, but not the CLM24 lysate, is capable of one-pot CFGpS (lane 3, asterisks). Thus, the all-in-one lysate from our engineered glycosylation chassis strain produces higher yields of glycosylated R4 than lysate from CLM24, a state-of-the-art glycosylation chassis strain. Abbreviations: pgl lysate 1: 705 waaL$^-$ pACYC-pgl; pgl lysate 2: CLM24 pACYC-pgl; CjOST lysate: CLM24 pSN18 0.02% arabinose; CcOST lysate: CLM24 pSF *C. coli* 0.02% arabinose; CjLLO lysate: 705 waaL$^-$ pPglAB 0.02% arabinose; hR6: rabbit antiserum specific for *C. jejuni* N-linked glycan; g0: aglycosylated R4; g1: monoglycosylated R4.

Example 2—CFGpS in an All-In-One Prokaryotic Cell Lysate Enriched with Bacterial Glycosylation Machinery Toward engineering an all-in-one *E. coli* strain for CFGpS. To build on the mixed lysate system we have developed, we worked to build an *E. coli* chassis strain expressing an LLO biosynthetic pathway and an OST enzyme to create an all-in-one *E. coli* lysate containing both LLOs and OST that is capable of producing glycoprotein without additional purified or extracted components. As a proof-of-concept, we designed two chassis strains expressing the LLOs and OST from the *C. jejuni* N-linked glycosylation pathway. S30 lysate was prepared from 705 waaL- or CLM24 cells expressing the pgl locus from *C. jejuni* (pgl lysate). The pgl lysate was used directly or supplemented with CjLLO lysate and/or CjOST and/or CcOST lysate, as noted, in CFGpS reactions lasting 20-24 hours and containing DNA template for either scFv13-R4-AQNAT-6×His or -DQNAT-6×His. Notably, the 705 waaL-lysate, but not the CLM24 lysate, is capable of one-pot CFGpS (FIG. 7). However, the 705 waaL⁻ lysate is OST limited, as evidenced by the increased glycosylation efficiency following addition of CjOST or CcOST lysates. (FIG. 7). This result provides proof-of-concept for engineering chassis *E. coli* strain, which furnishes lysate that can activate coordinated in vitro transcription, translation, and glycosylation. Additionally, the all-in-one lysate from our engineered glycosylation chassis strain 705 waaL⁻ produces higher yields of glycosylated R4 than lysate from CLM24, a state-of-the-art glycosylation chassis strain. Future work will focus on increasing glycosylation efficiency in this all-in-one system.

Figure 8:
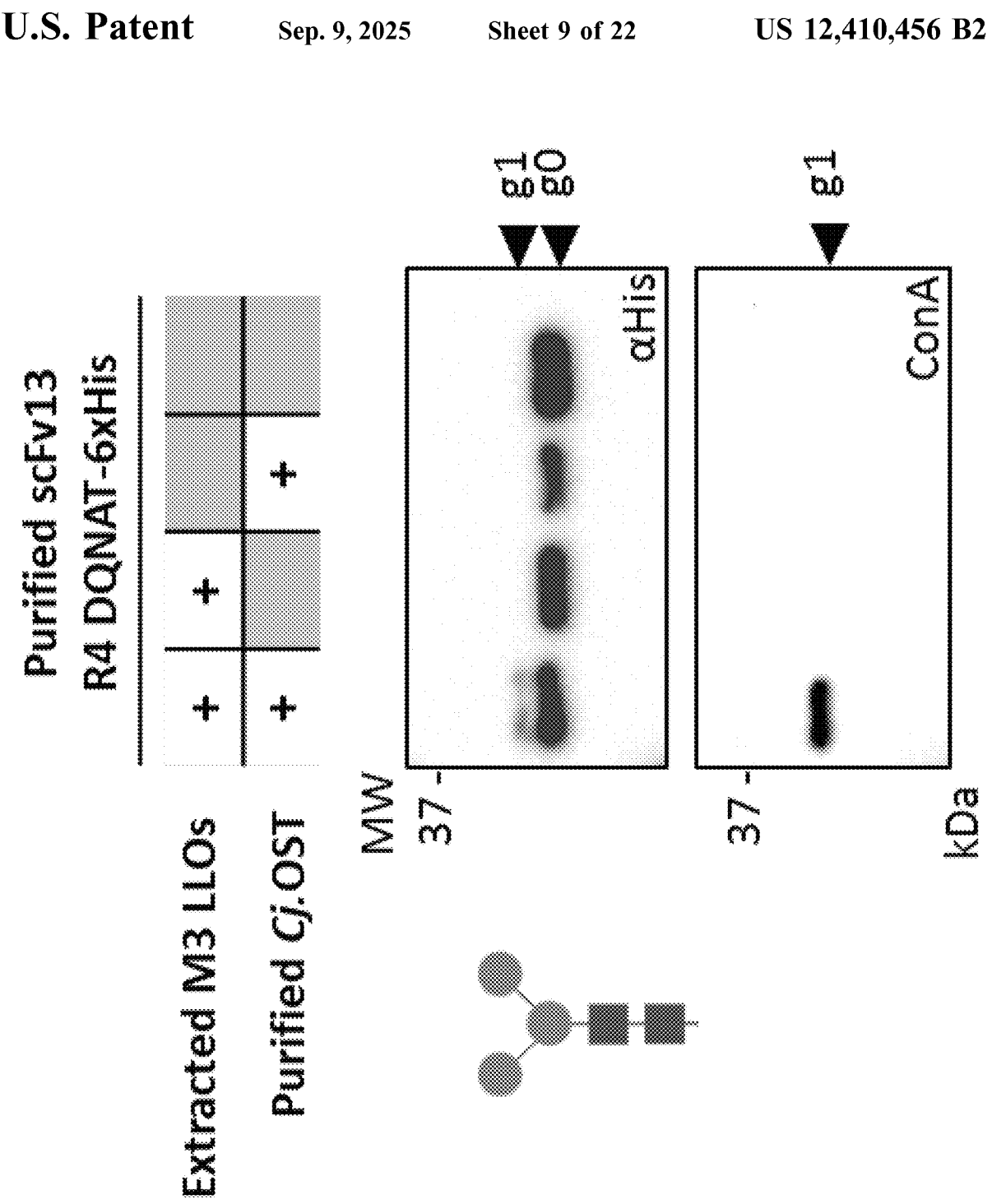
FIG. 8. Immunoblot analysis of glycosylated scFv13-R4 bearing the eukaryotic core glycan Man$_3$GlcNAc$_2$ generated by in vitro glycosylation. Target protein scFv13-R4 bearing a C-terminal DQNAT (SEQ ID NO:6) acceptor sequon was incubated with Man$_3$GlcNAc$_2$ lipid-linked oligosaccharides (M3 LLOs) and purified oligosaccharyltransferase enzyme PglB from *Campylobacter jejuni* (CjOST). Detection of protein was performed using anti-His6×-antibody (top panel). Detection of Man$_3$GlcNAc$_2$ was performed using concanavalin A (ConA) lectin. Glycosylated scFv13-R4 (g1) is detected only in the presence of both CjOST and Man$_3$GlcNAc$_2$ LLOs (lane 1) whereas scFv13-R4 remains aglycosylated (g0) when any of the components was omitted (lanes 2-4).

Example 3—CFGpS Using Purified Bacterial and/or Eukaryotic Glycosylation Machinery Cell-free humanized protein glycosylation. To introduce humanized glycans into CFGpS system, we first used purified components to perform the decoration of targeted protein with $Man_3GlcNAc_2$ glycan. Glycosylated antibody fragment was synthesized by combining purified scFv13 R4 targeted protein, purified PglB enzyme, and extracted LLOs bearing $Man_3GlcNAc_2$ glycan (FIG. 8). $Man_3GlcNAc_2$ LLOs were extracted from optimized plasmids and strain for producing this particular glycan. Specifically, pConYCG plasmid containing biosynthetic pathway for $Man_3GlcNAc_2$ carbohydrate moiety was transformed into our engineered *E. coli* origami ΔwaaL Δgmd::kan strain. This strain has been shown to improve the homogeneity of the final $Man_3GlcNAc_2$ product. In addition, plasmid pManCB encoding phosphomannomutase (manB) and mannose-1-phosphate guanylyltransferase (manC) enzymes was also transformed and co-expressed with pConYCG. The overexpression of the manB and manC enzymes increase GDP-mannose precursor, improving the synthesis yield of $Man_3GlcNAc_2$ glycan. The glycosylation of $Man_3GlcNAc_2$ glycan on our targeted protein has been further confirmed by Electron-Transfer/Higher-Energy Collision MS/MS (EThcD-MS/MS) analysis to identify the mass of decorated glycan as well as to locate the specific glycosylation site (data not shown). The mass spectrometry results provided evidence of N-linked glycosylation at the specific DQNAT (SEQ ID NO:6) sequon with only single glycan mass of 892.317 Da observed, which is consistent with the molecular weight of the $Man_3GlcNAc_2$ glycan.

Conclusions

We describe here a CFGpS system capable of coordinated transcription, translation, and bacterial or eukaryotic glycosylation in vitro. CFGpS uniquely (i) decouples cell viability from glycosylation activity and enables reduction of cellular metabolic burden through in vitro reconstitution of glycosylation components, (ii) permits design-build-test (DBT) iterations on individual glycosylation components, and (iii) allows for assembly of glycosylation pathways within well-defined experimental conditions including chemical and physical manipulations not possible in cells. This technology has utility for prototyping and characterizing OSTs and both natural and synthetic LLO biosynthesis pathways for fundamental discovery or therapeutic development. The CFGpS system will deepen our understanding of glycosylation and opens the door to rationally designed glycoprotein therapeutics and vaccines.

Example 4—A Cell-Free Platform for Rapid Synthesis and Testing of Active Oligosaccharyltransferases Reference is made to the scientific article Schoborg et al., "A cell-free platform for rapid synthesis and testing of active oligosaccharyltransferases," *Biotechnol Bioeng.* 2018 March; 115(3):739-750, the content of which is incorporated herein by reference in its entirety.

Example 5—Single-Pot Glycoprotein Biosynthesis Using a Cell-Free Transcription-Translation System Enriched with Glycosylation Machinery Reference is made to the manuscript entitled "Single-pot glycoprotein biosynthesis using a cell-free transcription-translation system enriched with glycosylation machinery," Thapakorn Jaroentomeechai, Jessica C. Stark, Aravind Natarajan, Cameron J. Glasscock, Laura E. Yates, Karen J. Hsu, Milan Mrksich, Michael C. Jewett, and Matthew P. DeLisa, currently in press DOI: *10.1038/s41467-018-05110-x, the content of which is incorporated herein by reference in its entirety.

Abstract

The emerging discipline of bacterial glycoengineering has made it possible to produce designer glycans and glycoconjugates for use as vaccines and therapeutics. Unfortunately, cell-based production of homogeneous glycoproteins remains a significant challenge due to cell viability constraints and the inability to control glycosylation components at precise ratios in vivo. To address these challenges, we describe a novel cell-free glycoprotein synthesis (CFGpS) technology that seamlessly integrates protein biosynthesis with asparagine-linked protein glycosylation. This technology leverages a glyco-optimized *Escherichia coli* strain to source cell extracts that are selectively enriched with glycosylation components, including oligosaccharyltransferases (OSTs) and lipid-linked oligosaccharides (LLOs). The resulting extracts enable a one-pot reaction scheme for efficient and site-specific glycosylation of target proteins. The CFGpS platform is highly modular, allowing the use of multiple distinct OSTs and structurally diverse LLOs. As such, we anticipate CFGpS will facilitate fundamental understanding in glycoscience and make possible applications in on-demand biomanufacturing of glycoproteins.

Introduction

Asparagine-linked (N-linked) protein glycosylation is one of the most common post-translational modifications in eukaryotes, and profoundly affects protein properties such as folding, stability, immunogenicity, and pharmacokinetics[1-3]. The attached N-glycans can participate in a wide spectrum of biological processes such as immune recognition/response[4,5] and stem cell fate[6]. Moreover, the intentional engineering of protein-associated glycans can be used to manipulate protein therapeutic properties such as enhancing in vivo activity and half-life[7].

At present, however, the inherent structural complexity of glycans and the corresponding difficulties producing homogeneously glycosylated proteins have slowed advances in our understanding of glycoprotein functions and limited opportunities for biotechnological applications. Moreover, because glycan biosynthesis is neither template-driven nor genetically encoded, glycans cannot be produced from recombinant DNA technology. Instead, N-glycans are naturally made by coordinated expression of multiple glycosyltransferases (GTs) across several subcellular compartments. This mode of biosynthesis combined with the lack of a strict proofreading system results in inherent glycan heterogeneity and accounts for the large diversity of structures in the expressed glycan repertoire of a cell or organism[8,9]. Further complicating matters is the paucity of structure-function relationships for GTs, which hinders a priori prediction of glycan structure. Altogether, these factors have frustrated production of homogeneous glycans and glycoconjugates in biological systems and restricted our capacity to elucidate the biochemical and biophysical effects of glycans on the proteins to which they are attached. Thus, there is an unmet need for a technology capable of rapidly producing useful quantities of proteins featuring user-specified glycosylation for biochemical and structural biology studies.

Recent pioneering efforts in glycoengineering of cellular systems including mammalian[10], yeast[11], and bacterial cells[12] have expanded our ability to reliably synthesize chemically defined glycans and glycoproteins. Despite the promise of these systems, protein expression yields often remain low and design-build-test (DBT) cycles—iterations of re-engineering organisms to test new sets of enzymes—can be slow. One promising alternative to cell-based systems is cell-free protein synthesis (CFPS) in which protein synthesis occurs in vitro without using intact, living cells. Recently, a technical renaissance has revitalized CFPS systems to help meet increasing demands for simple and efficient protein synthesis, with *Escherichia coli*-based CFPS systems now exceeding grams of protein per liter reaction volume[13], with the ability to support co- or post-translational modifications[14-17]. As a complement to in vivo expression systems, cell-free systems offer several potential advantages. First, the open nature of the reaction allows the user to directly influence biochemical systems of interest. As a result, new components can be added or synthesized, and maintained at precise concentrations[18,19]. Second, cell-free systems bypass viability constraints making possible the production of proteins at titers that would otherwise be toxic in living cells[20]. Third, processes that take days or weeks to design, prepare, and execute in vivo can be done more rapidly in a cell-free system[21,22], leading to high-throughput production campaigns on a whole-proteome scale[23] with the ability to automate[24].

Unfortunately, CFPS systems have been limited by their inability to co-activate efficient protein synthesis and glycosylation. The best characterized and most widely adopted CFPS systems use *E. coli* lysates to activate in vitro protein synthesis, but these systems are incapable of making glycoproteins because *E. coli* lacks endogenous glycosylation machinery. Glycosylation is possible in some eukaryotic CFPS systems, including those prepared from insect cells[25], trypanosomes[26], hybridomas[27], or mammalian cells[28, 29]. However, these platforms are limited to endogenous machinery for performing glycosylation, meaning that (i) the possible glycan structures are restricted to those naturally synthesized by the host cells and (ii) the glycosylation process is carried out in a black box and thus difficult to engineer or control. Additionally, eukaryotic CFPS systems are technically difficult to prepare, often requiring supplementation with microsomes[30, 31], and suffer from inefficient protein synthesis and glycosylation yields due to inefficient trafficking of nascent polypeptide chains to microsomes[26, 31].

Despite progress in eukaryotic cell-free systems, cell-free extracts from bacteria like *E. coli* offer a blank canvas for studying glycosylation pathways, provided they can be activated in vitro. A recent work from our group highlights the ability of CFPS to enable glycoprotein synthesis in bacterial cell-free systems by augmenting commercial *E. coli*-based cell-free translation systems with purified components from a bacterial N-linked glycosylation pathway[32]. While these results established the possibility of *E. coli* lysate-based glycoprotein production, there are several drawbacks of using purified glycosylation components that limit system utility. First, preparation of the glycosylation components required time-consuming and cost-prohibitive steps, namely purification of a multipass transmembrane oligosaccharyltransferase (OST) enzyme and organic solvent-based extraction of lipid-linked oligosaccharide (LLO) donors from bacterial membranes. These steps significantly lengthen the process development timeline, requiring 3-5 days each for preparation of the LLO and OST components, necessitate skilled operators and specialized equipment, and result in products that must be refrigerated and are stable for only a few months to a year. Second, glycoproteins were produced using a sequential translation/glycosylation strategy, which required 20 h for cell-free synthesis of the glycoprotein target and an additional 12 h for post-translational protein glycosylation.

Here, we addressed these drawbacks by developing an integrated cell-free glycoprotein synthesis (CFGpS) technology that bypasses the need for purification of OSTs and organic solvent-based extraction of LLOs. The creation of this streamlined CFGpS system was made possible by two important discoveries: (i) crude extract prepared from the glyco-optimized *E. coli* strain, CLM24, is able to support cell-free protein expression and N-linked glycosylation; and (ii) OST- and LLO-enriched extracts derived from CLM24 are able to reproducibly co-activate protein synthesis and N-glycosylation in a reaction mixture that minimally requires priming with DNA encoding the target glycoprotein of interest. Importantly, the CFGpS system decouples production of glycoprotein synthesis components (i.e., OSTs, LLOs, translational machinery) and the glycoprotein target of interest, providing significantly reduced cell viability constraints compared to in vivo systems. The net result is a one-pot bacterial glycoprotein biosynthesis platform whereby different acceptor proteins, OSTs, and/or oligosaccharide structures can be functionally interchanged and prototyped for customizable glycosylation.

Results

Figure 9:
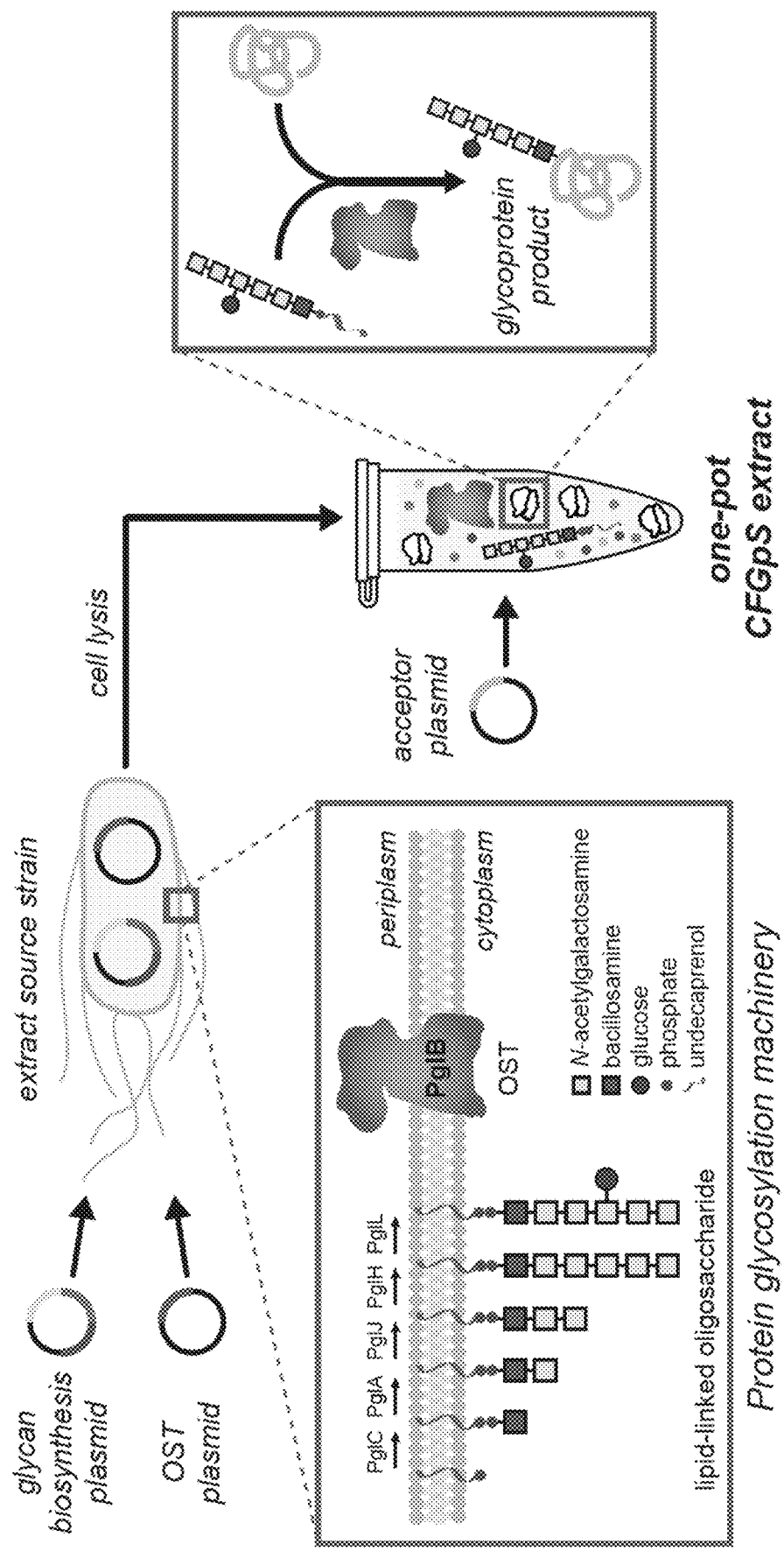
FIG. 9. Schematic of single-pot CFGpS technology. Glyco-engineered *E. coli* that are modified with (i) genomic mutations that benefit glycosylation reactions and (ii) plasmid DNA for producing essential glycosylation components (i.e., OSTs, LLOs) serve as the source strain for producing crude S30 extracts. Candidate glycosylation components can be derived from all kingdoms of life, including bacteria, and include single-subunit OSTs like *C. jejuni* PglB and LLOs bearing N-glycans from *C. jejuni* that are assembled on Und-PP by the Pgl pathway enzymes. Following extract preparation by lysis of the source strain, one-pot biosynthesis of N-glycoproteins is initiated by priming the extract with DNA encoding the acceptor protein target of interest.

Efficient CFGpS using extracts from glyco-optimized chassis strain. To develop a one-pot glycoprotein synthesis system, the bacterial protein glycosylation locus (pgl) present in the genome of the Gram-negative bacterium *Campylobacter jejuni* was chosen as a model glycosylation system (FIG. 9). This gene cluster encodes an asparagine-linked (N-linked) glycosylation pathway that is functionally similar to that of eukaryotes and archaea[33], involving a single-subunit OST, PglB, that catalyzes the en bloc transfer of a preassembled 1.4 kDa GlcGalNAc5Bac heptasaccharide (where Bac is bacillosamine) from the lipid carrier undecaprenyl pyrophosphate (Und-PP) onto asparagine residues in a conserved motif (D/E-$X_{-1}$-N-$X_{+1}$-S/T, where $X_{-1}$ and $X_{+1}$ are any residues except proline) within acceptor proteins. PglB was selected because we previously showed that N-glycosylated acceptor proteins were reliably produced when cell-free translation kits were supplemented with (i) *C. jejuni* PglB (CjPglB) purified from *E. coli* cells and (ii) LLOs extracted from glycoengineered *E. coli* cells expressing the enzymes for producing the *C. jejuni* N-glycan on Und-PP (CjLLOs)[32]. Additionally, PglB has been used in engineered *E. coli* for transferring eukaryotic trimannosyl chitobiose glycans (mannose$_3$-N-acetylglucosamine$_2$, Man$_3$GlcNAc$_2$) to specific asparagine residues in target proteins[12].

Establishing a CFGpS system first required crude cell extracts suitable for glycoprotein synthesis; hence, we selected *E. coli* strain CLM24 that was previously optimized for in vivo protein glycosylation[34]. CLM24 has two attributes that we hypothesized would positively affect cell-free protein glycosylation. First, CLM24 does not synthesize O-polysaccharide antigen due to an inactivating insertion in wbbL, which encodes a rhamnosyl transferase that transfers the second sugar of the O16 subunit to UndPP[35]. Thus, absence of WbbL should allow uninterrupted assembly of engineered glycans, such as the *C. jejuni* heptasaccharide, on UndPP. Second, CLM24 cells lack the waaL gene, which encodes the ligase that transfers O-polysaccharide antigens from UndPP to lipid A-core. Because WaaL can also promiscuously transfer engineered glycans that are assembled on UndPP[12, 36], the absence of this enzyme should favor accumulation of target glycans on UndPP.

Figure 10:
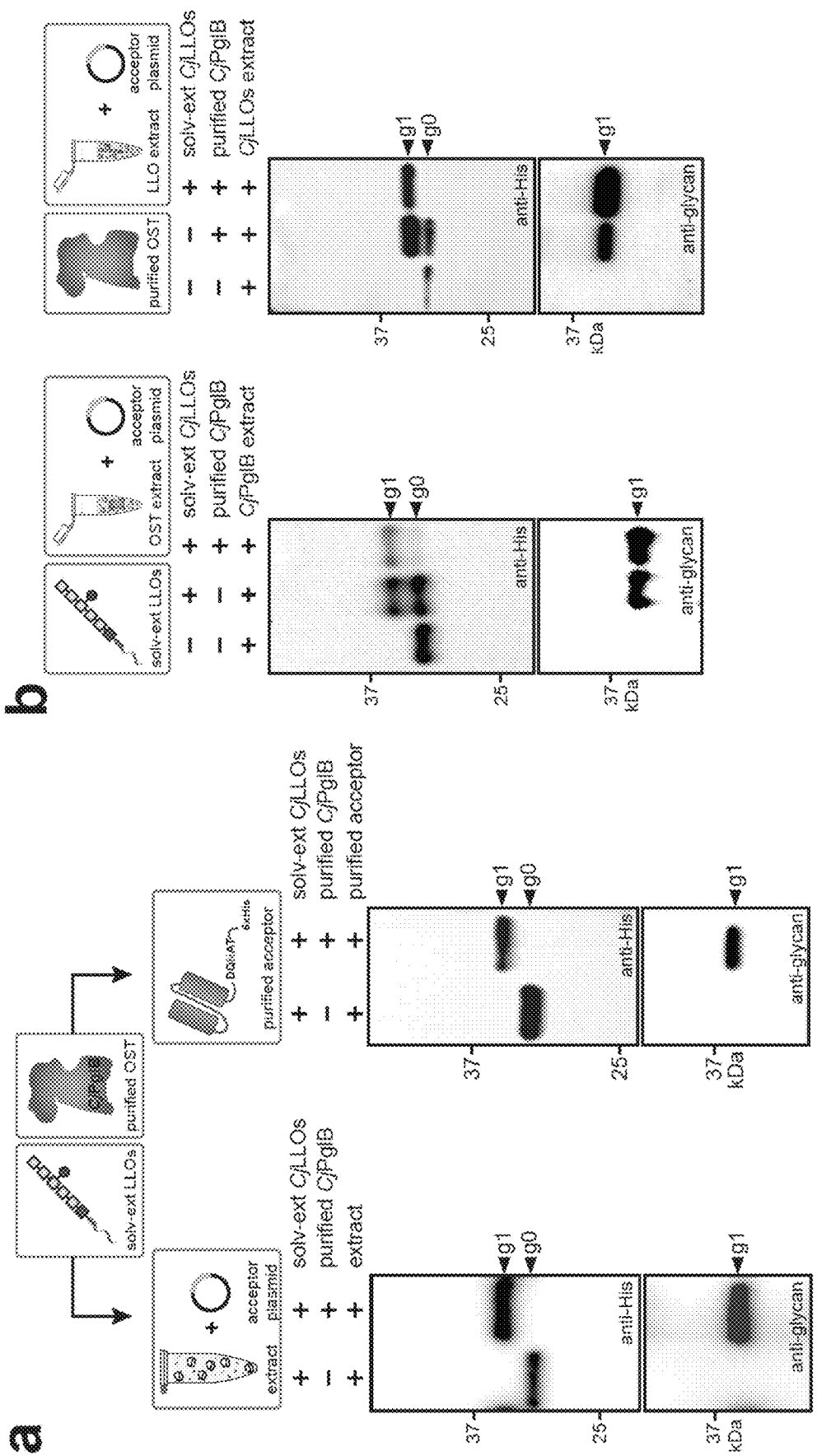
FIG. 10. Extract from glyco-optimized chassis strain supports CFGpS. (a) (left) Western blot analysis of scFv13-R4$^{DQNAT}$ produced by crude CLM24 extract supplemented with purified CjPglB and organic solvent-extracted (solv-ext) CjLLOs, and primed with plasmid pJL1-scFv13-R4$^{DQNAT}$. (right) Western blot analysis of in vitro glycosylation reaction using purified scFv13-R4$^{DQNAT}$ acceptor protein that was incubated with purified CjPglB and organic solvent-extracted (solv-ext) CjLLOs. Control reactions (lane 1 in each panel) were performed by omitting purified CjPglB. (b) (left) Western blot analysis of scFv13-R4$^{DQNAT}$ produced by crude CLM24 extract selectively enriched with CjPglB from heterologous overexpression from pSF-CjPglB. (right) Western blot analysis of scFv13-R4$^{DQNAT}$ produced by crude CLM24 extract selectively enriched with CjLLOs from heterologous overexpression from pMW07-pglΔB. Reactions were primed with plasmid pJL1-scFv13-R4$^{DQNAT}$ and supplemented with purified CjPglB and organic solvent-extracted (solv-ext) CjLLOs as indicated. Control reactions (lane 1 in each panel) were performed by omitting solv-ext CjLLOs in (left) or purified CjPglB (right) in (b). Blots were probed with anti-hexa-histidine antibody (anti-His) to detect the acceptor protein or hR6 serum (anti-glycan) to detect the N-glycan. Arrows denote aglycosylated (g0) and singly glycosylated (g1) forms of scFv13-R4$^{DQNAT}$. Molecular weight (MW) markers are indicated at left. Results are representative of at least three biological replicates.

To determine whether CLM24 could be used as a chassis strain to support integrated cell-free transcription, translation, and glycosylation, we first prepared crude S30 extract from these cells using a rapid and robust procedure for extract preparation based on sonication[37]. Then, 15-µL batch-mode, sequential CFGpS reactions were performed using CLM24 crude extract that was supplemented with the following: (i) an OST catalyst in the form of purified CjPglB that was prepared as described previously[32]; (ii) oligosaccharide donor in the form of CjLLOs that were isolated by organic solvent extraction from the membrane fraction of glycoengineered *E. coli* cells as described previously[32]; and (iii) plasmid DNA encoding the model acceptor protein scFv13-R4$^{DQNAT}$, an anti-β-galactosidase (β-gal) single-chain variable fragment (scFv) antibody modified C-terminally with a single DQNAT motif[12]. The glycosylation status of scFv13-R4$^{DQNAT}$ was analyzed by SDS-PAGE and immunoblotting with an anti-polyhistidine (anti-His) antibody or hR6 serum that is specific for the *C. jejuni* heptasaccharide glycan[38]. Following an overnight reaction at 30° C., highly efficient glycosylation was achieved as evidenced by the mobility shift of scFv13-R4$^{DQNAT}$ entirely to the monoglycosylated (g1) form in anti-His immunoblots and the detection of the *C. jejuni* glycan attached to scFv13-R4$^{DQNAT}$ by hR6 serum (FIG. 10a). For synthesis of scFv13-R4$^{DQNAT}$, the reaction mixture was modified to be oxidizing, through the addition of iodoacetamide and a 3:1 ratio of oxidized and reduced glutathione, demonstrating the flexibility of CFGpS reaction conditions for producing eukaryotic glycoprotein targets. The efficiency achieved in this CFGpS system rivaled that of an in vitro glycosylation reaction in which the scFv13-R4$^{DQNAT}$ acceptor protein was expressed and purified from *E. coli*, and then incubated overnight with purified CjPglB and extracted CjLLOs (FIG. 10a). As expected, when CjPglB was omitted from the reaction, the scFv13-R4$^{DQNAT}$ acceptor protein was produced only in the aglycosylated (g0) form. The results generated here with CLM24 extract are consistent with our earlier studies using an *E. coli* S30 extract-based CFPS system or purified translation machinery[32], and establish that the *C. jejuni* N-linked protein glycosylation mechanism can be functionally reconstituted outside the cell.

Figure 11:
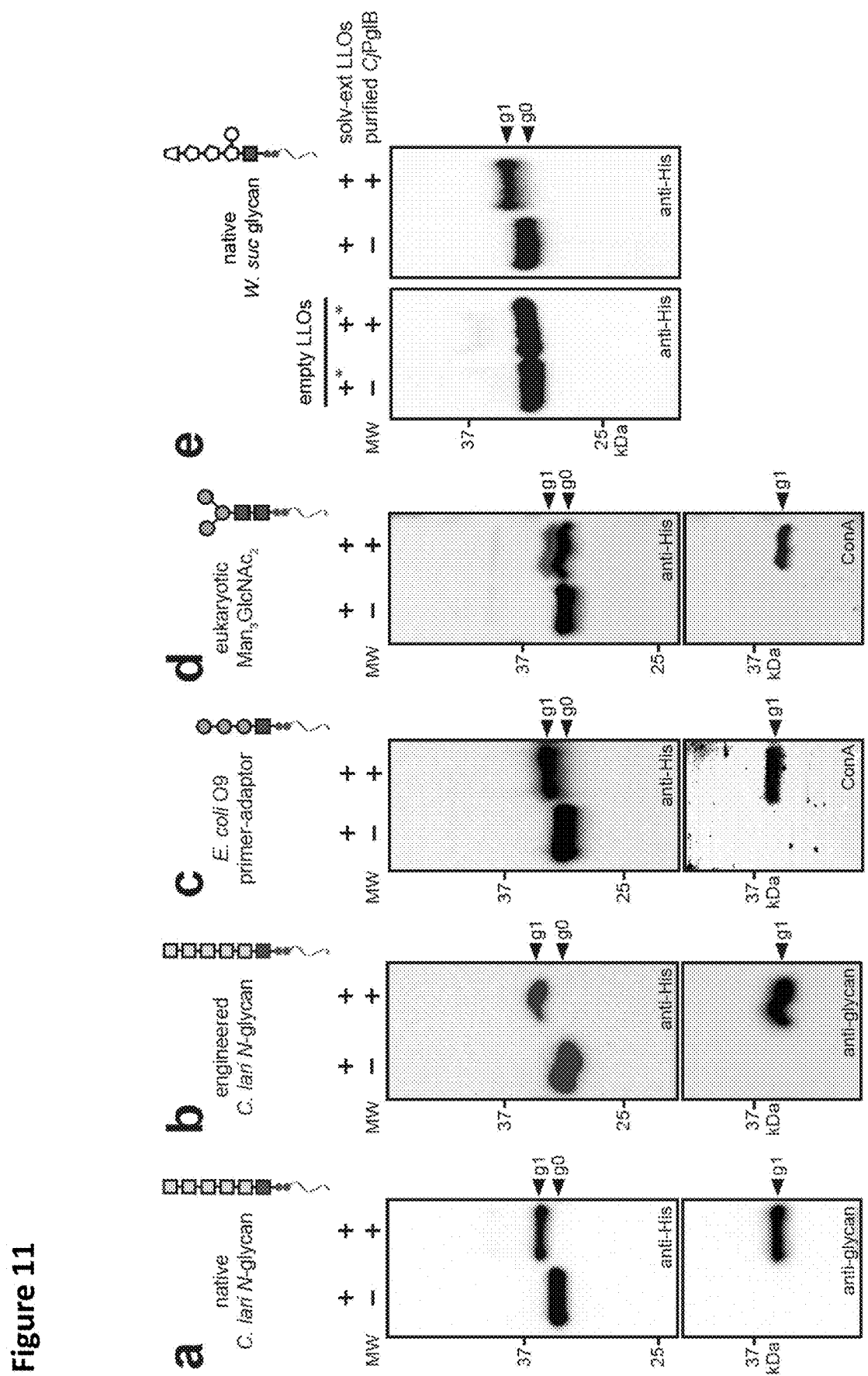
FIG. 11. Expanding cell-free glycosylation with different oligosaccharide structures. Western blot analysis of in vitro glycosylation reaction products generated with purified scFv13-R4$^{DQNAT}$ acceptor protein, purified CjPglB, and organic solvent-extracted (solv-ext) LLOs from cells carrying: (a) plasmid pACYCpgl4 for making the native *C. lari* hexasaccharide N-glycan; (b) plasmid pACYCpgl2 for making the engineered *C. lari* hexasaccharide N-glycan; (c) plasmid pO9-PA for making the *E. coli* O9 'primer-adaptor' Man$_3$GlcNAc structure; (d) plasmid pConYCGmCB for making the eukaryotic Man$_3$GlcNAc$_2$ N-glycan structure; and (e) fosmid pEpiFOS-5pgl5 for making the native *W. succinogenes* hexasaccharide N-glycan. Reactions were run at 30° C. for 16 h. Blots were probed with anti-His antibody to detect the acceptor protein and one of the following: hR6 serum that cross-reacts with the native and engineered *C. lari* glycans or ConA lectin that binds internal and non-reducing terminal α-mannosyl groups in the Man$_3$GlcNAc and Man$_3$GlcNAc$_2$ glycans. Because structural determination of the *W. succinogenes* N-glycan is currently incomplete, and because there are no available antibodies, the protein product bearing this N-glycan was only probed with the anti-His antibody. As an additional control for this glycan, we included empty LLOs prepared from the same host strain but lacking the pEpiFOS-5pgl5 fosmid (left hand panel, "+" signs marked with an asterisk). Arrows denote aglycosylated (g0) and singly glycosylated (g1) forms of the scFv13-R4$^{DQNAT}$ protein. Molecular weight (MW) markers are indicated at left. Results are representative of at least three biological replicates.
Figure 14:
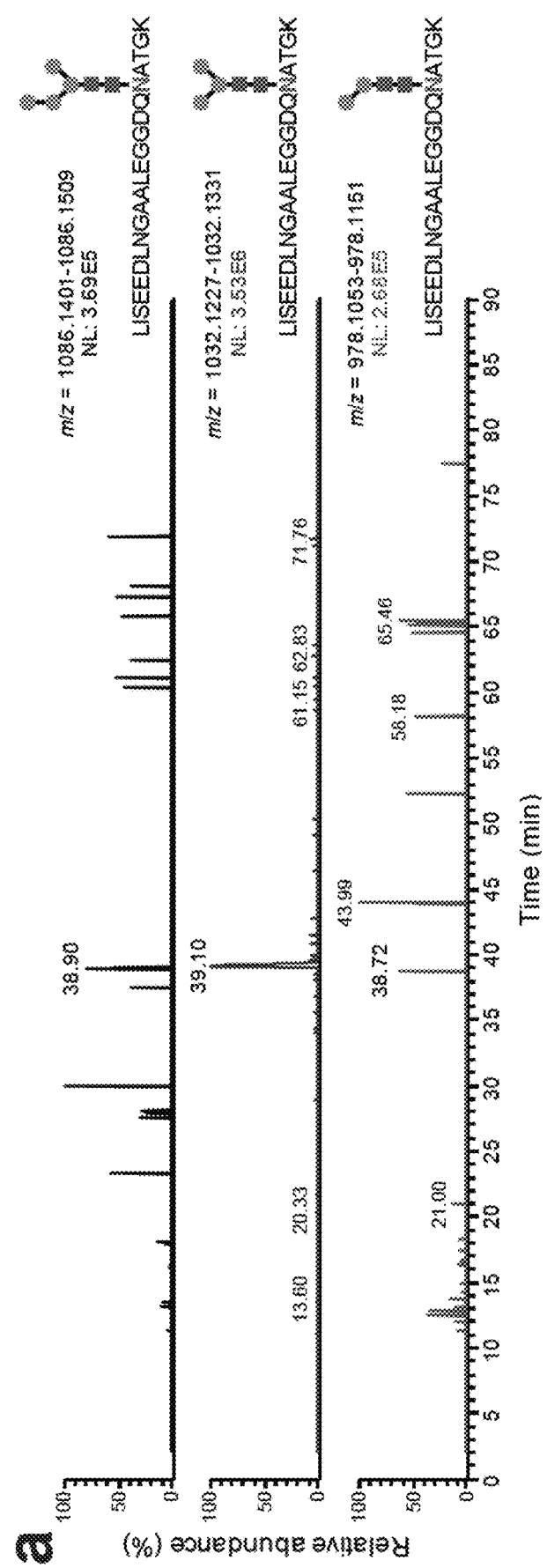
FIG. 14. MS analysis of scFv13-R4DQNAT glycosylated with Man3GlcNAc2. Ni-NTA-purified scFv13-R4DQNAT was subjected to in vitro glycosylation in the presence of purified CjPglB and organic solvent-extracted Man3GlcNAc2 LLOs, and then directly loaded into an SDS-PAGE gel. Following staining of gel with Coomassie Brilliant Blue G-250 (inset), the glycosylated band (lane 2, indicated by box) was excised and submitted for MS analysis. LISEEDLNGAALEGGDQNATGK (SEQ ID NO:10). Controls included in vitro glycosylation reaction performed with solvent-extracted empty LLOs (lane 1) and complete in vitro glycosylation reaction mixture lacking purified scFv13-R4DQNAT acceptor protein (lane 3). Molecular weight (MW) ladder loaded on the left. (a) Three extracted ion chromatograms (XIC) corresponding to mass ranges for three possible glycopeptide products having masses consistent with the expected Man3GlcNAc2 (middle), as well as Man4GlcNAc2 (top) and Man2GlcNAc2 (bottom) attached to N273 site of scFv13-R4DQNAT (mass tolerance at 5 ppm). The individually normalized level (NL) for each glycoform indicates that only a Hex3HexNAc2 glycoform, which eluted at 39.10 min with NL of 3.53E6, was decently detected in the sample (middle). A trace amount of a Hex4HexNAc2 glycoform form eluted at 38.9 min with NL of 2.96E5 (top), but no Hex2HexNAc2 glycoform was detected. (b) MS spectrum of the detected glycopeptide containing an N-linked pentasaccharide consistent with Man3GlcNAc2 at m/z=1032.4583. The MS inset shows an expanded view of the glycopeptide ion with triple charge.
Figure 14:
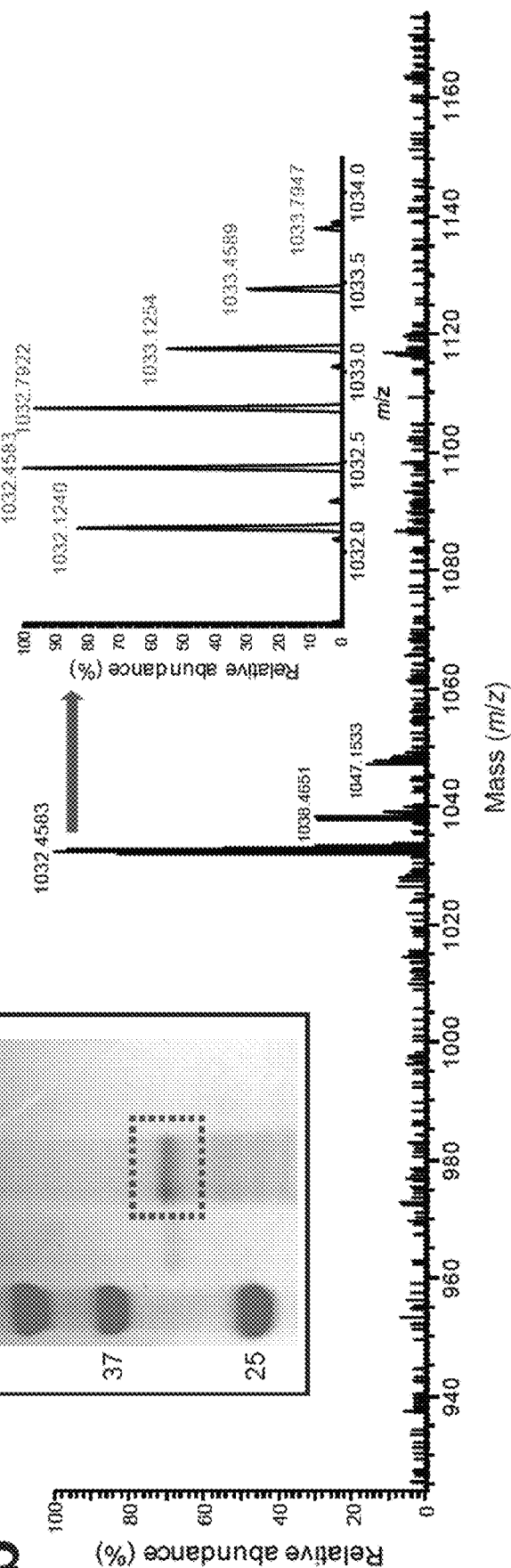
Figure 15:
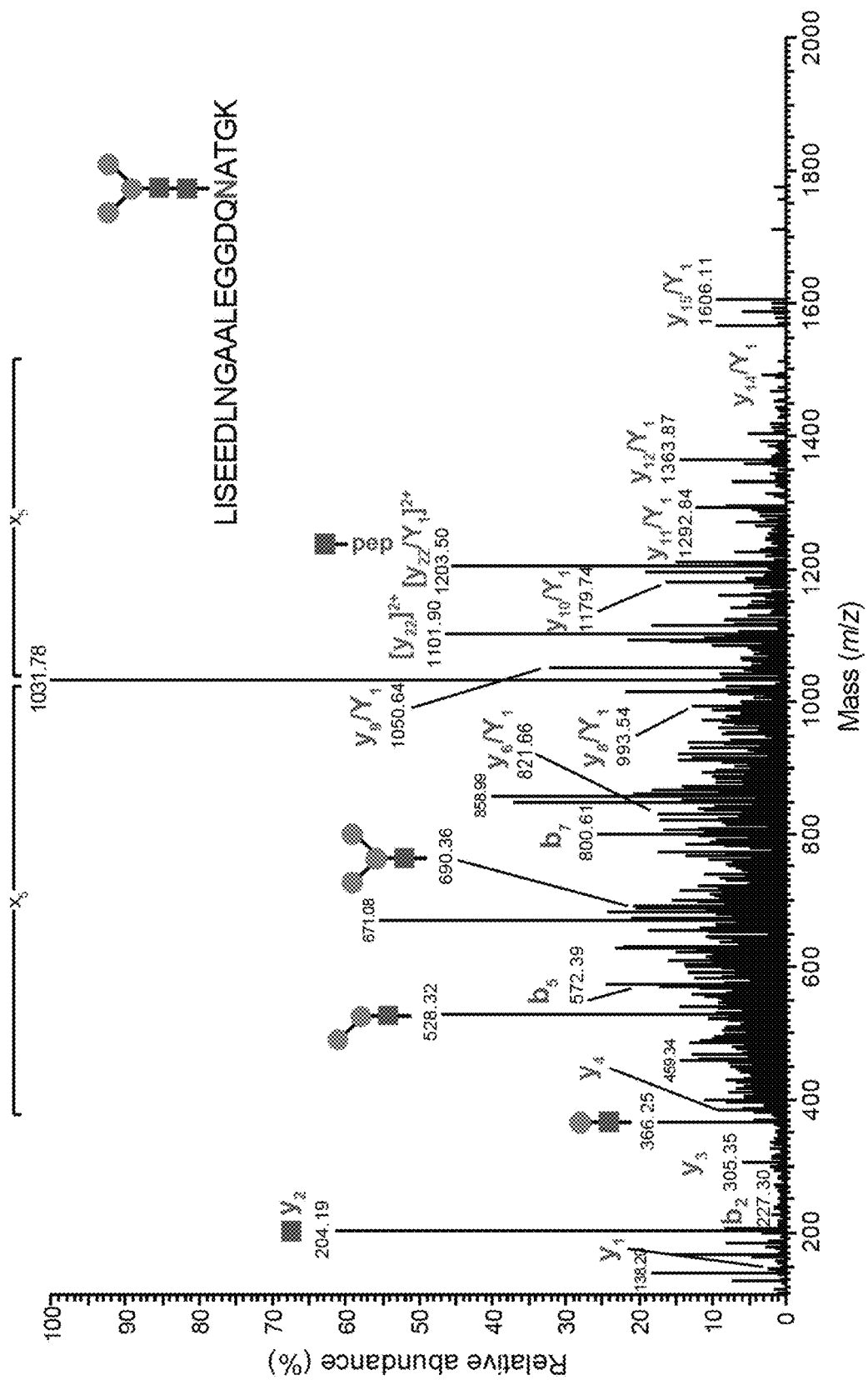
FIG. 15. Tandem mass spectrometry of scFv13-R4DQNAT glycosylated with Man3GlcNAc2. MS/MS spectrum of the triply-charged precursor (m/z 1032.12), identifying the glycopeptide with core pentasaccharide (Hex3HexNAc2) attached to residue N273 (illustrated) in scFv13-R4DQNAT. A series of y-ions covering from y1 to y4 and a second series of yions with the added mass of 203.08 Da at N273 site were found covering from y6/Y1 to y15/Y1, leading to the confident identification of tryptic peptide 256-LISEEDLNGAALEGGDQNATGK-277 (SEQ ID NO:10) and providing direct evidence for HexNAc as the innermost monosaccharide (Y1) attached to the N273 site. This result is also consistent with the previous observation that a relatively tight bond exists for the Y1-peptide compared to the fragile internal glycan bonds.

Expanding the glycan repertoire of cell-free glycosylation. To date, only the *C. jejuni* glycosylation pathway has been reconstituted in vitro[32], and it remains an open question whether our system can be reconfigured with different LLOs and OSTs. Therefore, to extend the range of glycan structures beyond the *C. jejuni* heptasaccharide, we performed glycosylation reactions in which the solvent-extracted CjLLOs used above were replaced with oligosaccharide donors extracted from *E. coli* cells carrying alternative glycan biosynthesis pathways. These included LLOs bearing the following glycan structures: (i) native *C. lari* hexasaccharide N-glycan[38]; (ii) engineered GalNAc$_5$GlcNAc based on the *Campylobacter lari* hexasaccharide N-glycan[39]; (iii) native *Wolinella succinogenes* hexasaccharide N-glycan containing three 216-Da monosaccharides and an unusual 232-Da residue at the nonreducing end[40]; (iv) engineered *E. coli* O9 primer-adaptor glycan, Man$_3$GlcNAc, that links the O-chain and core oligosaccharide in the lipopolysaccharide of several *E. coli* and *Klebsiella pneumoniae* serotypes[41]; and (v) eukaryotic trimannosyl core N-glycan, Man$_3$GlcNAc$_2$[12]. Glycosylation of scFv13-R4$^{DQNAT}$ with each of these different glycans was observed to occur only in the presence of CjPglB (FIG. 11). It should be noted that 100% glycosylation conversion was observed for each of these glycans except for the Man$_3$GlcNAc$_2$ N-glycan, which had a conversion of ~40% as determined by densitometry analysis. While the reasons for this lower efficiency remain unclear, conjugation efficiency of the same Man$_3$GlcNAc$_2$ glycan to acceptor proteins in vivo was reported to be even lower (<5%)[12, 42]. Hence, transfer of Man$_3$GlcNAc$_2$ to acceptor proteins in vitro appears to overcome some of the yet-to-be-identified bottlenecks of in vivo glycosylation. This result is likely due to the opportunity with CFGpS to control the concentration of reaction components, for example, providing a higher local concentration of LLO donors. Importantly, scFv13-R4$^{DQNAT}$ was uniformly decorated with a Man$_3$GlcNAc$_2$ glycan as evidenced by liquid chromatography-mass spectrometry (LC-MS). Specifically, the only major glycopeptide product to be detected was a triply-charged ion containing an N-linked pentasaccharide with m/z=1032.4583, consistent with the Man$_3$GlcNAc$_2$ glycoform (FIG. 14). The tandem MS spectra for this triply-charged glycopeptide yielded an excellent y-ion series and a good b-ion series enabling conclusive determination of the tryptic glycopeptide sequence and attachment of the Man$_3$GlcNAc$_2$ glycoform at residue N273 of the scFv13-R4$^{DQNAT}$ protein (FIG. 15). Taken together, these results demonstrate that structurally diverse glycans, including those that resemble eukaryotic structures, can be modularly interchanged in cell-free glycosylation reactions.

Extracts enriched with OST enzymes or LLOs co-activate glycosylation. To circumvent the need for exogenous addition of purified glycosylation components, we hypothesized that heterologous overexpression of OST or GT enzymes directly in the chassis strain would yield extracts that are selectively enriched with the requisite glycosylation components. This strategy was motivated by a recent metabolic engineering approach whereby multiple cell-free lysates were each selectively enriched with an overexpressed metabolic enzyme and then combinatorially mixed to construct an intact pathway[19, 21]. However, a fundamental difference in our system is the fact that the OST and LLOs are not soluble components but instead reside natively in the inner cytoplasmic membrane. This is potentially problematic because of the significant breakup of the cell membrane during S30 extract preparation. However, it has been established that fragments of the *E. coli* inner membrane reform into membrane vesicles, some of which are inverted but others that are orientated properly[43], and thus could supply the OST and LLOs in a functionally accessible conformation within the extract.

Figure 16:
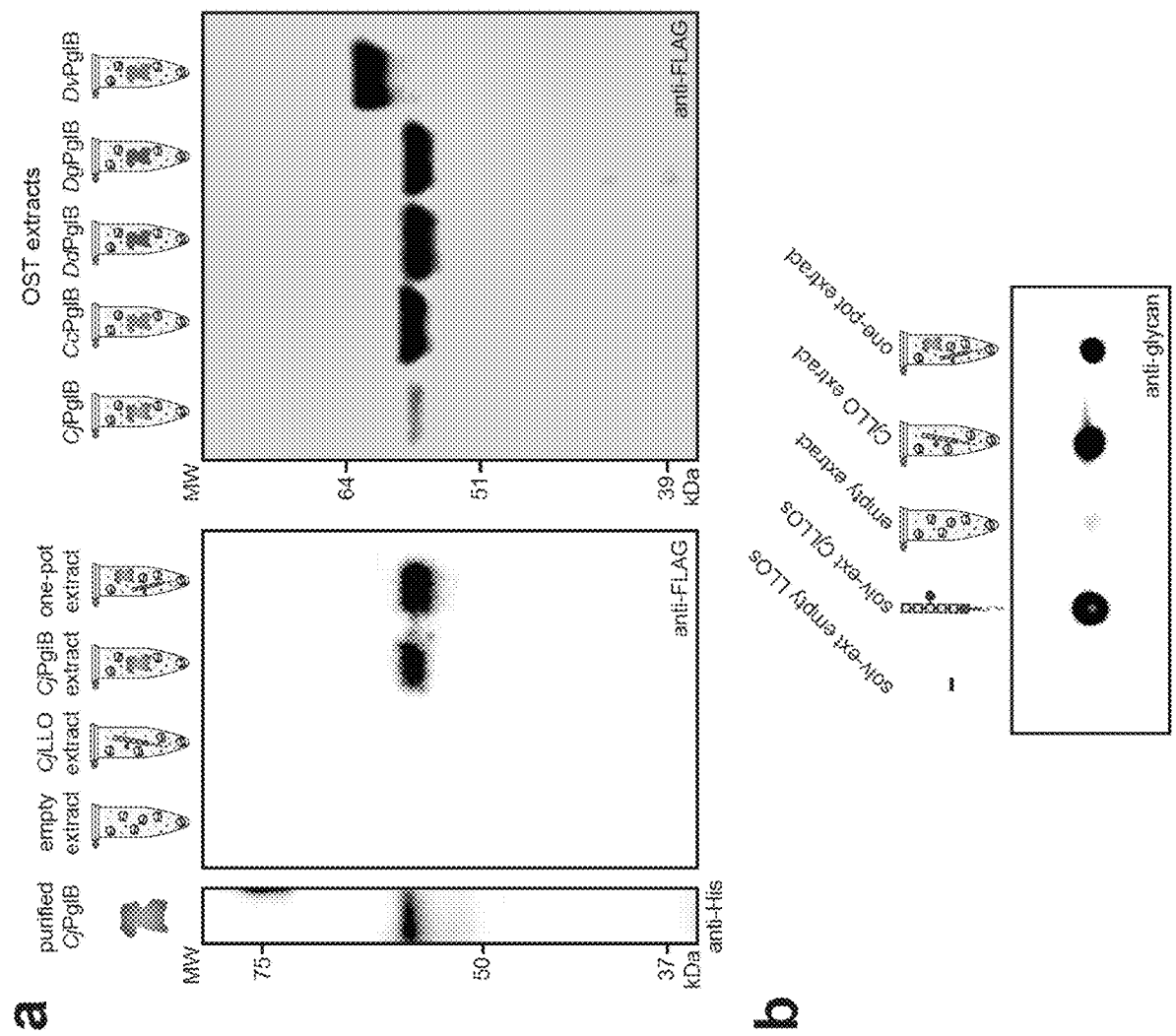
FIG. 16. Crude cell extracts are enriched with glycosylation machinery. (a) Western blot analysis of CjPglB in the following samples: (left-hand panel) 1 μg of purified CjPglB; (center panel) crude cell extracts derived from CLM24 cells with no plasmid (empty extract), CLM24 cells carrying pMW07-pgl B (CjLLO extract), CLM24 cells carrying pSF-CjPglB (CjPglB extract) or CLM24 cells carrying pMW07-pgl B and pSF-CjPglB (one-pot extract); and (right-hand panel) crude cell extracts derived from CLM24 cells carrying pSF-based plasmids encoding different PglB homologs as indicated. Blots were probed with anti-His antibody and anti-FLAG antibody as indicated. Molecular weight (MW) markers are indicated at left. Results are representative of at least three biological replicates. (b) Dot blot analysis of LLOs in the following samples: organic solvent extract from membrane fractions of CLM24 cells with no plasmid (solv-ext empty LLOs) or from CLM24 cells carrying plasmid pMW07-pgl B (solv-ext CjLLOs); crude cell extracts derived from CLM24 cells with no plasmid (empty extract), CLM24 cells carrying pMW07-pgl B (CjLLO extract) or CLM24 cells carrying pMW07-pgl B and pSF-CjPglB (one-pot extract). 10 μl of extracted LLOs or crude cell extract was spotted onto nitrocellulose membrane and probed with hR6 serum (anti-glycan).

To test this hypothesis, we used a high-pressure homogenization method to prepare crude S30 extract from CLM24 cells carrying a plasmid-encoded copy of CjPglB such that the resulting cell-free lysates were selectively enriched with detectable quantities of full-length OST enzyme as confirmed by Western blot analysis (FIG. 16a). Similarly, crude S30 extract from CLM24 cells overexpressing the *C. jejuni* glycan biosynthesis enzymes produced lysate that was selectively enriched with CjLLOs as confirmed by dot blot analysis with hR6 serum (FIG. 16b). It should be noted that the amount of CjLLOs enriched in the crude extract rivaled that produced by the significantly more tedious organic solvent extraction method. Importantly, when 15-μL batch-mode sequential CFGpS reactions were performed using the OST-enriched crude extract that was supplemented with solvent extracted CjLLOs and plasmid DNA encoding scFv13-R4$^{DQNAT}$, clearly detectable glycosylation of the acceptor protein was observed (FIG. 10b). The conversion of acceptor protein to glycosylated product was ~50%; however, further supplementation with purified CjPglB increased the conversion to nearly 100%, indicating that the amount of OST in the crude extract might have been limiting under the conditions tested. When similar CFGpS reactions were performed using the CjLLOs-enriched crude extract supplemented with purified CjPglB and plasmid DNA encoding scFv13-R4$^{DQNAT}$, >80% glycosylation of the acceptor protein was observed, which reached 100% when additional donor glycans were supplemented (FIG. 10b).

Figure 12:
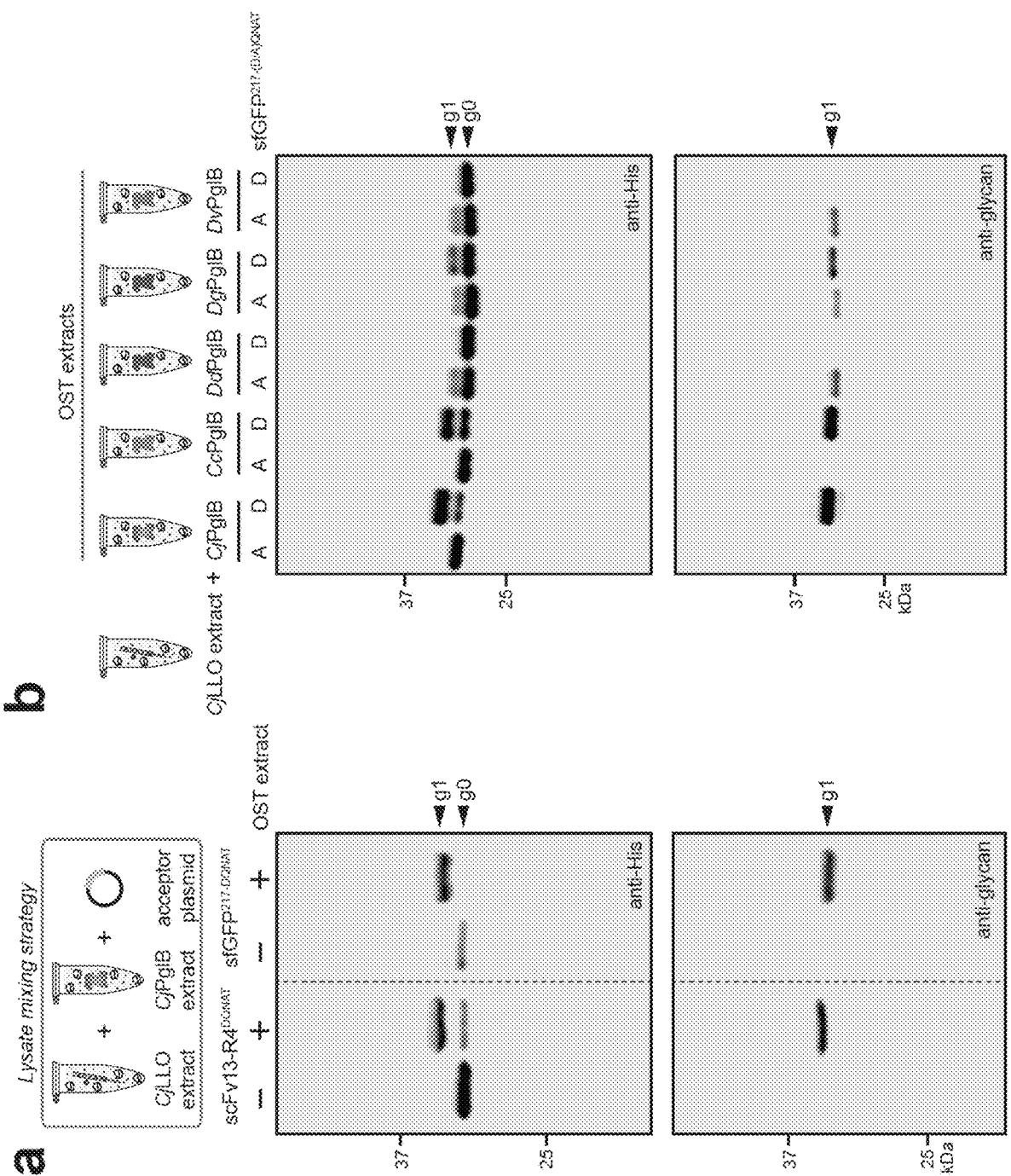
FIG. 12. Mixing of CFGpS extracts enables rapid prototyping of different OST enzymes. (a) Western blot analysis of CFGpS reactions performed using lysate mixing strategy whereby CjLLO lysate derived from CLM24 cells carrying pMW07-pglΔB was mixed with CjPglB lysate derived from CLM24 cells carrying pSF-CjPglB, and the resulting CFGpS mixture was primed with plasmid DNA encoding either scFv13-R4$^{DQNAT}$ or sfGFP$^{217\text{-}DQNAT}$ (b) Western blot analysis of CFGpS reactions performed using CjLLO lysate mixed with extract derived from CLM24 cells carrying a pSF plasmid encoding one of the following OSTs: CjPglB, CcPglB, DdPglB, DgPglB, or DvPglB. Mixed lysates were primed with plasmid DNA encoding either sfGFP$^{217\text{-}DQNAT}$ (D) or sfGFP$^{217\text{-}AQNAT}$ (A). Blots were probed with anti-His antibody to detect the acceptor proteins (top panels) and hR6 serum against the *C. jejuni* glycan (bottom panels). Arrows denote aglycosylated (g0) and singly glycosylated (g1) forms of the acceptor proteins. Molecular weight (MW) markers are indicated at left. Results are representative of at least three biological replicates.

CFGpS modularity enables glycosylation components to be rapidly interchanged. Given the open nature of cell-free biosynthesis, we postulated that it should be possible to functionally interchange and prototype alternative biochemical reaction components. One straightforward way that this can be accomplished is by combining separately prepared extracts, each of which is selectively enriched with a given enzyme, such that the resulting reaction mixture comprises a functional biological pathway[19, 21]. As proof of this concept, separately prepared CjLLO and CjPglB extracts were mixed and subsequently primed with DNA encoding the scFv13-R4$^{DQNAT}$ acceptor. The resulting mixture promoted efficient glycosylation of scFv13-R4$^{DQNAT}$ as observed in Western blots probed with anti-His antibody and hR6 serum (FIG. 12a). In addition to scFv13-R4$^{DQNAT}$, we also expressed a different model acceptor protein that was created by grafting a 21-amino acid sequence from the *C. jejuni* glycoprotein AcrA[32], which was further modified with an optimized DQNAT glycosylation site, into a flexible loop of superfolder GFP (sfGFP$^{217-DQNAT}$). The mixed lysate reaction scheme was able to glycosylate the sfGFP$^{217-DQNAT}$ acceptor protein with 100% conversion (FIG. 12a). It is noteworthy that the high conversion observed for both acceptor proteins was achieved in mixed lysates without the need to supplement the reactions with purified OST or organic solvent-extracted CjLLOs.

Next, we sought to demonstrate that the mixed lysate approach could be used to rapidly prototype the activity of four additional bacterial OSTs. Crude extracts were separately prepared from CLM24 source strains heterologously overexpressing one of the following bacterial OSTs: *Campylobacter coli* PglB (CcPglB), *Desulfovibrio desulfuricans* PglB (DdPglB), *Desulfovibrio gigas* PglB (DgPglB), or *Desulfovibrio vulgaris* PglB (DvPglB). The resulting extracts were selectively enriched with full-length OST proteins at levels that were comparable to CjPglB (FIG. 16a). Each OST extract was mixed with the CjLLO-enriched extract and then supplemented with plasmid DNA encoding sfGFP$^{217-DQNAT}$ or a modified version of this target protein where the residue in the −2 position of the acceptor sequon was mutated to alanine. Upon completion of CFGpS reactions, the expression and glycosylation status of sfGFP$^{217-DQNAT}$ and sfGFP$^{217-AQNAT}$ was followed by Western blot analysis, which revealed information about the sequon preferences for these homologous enzymes. For example, the mixed lysate containing CcPglB was observed to efficiently glycosylate sfGFP$^{217-DQNAT}$ but not sfGFP$^{217-AQNAT}$ (FIG. 12b). This activity profile for CcPglB was identical to that observed for CjPglB, which was not surprising based on its high sequence similarity (~81%) to CjPglB. In contrast, lysate mixtures containing OSTs from *Desulfovibrio* sp., which have low sequence identity (~15-20%) to CjPglB, showed more relaxed sequon preferences (FIG. 12b). Specifically, DgPglB-enriched extract mixtures modified both (D/A)QNAT motifs with nearly equal efficiency while mixed lysates containing DdOST and DvOST preferentially glycosylated the AQNAT (SEQ ID NO:5) sequon.

Figure 13:
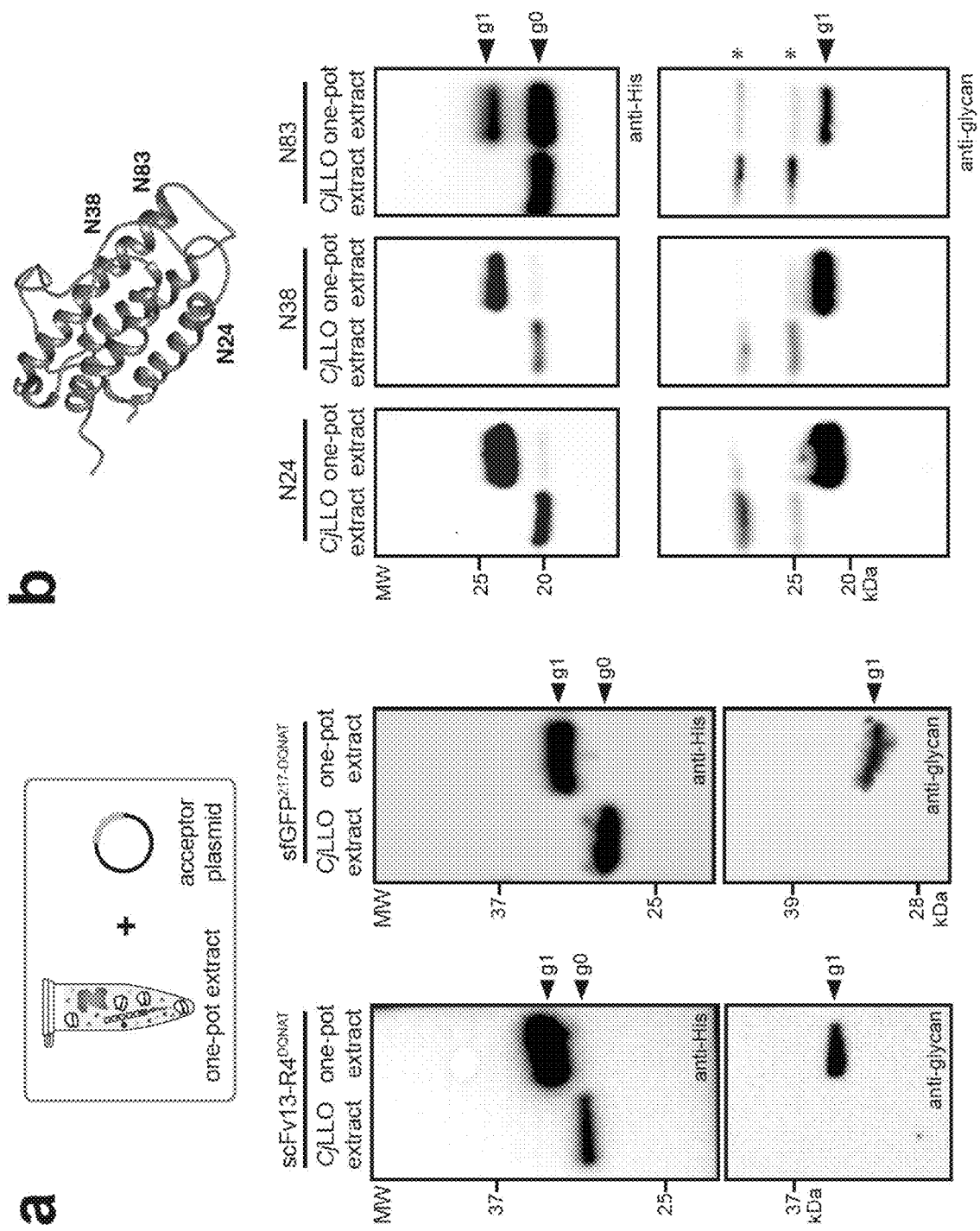
FIG. 13. One-pot CFGpS using extracts selectively enriched with OSTs and LLOs. (a) Western blot analysis of scFv13-R4$^{DQNAT}$ or sfGFP$^{217\text{-}DQNAT}$ produced by crude CLM24 extract selectively enriched with (i) CjPglB from heterologous overexpression from pSF-CjPglB and (ii) CjLLOs from heterologous overexpression from pMW07-pglΔB. Reactions were primed with plasmid pJL1-scFv13-R4$^{DQNAT}$ or pJL1-sfGFP$^{217\text{-}DQNAT}$ (b) Ribbon representation of human erythropoietin (PDB code 1BUY) with α-helices and flexible loops illustrated. Glycosylation sites modeled by mutating the native sequons at N24 (22-AENIT-26) (SEQ ID NO:7), N38 (36-NENIT-40) (SEQ ID NO:8) or N83 (81-LVNSS-85) (SEQ ID NO:9) to DQNAT (SEQ ID NO:6), with asparagine residues in each sequon indicated. Image prepared using UCSF Chimera package.[67] Glycoengineered hEPO variants in which the native sequons at N24 (22-AENIT-26) (SEQ ID NO:7), N38 (36-NENIT-40) (SEQ ID NO:8) or N83 (81-LVNSS-85) (SEQ ID NO:9) were individually mutated to an optimal bacterial sequon, DQNAT (SEQ ID NO:6) (illustrated). Western blot analysis of hEPO glycovariants produced by crude CLM24 extract selectively enriched with (i) CjPglB from heterologous overexpression from pSF-CjPglB and (ii) CjLLOs from heterologous overexpression from pMW07-pglΔB. Reactions were primed with plasmid pJL1-hEPO$^{22\text{-}DQNAT\text{-}26}$ (N24), pJL1-hEPO$^{36\text{-}DQNAT\text{-}40}$ (N38), or pJL1-hEPO$^{81\text{-}DQNAT\text{-}85}$ (N83) as indicated. All control reactions (lane 1 in each panel) were performed using CjLLO-enriched extracts that lacked CjPglB. Blots were probed with anti-hexa-histidine antibody (anti-His) to detect the acceptor proteins or hR6 serum (anti-glycan) to detect the N-glycan. Arrows denote aglycosylated (g0) and singly glycosylated (g1) forms of the protein targets. Asterisks denote bands corresponding to non-specific serum antibody binding. Molecular weight (MW) markers are indicated at left. Results are representative of at least three biological replicates (see Supplementary FIG. 4 for replicate data).
Figure 17:
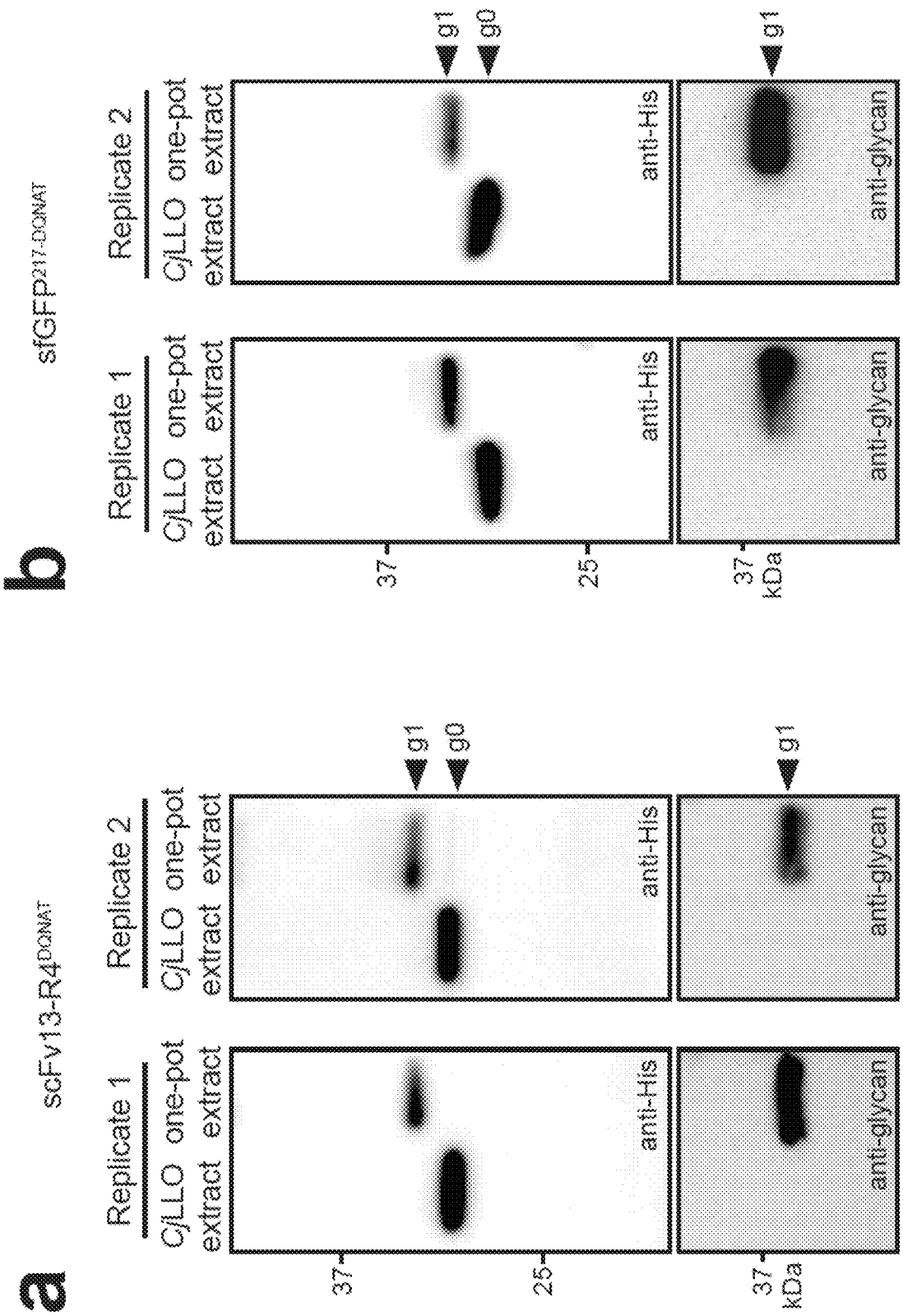
FIG. 17. Independent biological replicates for one-pot CFGpS reactions. Western blot analysis replicated twice for both the (a) scFv13-R4DQNAT and (b) sfGFP217-DQNAT acceptor proteins produced using crude CLM24 extract selectively enriched with (i) CjPglB from heterologous overexpression from pSF-CjPglB and (ii) CjLLOs from heterologous overexpression from pMW07-pgl B. Each replicate experiment involved charging freshly prepared cell-free extracts with freshly purified pJL1-scFv13-R4DQNAT or pJL1-sfGFP217-DQNAT plasmid DNA. Control reactions (lane 1 in each panel) were performed using CjLLO-enriched extracts that lacked CjPglB. Blots were probed with anti-hexa-histidine antibody (anti-His) to detect acceptor proteins or hR6 serum (anti-glycan) to detect the N-glycan. Arrows denote aglycosylated (g0) and singly glycosylated (g1) forms of the protein targets. Molecular weight (MW) markers are indicated at left.
Figure 18:
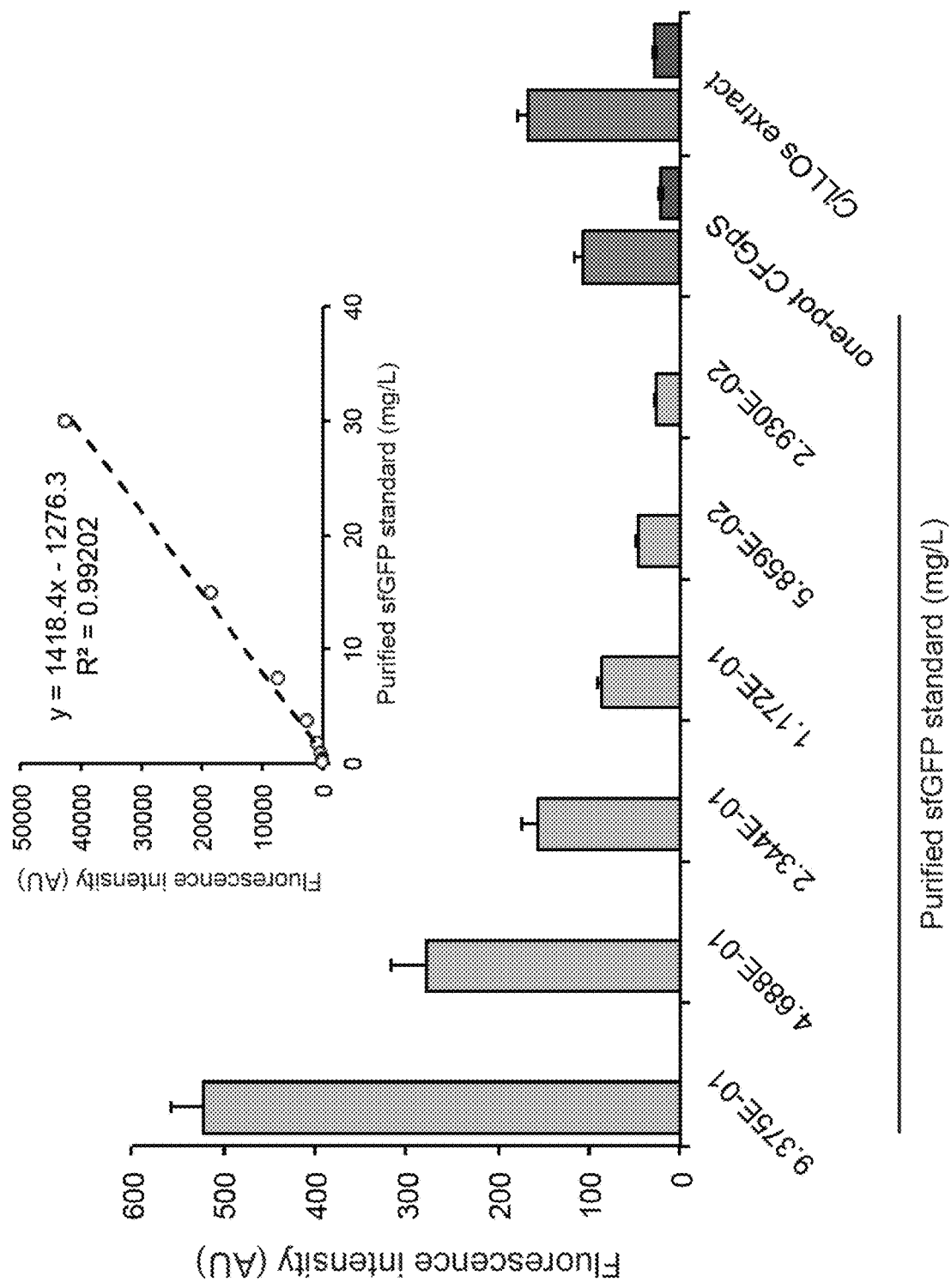
FIG. 18. CFGpS expression of active sfGFP. In-lysate fluorescence activity for glycosylated (one-pot CFGpS) and aglycosylated (CjLLOs extract) sfGFP217-DQNAT produced in cell-free reactions charged with plasmid pJL1-sfGFP217-DQNAT or with no plasmid DNA. Following 2-h reactions, cell-free reactions containing glycosylated and aglycosylated sfGFP217-DQNAT were diluted 10 times with water and then subjected to fluorescence measurement. Excitation and emission wavelengths for sfGFP were 485 and 528 nm, respectively. Calibration curve was prepared by measuring fluorescence intensity of aglycosylated sfGFP217-DQNAT expressed and purified from E. coli cells and mixed with empty extract. Linear regression analysis (inset) was used to calculate the concentration of sfGFP in the samples. Data are the average of three biological replicates and error bars represent the standard deviation.
Figure 19:
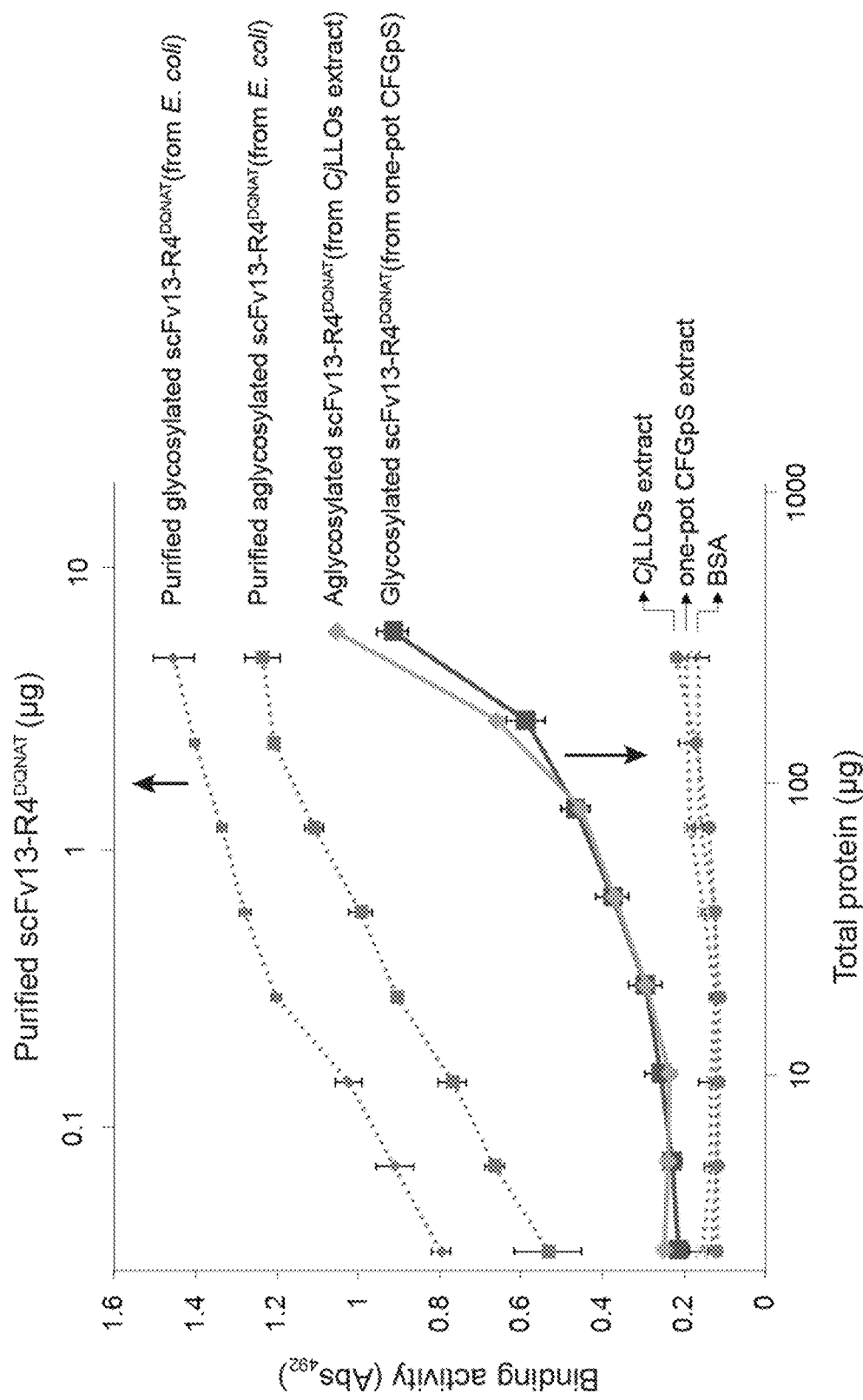
FIG. 19. CFGpS expression of active scFv antibody fragment. Antigen-binding activity for -gal-specific scFv13-R4DQNAT measured by ELISA with E. coli-gal as immobilized antigen. The scFv13-R4DQNAT acceptor was produced as a glycosylated protein in one-pot CFGpS or an aglycosylated protein in control extracts containing CjLLOs but not CjPglB. Extracts were primed with plasmid pJL1-scFv13-R4DQNAT. Positive controls included the same scFv13-R4DQNAT protein produced in vivo by recombinant expression in E. coli in the presence (glycosylated) or absence (aglycosylated) of glycosylation machinery. Negative controls included extracts without plasmid and BSA. Data are the average of three biological replicates and error bars represent the standard deviation FIG. 20. CFGpS-derived hEPO glycovariants stimulate cell proliferation. Stimulation of human erythroleukemia TF-1 cell proliferation following incubation with purified rhEPO standard or hEPO variants produced in cell-free reactions. For CFGpS-derived hEPO glycovariants, TF-1 cells were treated with either glycosylated hEPO variants produced in one-pot CFGpS or aglycosylated hEPO variants produced in control extracts containing CjLLOs but not CjPglB. To produce the hEPO variants, extracts were primed with plasmid pJL1-hEPO22-DQNAT-26 (N24), pJL1-hEPO36-DQNAT-40 (N38), or pJL1-hEPO81-DQNAT-85 (N83). For positive control rhEPO samples, cells were treated with serial dilutions of commercial rhEPO that was purified from CHO cells and thus glycosylated. TF-1 cells incubated with empty extracts or PBS (unstimulated) served as negative controls while RPMI media without cells was used as the blank. Regression analysis (inset) was performed to determine the concentration of hEPO variants in the samples. Data are the average of three biological replicates and error bars represent the standard deviation.

One-pot extract promotes efficient biosynthesis of diverse glycoprotein targets. To create a fully integrated CFGpS platform that permits one-pot synthesis of N glycoproteins without the need for supplementation of either purified OSTs or solvent extracted LLOs (FIG. 9), we produced crude S30 extract from CLM24 cells heterologously overexpressing CjPglB and the *C. jejuni* glycan biosynthesis enzymes. The resulting extract was selectively enriched with both CjPglB and CjLLOs donor to an extent that was indistinguishable from the separately prepared extracts (FIGS. 16a and b). Using this extract, CFGpS reactions were performed by addition of plasmid DNA encoding either scFv13-R4DQNAT or sfGFP217-DQNAT. In both cases, 100% protein glycosylation was achieved without the need for exogenous supplementation of separately prepared glycosylation components (FIG. 13a). Independent extract preparations yielded identical results for both protein substrates, confirming the reproducibility of the CFGpS system (FIGS. 17a and b). Importantly, the in vitro synthesized scFv13-R4DQNAT and sfGFP217-DQNAT proteins retained biological activity that was unaffected by N-glycan addition (FIG. 18). From the activity data, the yield of glycosylated scFv13-R4DQNAT and sfGFP217-DQNAT proteins produced by the one-pot CFGpS system was determined to be ~20 mg L-1 and ~10 mg L-1, respectively.

Figure 20:
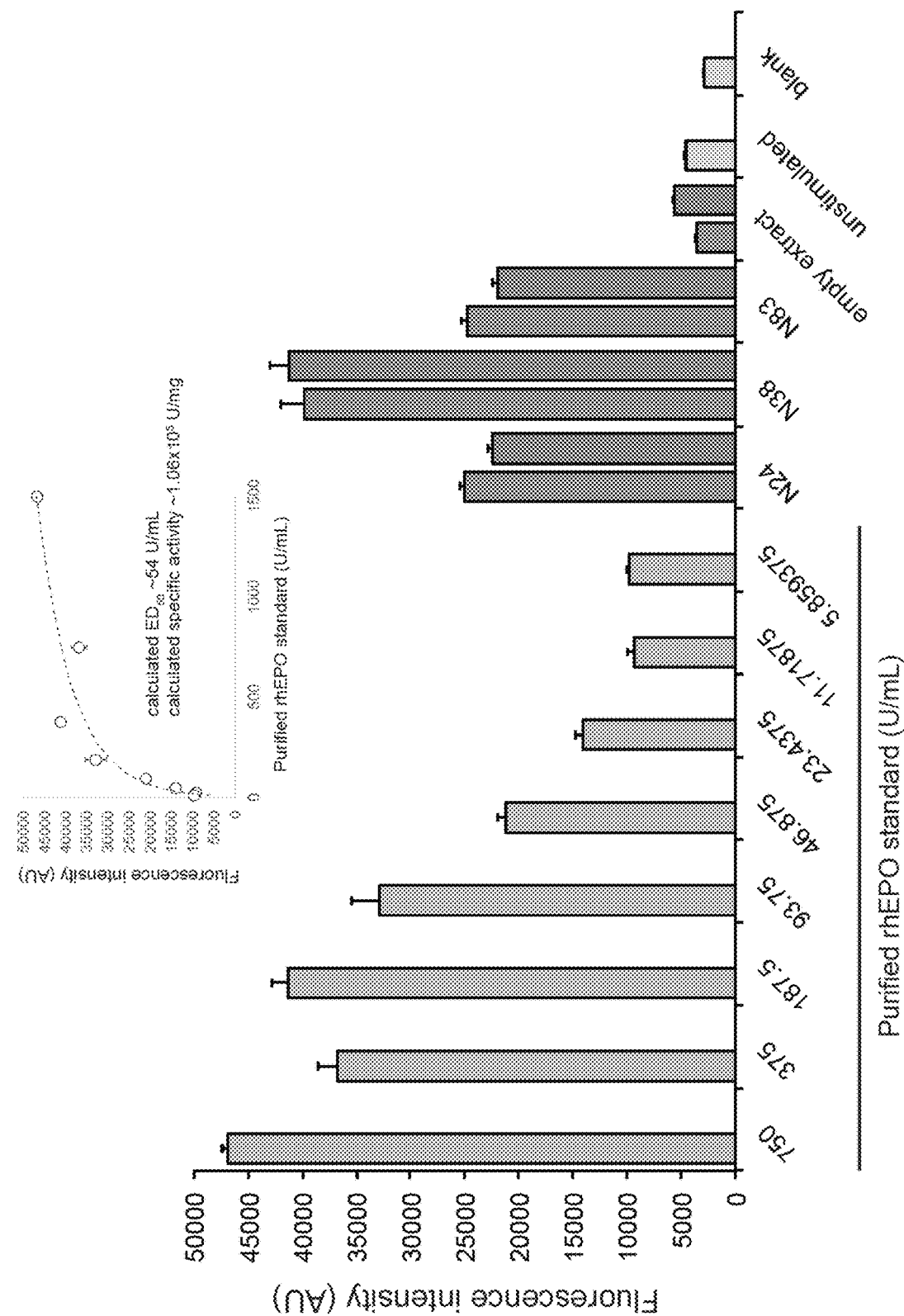

To determine whether human glycoproteins could be similarly produced in our one-pot system, we constructed plasmids for cell-free expression of human erythropoietin (hEPO) glycovariants in which the native sequons at residue N24 (22-AENIT-26) (SEQ ID NO:7), N38 (36-NENIT-40) (SEQ ID NO:8) or N83 (81-LVNSS-85) (SEQ ID NO:9) were individually mutated to the optimal bacterial sequon, DQNAT (SEQ ID NO:6) (FIG. 13b). CFGpS reactions were then initiated by priming the all-in-one extract with plasmid DNA encoding hEPO$^{22-DQNAT-26}$, hEPO$^{36-DQNAT-40}$, or hEPO$^{81-DQNAT-85}$. Western blot analysis revealed clearly detectable glycosylation of each hEPO glycovariant with 100% glycosylated product for the N24 and N38 sites and ~30-40% for the N83 site (FIG. 13b). As with the model glycoproteins scFv13-R4$^{DQNAT}$ and sfGFP$^{217-DQNAT}$ above, all three glycosylated hEPO variants retained biological activity that was indistinguishable from the activity measured for the corresponding aglycosylated counterparts, with yields in the ~10 mg L$^{-1}$ range (FIG. 20). Collectively, these findings establish that one-pot CFGpS extracts are capable of co-activating protein synthesis and N-glycosylation in a manner that yields efficiently glycosylated proteins including those of human origin.

Discussion

In this work, we successfully created a technology for one-pot biosynthesis of N-linked glycoproteins in the absence of living cells. This was accomplished by uniting cell-free transcription and translation with the necessary reaction components for N-linked protein glycosylation through a process of crude extract enrichment. By preparing OST- and LLO-enriched crude S30 extracts from a glyco-optimized chassis strain, glycosylation-competent lysates were capable of supplying efficiently glycosylated target proteins, with conversion levels at or near 100% in most instances. The glycoprotein yields obtained for three structurally diverse proteins were in the 10-20 mg L$^{-1}$ range, which compare favorably to some of the yields reported previously for these proteins in different CFPS kits or in-house generated extracts. For example, Jackson et al. produced 3.6 mg L$^{-1}$ of GFP using the PURExpress system[44], Stech et al. produced ~12 mg L$^{-1}$ of an anti-SMAD2 scFv using a CHO cell-derived lysate[45], Ahn et al. produced 55 mg L$^{-1}$ of hEPO using an *E. coli*-derived S30 lysate[46], and Gurramkonda, et at produced ~120 mg L$^{-1}$ of hEPO using a CHO cell-derived lysate supplemented with CHO microsomes.

Furthermore, this work represents the first demonstration of extract enrichment with catalytically active multipass transmembrane enzymes (and their corresponding lipid-linked substrates) without the need for domain truncation or supplementation of extra scaffold molecules,[47] and provides a blueprint for other CFPS-based applications beyond glycosylation that involve this important class of proteins. Moreover, the ability of OST- or LLO-enriched crude extracts to co-activate glycosylation partially bypassed the need for costly, labor-intensive preparation of glycosylation components and paved the way for a modular single-pot CFGpS platform in which protein synthesis and N-linked glycosylation were integrated.

A major advantage of the CFGpS system developed here is the level of control it affords over each of the glycosylation components (i.e., catalysts, substrates, and cofactors) in terms of important process variables such as relative concentration, timing of addition, overall reaction time, etc. Likewise, genome engineering of the chassis strain used to supply the extract, such as our recent report enhancing cell-free synthesis containing multiple, identical non canonical amino acids[16], makes it possible to eliminate inhibitory substances such as glycosidases that catalyze the undesired hydrolysis of glycosidic linkages. This user-level control provides an opportunity to overcome system bottlenecks that effectively limit glycosylation efficiency as we showed with both the *C. jejuni* heptasaccharide and the eukaryotic Man$_3$GlcNAc$_2$ glycan. Moreover, the open nature of the CFGpS system could be further exploited in the future to introduce components that may otherwise be incompatible with chassis strain expression such as unusual and/or non-natural LLOs that cannot be assembled or flipped in vivo.

An additional advantage of the CFGpS system is that it does not rely on commercial cell-free kits to support protein synthesis. For comparison, the glycoproteins yields obtained here were ~10-20 ng µL$^{-1}$ in reactions costing ~$0.01-0.03 per µL (data not shown and [48]) versus previous kit-based (e.g., Promega L110; NEB© E6800S) glycoprotein yields of ~100 ng µL$^{-1}$ [32] in reactions costing ~$1 per µL[49]. As a result, our system can synthesize ~1000 ng glycoprotein/$ reagents compared to the previously published approach that can synthesize ~100 ng glycoprotein/$ reagents, representing an order of magnitude improvement in relative protein synthesis yields. It is also worth noting that this cost analysis does not take into account the cost of purifying OSTs or extracting LLOs that were used to supplement the commercial kits in our previous work[32]. We anticipate this reduction in cost will encourage adoption of the CFGpS platform.

Perhaps the most important feature of the CFGpS platform is its modularity, which was evidenced by the interchangeability of: (i) OST enzymes from different bacterial species; (ii) engineered LLOs with glycan moieties derived from bacteria and eukaryotes; and (iii) diverse acceptor protein targets including naturally occurring human N-glycoproteins with terminal or internal acceptor sequons. Importantly, enriched extracts could be readily mixed in a manner that enabled screening of an OST panel whose activities in CFGpS were in line with previously reported activities in vivo[50], thereby validating this lysate mixing strategy as a useful tool for rapid characterization of glycosylation enzyme function and for prototyping glycosylation reactions. In light of this modularity, we envision that lysate enrichment could be further expanded beyond the glycosylation components/substrates tested here. For example, extracts could be heterologously enriched with alternative membrane-bound or soluble OSTs that catalyze N-linked or O-linked glycosyl transfer reactions. Such biocatalyst swapping is expected to be relatively straightforward in light of the growing number of prokaryotic and eukaryotic OST enzymes that have been recombinantly expressed in functional conformations and used to promote in vitro glycosylation reactions[47, 50-55]. Likewise, as newly engineered glycan biosynthesis pathways emerge[56], these could be readily integrated into the CFGpS platform through heterologous expression of GTs in the chassis strain. The ability to modularly reconfigure and quickly interrogate glycosylation systems in vitro should make the CFGpS technology a useful new addition to the glycoengineering toolkit for increasing our understanding of glycosylation and, in the future, advancing applications of on demand biomolecular manufacturing[57, 58, 59].

Experimental Methods

Bacterial strains and plasmids. The following *E. coli* strains were used in this study: DH5a, BL21(DE3) (Novagen), CLM24, and Origami2(DE3) gmd::kan ΔwaaL. DH5a was used for plasmid cloning and purification. BL21(DE3) was used for expression and purification of the scFv13-R4$^{DQNAT}$ acceptor protein that was used in all in vitro glycosylation reactions. CLM24 is a glyco-optimized derivative of W3110 that carries a deletion in the gene encoding the WaaL ligase, thus facilitating the accumulation of preassembled glycans on Und-PP[34]. CLM24 was used for purification of the CjOST enzyme, organic solvent-based extraction of all LLOs bearing bacterial glycans, and the source strain for preparing extracts with and without selectively enriched glycosylation components. Origami2(DE3) gmd::kan ΔwaaL was used for producing Man$_3$GlcNAc$_2$-bearing LLOs and was generated by sequential mutation with P1vir phage transduction using the respective strains from the Keio collection 60 as donors, which were obtained from the *Coli* Genetic Stock Center (CGSC). In brief, donor lysate was generated from strain JW3597-1 (ΔrfaL734::kan) and the resulting phage was used to infect Origami2(DE3) target cells. After plating transformants on LB plates containing kanamycin (Kan), successful transductants were selected and their Kan resistance cassettes were removed by transforming with temperature-sensitive plasmid pCP20[61]. The resulting strain, Origami2(DE3) ΔwaaL, was then used for subsequent deletion of the gmd gene according to an identical strategy but using donor strain JW2038-1 (Δgmd751::kan).

Plasmids constructed in this study were made using standard cloning protocols and confirmed by DNA sequencing. These included the following. Plasmid pJL1-scFv13-R4$^{DQNAT}$ was generated by first PCR amplifying the gene encoding scFv13-R4$^{DQNAT}$ from pET28a-scFv13-R4(N34L, N77L)$^{DQNAT}$, where the N34L and N77L mutations were introduced to eliminate putative internal glycosylation sites in scFv13-R4[50]. The resulting PCR product was then ligated between NcoI and SalI restriction sites in plasmid pJL1, a pET-based vector used for CFPS[62]. Plasmid pJL1-sfGFP$^{217-DQNAT}$ was generated by ligating a commercially-synthesized DNA fragment encoding sfGFP$^{217-DQNAT}$ (Integrated DNA Technologies) into pJL1. This version of sfGFP contains an additional GT insertion after K214, which extends this flexible loop before the final beta sheet[63]. Into this flexible loop, immediately after T216, we grafted a 21 amino acid sequence containing the *C. jejuni* AcrA N123 glycosylation site[32], but with an optimal DQNAT (SEQ ID NO:6) sequon in place of the native AcrA sequon. Similar procedures were used to generate plasmids pJL1-sfGFP$^{217-AQNAT}$, pJL1-hEPO$^{22-DQNAT-26}$, pJL1-hEPO$^{36-DQNAT-40}$, and pJL1-hEPO$^{81-DQNAT-85}$. In the case of pJL1-hEPO$^{22-DQNAT-26}$, the gene for mature human EPO was designed such that the native sequon at N24 was changed from 22-AENIT-26 to an optimal bacterial sequon, DQNAT. Identical cloning strategies were carried out to separately introduce optimal DQNAT motifs in place of the native hEPO sequons 36-NENIT-40 and 81-LVNSS-85. Recombinant expression of the *E. coli* 09 primer-adaptor glycan (Man$_3$GlcNAc) on Und-PP was achieved by cloning the genes encoding the WbdB and WbdC mannosyltransferase enzymes derived from *E. coli* ATCC31616 for assembling the glycan, and RfbK and RfbM, also derived from *E. coli* ATCC31616 for increasing the pool of available GDP-mannose, in *E. coli* MG1655. Plasmid pConYCGmCB was constructed by isothermal Gibson assembly and encodes an artificial operon comprised of: (i) the yeast glycosyltransferases Alg13, Alg14, Alg1, and Alg2 for Man$_3$GlcNAc$_2$ glycan biosynthesis[12] and (ii) the *E. coli* enzymes phosphomannomutase (ManB) and mannose-1-phosphate guanylyltransferase (ManC), which together increase availability of GDP-mannose substrates for the Alg1 and Alg2 enzymes.

Protein expression and purification. Purification of CjPglB was performed according to a previously described protocol[32]. Briefly, a single colony of *E. coli* CLM24 carrying plasmid pSN18[64] was grown overnight at 37° C. in 50 mL of Luria-Bertani (LB; 10 g $L^{-1}$ tryptone, 5 g $L^{-1}$ yeast extract, 5 g $L^{-1}$ NaCl, pH 7.2) supplemented with ampicillin (Amp) and 0.2% (w/v %) D-glucose. Overnight cells were subcultured into 1 L of fresh terrific broth (TB; 12 g $L^{-1}$ tryptone, 24 g $L^{-1}$ yeast extract, 0.4% (v/v %) glycerol, 10% (v/v %) 0.17 M $KH_2PO_4$/0.72 M $K_2HPO_4$ phosphate buffer), supplemented with Amp and grown until the absorbance at 600 nm ($Abs_{600}$) reached a value of ~0.7. The incubation temperature was adjusted to 16° C., after which protein expression was induced by the addition of L-arabinose to a final concentration of 0.02% (w/v). Protein expression was allowed to proceed for 20 h at 16° C. Cells were harvested by centrifugation and then disrupted using a homogenizer (Avestin C5 EmulsiFlex). The lysate was centrifuged to remove cell debris and the supernatant was ultracentrifuged (100,000×g) for 2 h at 4° C. The resulting pellet containing the membrane fraction was fully resuspended with a Potter-Elvehjem tissue homogenizer in buffer containing 50 mM HEPES, 250 mM NaCl, 10% (v/v %) glycerol, and 1% (w/v) n-dodecyl-β-D-maltoside (DDM) at pH 7.5. The suspension was incubated at room temperature for 1 h to facilitate detergent solubilization of CjPglB from native *E. coli* lipids, which were removed by subsequent ultracentrifugation (100,000×g) for 1 h at 4° C. The supernatant containing DDM-solubilized CjPglB was purified using Ni-NTA resin (Thermo) according to manufacturer's specification with the exception that all buffers were supplemented with 1% (w/v %) DDM. The elution fraction from Ni-NTA purification was then subjected to size exclusion chromatography (SEC) using an AKTA Explorer FPLC system (GE Healthcare) with Superdex 200 10/300 GL column. Purified protein was stored at a final concentration of 1-2 mg/mL in OST storage buffer (50 mM HEPES, 100 mM NaCl, 5% (v/v %) glycerol, 0.01% (w/v %) DDM, pH 7.5) at 4° C. Glycerol concentration in the sample was adjusted to 20% (v/v %) for long-term storage at −80° C.

Purification of acceptor protein scFv13-R4$^{DQNAT}$ was carried out as described previously[50]. Briefly, *E. coli* strain BL21(DE3) carrying plasmid pET28a-scFv13-R4(N34L, N77L)$^{DQNAT}$ was grown in 1.0 L of TB supplied with kanamycin. The culture was incubated at 37° C. until $Abs_{600}$ reached ~0.7, at which point protein expression was induced by addition of isopropyl β-D-1-thiogalactopyranoside (IPTG) to a final concentration of 0.1 mM. Protein expression was allowed to proceed for 20 h at 25° C. Cells were harvested and disrupted identically as described above. The scFv13-R4$^{DQNAT}$ protein was purified using Ni-NTA resin followed by SEC according to manufacturer's protocols. Protein was stored at a final concentration of 1-2 mg $mL^{-1}$ in storage buffer (50 mM HEPES, 250 mM NaCl, 1 mM EDTA, pH 7.5) at 4° C.

Extraction of LLOs. The protocol for organic solvent extraction of LLOs from *E. coli* membranes was adapted from a previously described protocol[32, 65]. In most cases, a single colony of strain CLM24 carrying a plasmid for target glycan biosynthesis was grown overnight in LB media. The notable exceptions were LLOs bearing the *W. succinogenes* N-glycan (WsLLOs), which were produced using DH5a cells carrying the pEpiFOS-5pgl5 fosmid (kindly provided by Dr. Markus Aebi), and LLOs bearing $Man_3GlcNAc_2$, which were produced using Origami2(DE3) gmd::kan ΔwaaL cells carrying plasmid pConYCGmCB. Overnight cells were subcultured into 1.0 L of TB supplemented with an appropriate antibiotic and grown until the $Abs_{600}$ reached ~0.7. The incubation temperature was adjusted to 30° C. for biosynthesis of all glycans except for $Man_3GlcNAc_2$, which was adjusted to 16° C. For plasmid pMW07-pglΔB, protein expression was induced with L-arabinose at a final concentration of 0.2% (w/v %) while for fosmid pEpiFOS-5pgl5 induction was with isopropyl β-D-1-thiogalactopyranoside (IPTG) at a final concentration of 1.0 mM. All other plasmids involved constitutive promoters and thus did not require chemical inducers. After 16 h, cells were harvested by centrifugation and cell pellets were lyophilized to complete dryness at −70° C. For extraction of CjLLOs, native and engineered ClLLOs, *E. coli* 09 primer-adaptor LLOs, and WsLLOs, the lyophilisates were suspended in 10:20:3 volumetric ratio of $CHCl_3$:$CH_3OH$:$H_2O$ solution and incubated at room temperature for 15 min to facilitate extraction of LLOs. For extraction of LLOs bearing $Man_3GlcNAc_2$ glycan, lyophilisate was successively suspended in 10:20 (v/v %) $CHCl_3$:$CH_3OH$ solution, water, and 10:20:3 $CHCl_3$:$CH_3OH$:$H_2O$ solution with 15 min of incubation at room temperature between each step. In each case, the final suspension was centrifuged (4000×g) for 15 min, after which the organic layer (bottom layer) was collected and dried with a vacuum concentrator followed by lyophilization. Lyophilisates containing active LLOs were resuspended in cell-free glycosylation buffer (10 mM HEPES, pH 7.5, 10 mM $MnCl_2$, and 0.1% (w/v %) DDM) and stored at 4° C.

Preparation of crude S30 extracts. CLM24 source strains were grown in 2×YTPG (10 g $L^{-1}$ yeast extract, 16 g $L^{-1}$ tryptone, 5 g $L^{-1}$ NaCl, 7 g $L^{-1}$ $K_2HIPO_4$, 3 g $L^{-1}$ $KH_2PO_4$, 18 g $L^{-1}$ glucose, pH 7.2) until the $Abs_{600}$ reached ~3. To generate OST-enriched extract, CLM24 carrying plasmid pSF-CjPglB, pSF-CcPglB, pSF-DdPglB, pSF-DgPglB, or pSF-DvPglB[50] was used as the source strain. To generate LLO-enriched extract, CLM24 carrying plasmid pMW07-pglΔB was used as the source strain. To generate one-pot extract containing both OST and LLOs, CLM24 carrying pMW07-pglΔB and pSF-CjOST was used as the source strain. As needed, the expression of glycosylation components was induced with L-arabinose at final concentration of 0.02% (w $v^{-1}$). After induction, protein expression was allowed to proceed at 30° C. to a density of $OD_{600}$ ~3, at which point cells were harvested by centrifugation (5,000× g) at 4° C. for 15 min. All subsequent steps were carried out at 4° C. unless otherwise stated. Pelleted cells were washed three times in S30 buffer (10 mM tris acetate, 14 mM magnesium acetate, 60 mM potassium acetate, pH 8.2). After the last wash, cells were pelleted at 7000×g for 10 min and flash frozen on liquid nitrogen. To make lysate, cells were thawed and resuspended to homogeneity in 1 mL of S30 buffer per 1 g of wet cell mass. Cells were disrupted using an Avestin EmulsiFlex-B15 high-pressure homogenizer at 20,000-25,000 psi with a single passage. Alternatively, cell lysis was performed using a simple sonication method[37]. The lysate was then centrifuged twice at 30,000×g for 30 min to remove cell debris. Supernatant was transferred to a new vessel and incubated with 250 rpm shaking at 37° C. for 60 min to degrade endogenous mRNA transcripts and disrupt existing polysome complexes in the lysate. Following centrifugation (15,000×g) for 15 min at 4° C., supernatant was collected, aliquoted, flash-frozen in liquid nitrogen, and stored at −80° C. S30 extract was active for about 3 freeze-thaw cycles and contained ~40 g $L^{-1}$ total protein as measured by Bradford assay.

Cell-free glycoprotein synthesis. For in vitro glycosylation of purified acceptor protein, reactions were carried out in a 50 μL volume containing 3 μg of scFv13-R4$^{DQNAT}$ 2 g of purified CjPglB, and 5 μg extracted LLOs (in the case of $Man_3GlcNAc_2$ LLOs, 20 μg was used) in in vitro glycosylation buffer (10 mM HEPES, pH 7.5, 10 mM $MnCl_2$, and 0.1% (w/v %) DDM). The reaction mixture was incubated at 30° C. for 16 h. For crude extract-based expression of glycoproteins, a two-phase scheme was implemented. In the first phase, protein synthesis was carried out with a modified PANOx-SP system[66]. Specifically, 1.5 mL microcentrifuge tubes were charged with 15-μL reactions containing 200 ng plasmid DNA, 30% (v/v) S30 extract and the following: 12 mM magnesium glutamate, 10 mM ammonium glutamate, 130 mM potassium glutamate, 1.2 mM adenosine triphosphate (ATP), 0.85 mM guanosine triphosphate (GTP), 0.85 mM uridine triphosphate (UTP), 0.85 mM cytidine triphosphate (CTP), 0.034 mg/mL folinic acid, 0.171 mg/mL $E.\ coli$ tRNA (Roche), 2 mM each of 20 amino acids, 30 mM phosphoenolpyruvate (PEP, Roche), 0.33 mM nicotinamide adenine dinucleotide (NAD), 0.27 mM coenzyme-A (CoA), 4 mM oxalic acid, 1 mM putrescine, 1.5 mM spermidine, and 57 mM HEPES. For scFv13-R4$^{DQNAT}$ and hEPO$^{22\text{-}DQNAT\text{-}26}$, this phase was carried out at 30° C. for 4 h under oxidizing conditions while for sfGFP$^{217\text{-}DQNAT}$ and sfGFP$^{217\text{-}AQNAT}$ this phase was carried out at 30° C. for 5 min under reducing conditions. For oxidizing conditions, extract was pre-conditioned with 750 μM iodoacetamide in the dark at room temperature for 30 min and the reaction mix was supplied with 200 mM glutathione at a 3:1 ratio between oxidized and reduced forms. The active sfGFP yields from cell-free reactions were quantified by measuring fluorescence in-lysate and converting into concentration using a standard curve as previously described [37]. In the second phase, protein glycosylation was initiated by the addition of MnCl$_2$ and DDM at a final concentration of 10 mM and 0.1% (w/v %), respectively, and allowed to proceed at 30° C. for 16 h. As needed, reactions were supplemented with 2 μg of purified CjPglB (i.e., for CFGpS with LLO-enriched extracts) or 5 μg solvent-extracted CjLLOs (i.e., for CFGpS with OST-enriched extracts). All reactions were stopped by adding Laemmli sample buffer containing 5% PME, after which samples were boiled at 100° C. for 15 min and analyzed by SDS-PAGE and Western blotting.

Western blot analysis. Samples containing 0.5 μg of acceptor protein were loaded into SDS-PAGE gels. Following electrophoretic separation, proteins were transferred from gels onto Immobilon-P polyvinylidene difluoride (PVDF) membranes (0.45 μm) according to manufacturer's protocol. Membranes were washed twice with TBS buffer (80 g L$^{-1}$ NaCl, 20 g L$^{-1}$ KCl, and 30 g L$^{-1}$ Tris-base) followed by incubation for 1 h in blocking solution (50 g/L non-fat milk in TBST (TBS supplied with 0.05% (v/v %) Tween-20)). After blocking, membranes were washed 4 times with TBST with 10 min incubation between each wash. A first membrane was probed with 6×His-polyclonal antibody (Abcam, ab137839, 1:7500) that specifically recognizes hexahistidine epitope tags while a second replicate membrane was probed with one of the following: hR6 (1:10000) serum from rabbit that recognizes the native $C.\ jejuni$ and $C.\ lari$ glycan as well as engineered $C.\ lari$ glycan or ConA-HRP (Sigma, L6397, 1:2500) that recognizes Man$_3$GlcNac and Man$_3$GlcNAc$_2$. Probing of membranes was performed for at least 1 hour with shaking at room temperature, after which membranes were washed with TBST in the same manner as described above. For development, membranes were incubated briefly at room temperature with Western ECL substrate (BioRad) and imaged using a ChemiDoc™ XRS+ System. OST enzymes enriched in extracts were detected by an identical SDS-PAGE procedure followed by Western blot analysis with a polyclonal antibody specific to the FLAG epitope tag (Abcam, ab49763, 1:7500). The glycan component of LLOs enriched in extracts was detected by directly spotting 10 μL of extracts onto nitrocellulose membranes followed by detection with hR6 serum.

MS analysis. Approximately 2 μg of scFv13-R4$^{DQNAT}$ protein in solution was denatured with 6 M urea, reduced with 10 mM DTT, incubated at 34° C. for 1 h, then alkylated with 58 mM iodoacetamide for 45 min in the dark at room temperature and quenched by final 36 mM DTT. The solution was then diluted with 50 mM ammonium bicarbonate (pH 8.0) to a final buffer concentration of 1 M urea prior to trypsin digestion. Sample was digested with 0.2 μg of trypsin for 18 h at 37° C. The digestion was stopped by addition of TFA to a final pH 2.2-2.5. The samples were then desalted with SOLA HRP SPE Cartridge (ThermoFisher Scientific). The cartridges were conditioned with 1×0.5 mL 90% methanol, 0.1% trifluoroacetic acid (TFA) and equilibrated with 2×0.5 mL 0.1% (v/v %) TFA. The samples were diluted 1:1 with 0.2% (v/v %) TFA and run slowly through the cartridges. After washing with 2×0.5 mL of equilibration solution, peptides were eluted by 1×0.5 mL of 50% (v/v %) acetonitrile (ACN), 0.1% (v/v %) TFA and dried in a speed vacuum centrifuge.

The nanoLC-MS/MS analysis was carried out using UltiMate3000 RSLCnano (Dionex) coupled to an Orbitrap Fusion (ThermoFisher Scientific) mass spectrometer equipped with a nanospray Flex Ion Source. Each sample was reconstituted in 22 μL of 0.5% (w/v %) FA and 10 μL was loaded onto an Acclaim PepMap 100 C18 trap column (5 μm, 100 μm×20 mm, 100 Å, ThermoFisher Scientific) with nanoViper Fittings at 20 μL/min of 0.5% FA for on-line desalting. After 2 min, the valve switched to allow peptides to be separated on an Acclaim PepMap C18 nano column (3 μm, 75 μm×25 cm, ThermoFisher Scientific), in a 90 min gradient of 5% to 23% to 35% B at 300 nL/min (3 to 73 to 93 min, respectively), followed by a 9-min ramping to 90% B, a 9-min hold at 90% B and quick switch to 5% B in 1 min. The column was re-equilibrated with 5% B for 20 min prior to the next run. The Orbitrap Fusion was operating in positive ion mode with nanospray voltage set at 1.7 kV and source temperature at 275° C. External calibration for FT, IT and quadrupole mass analyzers was performed prior to the analysis. The Orbitrap full MS survey scan (m/z 400-1800) was followed by Top 3 second data-dependent Higher Collision dissociation product ion triggered ETD (HCD-pd-ETD) MS/MS scans for precursor peptides with 2-7 charges above a threshold ion count of 50,000 with normalized collision energy of 32%. MS survey scans were acquired at a resolving power of 120,000 (FWHM at m/z 200), with Automatic Gin Control (AGC)=2e5 and maximum injection time (Max IT)=50 ms, and HCD MS/MS scans at a resolution of 30,000 with AGC=5e4, Max IT=60 ms and with Q isolation window (m/z) at 3 for the mass range m/z 105-2000. Dynamic exclusion parameters were set at 1 within 60 s exclusion duration with ±10 ppm exclusion mass width. Product Ion trigger list consisted of peaks at 204.0867 Da (HexNAc oxonium ion), 138.0545 Da (HexNAc fragment), and 366.1396 Da (HexHexNAc oxonium ions). If one of the HCD product ions in the list was detected, two charge-dependent ETD MS/MS scans (EThcD) with HCD supplemental activation (SA) on the same precursor ion were triggered and collected in a linear ion trap. For doubly charged precursors, the ETD reaction time as set 150 ms and the SA energy was set at 30%, while the same parameters at 125 ms and 20%, respectively, were used for higher charged precursors. For both ion triggered scans, fluoranthene ETD reagent target was set at 2e5, AGC target at 1e4, Max IT at 105 ms and isolation window at 3. All data were acquired using Xcalibur 3.0 operation software and Orbitrap Fusion Tune Application v. 2.1 (ThermoFisher Scientific).

All MS and MS/MS raw spectra from each sample were searched using Byonics v. 2.8.2 (Protein Metrics) using the E coli protein database with added scFv13-R4$^{DQNAT}$ protein target sequence. The peptide search parameters were as follows: two missed cleavage for full trypsin digestion with fixed carbamidomethyl modification of cysteine, variable modifications of methionine oxidation, and deamidation on asparagine/glutamine residues. The peptide mass tolerance was 10 ppm and fragment mass tolerance values for HCD and EThcD spectra were 0.05 Da and 0.6 Da, respectively. Both the maximum number of common and rare modifications were set at two. The glycan search was performed against a list of 309 mammalian N-linked glycans in Byonic software. Identified peptides were filtered for maximum 2% FDR. The software exported the results of the search to a spreadsheet.

GFP fluorescence activity. The activity of cell-free-derived sfGFP was determined using an in-lysate fluorescence analysis as described previously[37]. Briefly, 2 uL of cell-free synthesized glycosylated sfGFP reaction was diluted into 48 uL of nanopure water. The solution was then placed in a Costar 96-well black assay plate (Corning). Excitation and emission wavelength for sfGFP fluorescence were at 485 and 528 nm, respectively.

Enzyme-linked immunosorbent analysis (ELISA). Costar 96-well ELISA plates (Corning) were coated overnight at 4° C. with 50 µl of 1 mg mL$^{-1}$ E. coli-gal (Sigma-Aldrich) in 0.05 M sodium carbonate buffer (pH 9.6). After blocking with 5% (w/v %) bovine serum albumin (BSA) in PBS for 3 h at room temperature, the plates were washed four times with PBST buffer (PBS, 0.05% (v/v %) Tween-20, 0.3% (w/v %) BSA) and incubated with serially diluted purified scFv13 R4 samples or soluble fractions of CFGpS lysates for 1 h at room temperature. Samples were quantified by the Bradford assay and an equivalent amount of total protein was applied to the plate. After washing four times with the same buffer, anti-6x-His-HRP conjugated rabbit polyclonal antibody (Abcam) in 3% PBST was added to each well for 1 h. Plates were washed and developed using standard protocols.

In vitro cell proliferation assay. Human erythroleukemia TF-1 cells (Sigma) that require granulocyte-macrophage colony-stimulating factor (GM-CSF), interleukin 3 (IL-3), or hEPO for growth and survival were used. Cells were maintained in RPMI-1640 media supplemented with 10% FBS, 50 U/mL penicillin, 50 mg/mL streptomycin, 2 mM glutamine, and 2 ng/mL GM-CSF at 37° C. in a humidified atmosphere containing 5% $CO_2$. After 16 h incubation in RPMI-1640 media without GM-CSF, cells were counted, harvested, and resuspended in fresh media. $5 \times 10^3$ TF-1 cells/well were seeded in a 96-well assay plate, and EPO standards or samples were added to final desired concentrations to each well. Cells were incubated with for 6 h in humid incubator before adding alamarBlue®. After 12 h, fluorescence signal was measured at 560 nm/590 nm excitation/emission wavelength.

REFERENCES

1. Helenius, A. & Aebi, M. Intracellular functions of N-linked glycans. Science 291, 2364-9 (2001).
2. Imperiali, B. & O'Connor, S. E. Effect of N-linked glycosylation on glycopeptide and glycoprotein structure. Curr Opin Chem Biol 3, 643-9 (1999).
3. Hebert, D. N., Lamriben, L., Powers, E. T. & Kelly, J. W. The intrinsic and extrinsic effects of N-linked glycans on glycoproteostasis. Nat Chem Biol 10, 902-910 (2014).
4. Rudd, P. M., Elliott, T., Cresswell, P., Wilson, I. A. & Dwek, R. A. Glycosylation and the immune system. Science 291, 2370-6 (2001).
5. Wolfert, M. A. & Boons, G. J. Adaptive immune activation: glycosylation does matter. Nat Chem Biol 9, 776-84 (2013).
6. Lanctot, P. M., Gage, F. H. & Varki, A. P. The glycans of stem cells. Curr Opin Chem Biol 11, 373-80 (2007).
7. Sinclair, A. M. & Elliott, S. Glycoengineering: the effect of glycosylation on the properties of therapeutic proteins. J Pharm Sci 94, 1626-35 (2005).
8. Raman, R., Raguram, S., Venkataraman, G., Paulson, J. C. & Sasisekharan, R. Glycomics: an integrated systems approach to structure-function relationships of glycans. Nat Methods 2, 817-24 (2005).
9. Rudd, P. M. & Dwek, R. A. Glycosylation: heterogeneity and the 3D structure of proteins. Crit Rev Biochem Mol Biol 32, 1-100 (1997).
10. Meuris, L. et al. GlycoDelete engineering of mammalian cells simplifies N-glycosylation of recombinant proteins. Nat Biotechnol 32, 485-9 (2014).
11. Hamilton, S. R. et al. Production of complex human glycoproteins in yeast. Science 301, 1244-6 (2003).
12. Valderrama-Rincon, J. D. et al. An engineered eukaryotic protein glycosylation pathway in Escherichia coli. Nat Chem Biol 8, 434-6 (2012).
13. Carlson, E. D., Gan, R., Hodgman, C. E. & Jewett, M. C. Cell-free protein synthesis: applications come of age. Biotechnol Adv 30, 1185-94 (2012).
14. Kiga, D. et al. An engineered Escherichia coli tyrosyl-tRNA synthetase for site-specific incorporation of an unnatural amino acid into proteins in eukaryotic translation and its application in a wheat germ cell-free system. Proc Natl Acad Sci USA 99, 9715-20 (2002).
15. Oza, J. P. et al. Robust production of recombinant phosphoproteins using cell-free protein synthesis. Nat Commun 6, 8168 (2015).
16. Martin, R. W. et al. Cell-free protein synthesis from genomically recoded bacteria enables multisite incorporation of noncanonical amino acids. Nat Commun 9, 1203 (2018).
17. Stapleton, J. A. & Swartz, J. R. Development of an in vitro compartmentalization screen for high-throughput directed evolution of [FeFe] hydrogenases. PLoS One 5, e15275 (2010).
18. Albayrak, C. & Swartz, J. R. Cell-free co-production of an orthogonal transfer RNA activates efficient site-specific non-natural amino acid incorporation. Nucleic Acids Res 41, 5949-63 (2013).
19. Karim, A. S. & Jewett, M. C. A cell-free framework for rapid biosynthetic pathway prototyping and enzyme discovery. Metab Eng 36, 116-126 (2016).
20. Kaiser, L. et al. Efficient cell-free production of olfactory receptors: detergent optimization, structure, and ligand binding analyses. Proc Natl Acad Sci USA 105, 15726-31 (2008).
21. Dudley, Q. M., Anderson, K. C. & Jewett, M. C. Cell-Free Mixing of Escherichia coli Crude Extracts to Prototype and Rationally Engineer High-Titer Mevalonate Synthesis. ACS Synth Biol 5, 1578-1588 (2016).
22. Moore, S. J. et al. Rapid acquisition and model-based analysis of cell-free transcription-translation reactions from nonmodel bacteria. Proc Natl Acad Sci USA 115, E4340-E4349 (2018).

23. Goshima, N. et al. Human protein factory for converting the transcriptome into an in vitro-expressed proteome. Nature Methods 5, 1011-1017 (2008).
24. Matsuoka, K., Komori, H., Nose, M., Endo, Y. & Sawasaki, T. Simple screening method for autoantigen proteins using the N-terminal biotinylated protein library produced by wheat cell-free synthesis. J Proteome Res 9, 4264-73 (2010).
25. Tarui, H., Imanishi, S. & Hara, T. A novel cell-free translation/glycosylation system prepared from insect cells. J Biosci Bioeng 90, 508-14 (2000).
26. Moreno, S. N., Ip, H. S. & Cross, G. A. An mRNA-dependent in vitro translation system from *Trypanosoma brucei*. Mol Biochem Parasitol 46, 265-74 (1991).
27. Mikami, S., Kobayashi, T., Yokoyama, S. & Imataka, H. A hybridoma-based in vitro translation system that efficiently synthesizes glycoproteins. J Biotechnol 127, 65-78 (2006).
28. Brodel, A. K. et al. IRES-mediated translation of membrane proteins and glycoproteins in eukaryotic cell-free systems. PLoS One 8, e82234 (2013).
29. Shibutani, M., Kim, E., Lazarovici, P., Oshima, M. & Guroff, G. Preparation of a cell-free translation system from PC12 cell. Neurochem Res 21, 801-7 (1996).
30. Lingappa, V. R., Lingappa, J. R., Prasad, R., Ebner, K. E. & Blobel, G. Coupled cell-free synthesis, segregation, and core glycosylation of a secretory protein. Proc Natl Acad Sci USA 75, 2338-42 (1978).
31. Rothblatt, J. A. & Meyer, D. I. Secretion in yeast: reconstitution of the translocation and glycosylation of alpha-factor and invertase in a homologous cell-free system. Cell 44, 619-28 (1986).
32. Guarino, C. & DeLisa, M. P. A prokaryote-based cell-free translation system that efficiently synthesizes glycoproteins. Glycobiology 22, 596-601 (2012).
33. Weerapana, E. & Imperiali, B. Asparagine-linked protein glycosylation: from eukaryotic to prokaryotic systems. Glycobiology 16, 91R-101R (2006).
34. Feldman, M. F. et al. Engineering N-linked protein glycosylation with diverse O antigen lipopolysaccharide structures in *Escherichia coli*. Proc Natl Acad Sci USA 102, 3016-21 (2005).
35. Liu, D. & Reeves, P. R. *Escherichia coli* K12 regains its O antigen. Microbiology 140 (Pt 1), 49-57 (1994).
36. Chen, L. et al. Outer membrane vesicles displaying engineered glycotopes elicit protective antibodies. Proc Natl Acad Sci USA 113, E3609-18 (2016).
37. Kwon, Y. C. & Jewett, M. C. High-throughput preparation methods of crude extract for robust cell-free protein synthesis. Sci Rep 5, 8663 (2015).
38. Schwarz, F. et al. Relaxed acceptor site specificity of bacterial oligosaccharyltransferase in vivo. Glycobiology 21, 45-54 (2011).
39. Schwarz, F. et al. A combined method for producing homogeneous glycoproteins with eukaryotic N-glycosylation. Nat Chem Biol 6, 264-6 (2010).
40. Jervis, A. J. et al. Characterization of the structurally diverse N-linked glycans of *Campylobacter* species. J Bacteriol 194, 2355-62 (2012).
41. Hagelueken, G. et al. A coiled-coil domain acts as a molecular ruler to regulate O-antigen chain length in lipopolysaccharide. Nat Struct Mol Biol 22, 50-56 (2015).
42. Srichaisupakit, A., Ohashi, T., Misaki, R. & Fujiyama, K. Production of initial-stage eukaryotic N-glycan and its protein glycosylation in *Escherichia coli*. J Biosci Bioeng 119, 399-405 (2015).
43. Jewett, M. C., Calhoun, K. A., Voloshin, A., Wuu, J. J. & Swartz, J. R. An integrated cell-free metabolic platform for protein production and synthetic biology. Mol Syst Biol 4, 220 (2008).
44. Jackson, K., Kanamori, T., Ueda, T. & Fan, Z. H. Protein synthesis yield increased 72 times in the cell-free PURE system. Integr Biol (Camb) 6, 781-8 (2014).
45. Stech, M. et al. Cell-free synthesis of functional antibodies using a coupled in vitro transcription-translation system based on CHO cell lysates. Sci Rep 7, 12030 (2017).
46. Ahn, J. H., Hwang, M. Y., Lee, K. H., Choi, C. Y. & Kim, D. M. Use of signal sequences as an in situ removable sequence element to stimulate protein synthesis in cell-free extracts. Nucleic Acids Res 35, e21 (2007).
47. Schoborg, J. A. et al. A cell-free platform for rapid synthesis and testing of active oligosaccharyltransferases. Biotechnol Bioeng 115, 739-750 (2018).
48. Sun, Z. Z. et al. Protocols for implementing an *Escherichia coli* based TX-TL cell-free expression system for synthetic biology. J Vis Exp, e50762 (2013).
49. Hayes, C. Biomolecular Breadboards: Protocols: cost estimate. http://www.openwetware.org/wiki/Biomolecular_Breadboards:Protocols:cost_estimate. Vol. 2017 (2012).
50. Ollis, A. A. et al. Substitute sweeteners: diverse bacterial oligosaccharyltransferases with unique N-glycosylation site preferences. Sci Rep 5, 15237 (2015).
51. Ramirez, A. S. et al. Characterization of the single-subunit oligosaccharyltransferase STT3A from *Trypanosoma brucei* using synthetic peptides and lipid-linked oligosaccharide analogs. Glycobiology 27, 525-535 (2017).
52. Lizak, C., Gerber, S., Numao, S., Aebi, M. & Locher, K. P. X-ray structure of a bacterial oligosaccharyltransferase. Nature 474, 350-5 (2011).
53. Musumeci, M. A. et al. In vitro activity of Neisseria meningitidis PglL O-oligosaccharyltransferase with diverse synthetic lipid donors and a UDP-activated sugar. J Biol Chem 288, 10578-87 (2013).
54. Glover, K. J., Weerapana, E., Numao, S. & Imperiali, B. Chemoenzymatic synthesis of glycopeptides with PglB, a bacterial oligosaccharyl transferase from *Campylobacter jejuni*. Chem Biol 12, 1311-5 (2005).
55. Kightlinger, W. et al. Design of glycosylation sites by rapid synthesis and analysis of glycosyltransferases. Nat Chem Biol (2018).
56. Merritt, J. H., Ollis, A. A., Fisher, A. C. & DeLisa, M. P. Glycans-by-design: engineering bacteria for the biosynthesis of complex glycans and glycoconjugates. Biotechnol Bioeng 110, 1550-64 (2013).
57. Pardee, K. et al. Paper-based synthetic gene networks. Cell 159, 940-54 (2014).
58. Salehi, A. S. et al. Cell-free protein synthesis of a cytotoxic cancer therapeutic: Onconase production and a just-add-water cell-free system. Biotechnol J 11, 274-81 (2016).
59. Pardee, K. et al. Portable, on-demand biomolecular manufacturing. Cell 167, 248-259 e12 (2016).
60. Baba, T. et al. Construction of *Escherichia coli* K-12 in-frame, single-gene knockout mutants: the Keio collection. Mol Syst Biol 2, 2006 0008 (2006).
61. Datsenko, K. A. & Wanner, B. L. One-step inactivation of chromosomal genes in *Escherichia coli* K-12 using PCR products. Proc Natl Acad Sci USA 97, 6640-5 (2000).

62. Schoborg, J. A. et al. A cell-free platform for rapid synthesis and testing of active oligosaccharyltransferases. bioRxiv (2017).
63. Bundy, B. C. & Swartz, J. R. Site-specific incorporation of p-propargyloxyphenylalanine in a cell-free environment for direct protein-protein click conjugation. Bioconjug Chem 21, 255-63 (2010).
64. Kowarik, M. et al. N-linked glycosylation of folded proteins by the bacterial oligosaccharyltransferase. Science 314, 1148-50 (2006).
65. Jaroentomeechai, T. et al. A Pipeline for Studying and Engineering Single-Subunit Oligosaccharyltransferases. Methods Enzymol 597, 55-81 (2017).
66. Jewett, M. C. & Swartz, J. R. Mimicking the *Escherichia coli* cytoplasmic environment activates long-lived and efficient cell-free protein synthesis. Biotechnol Bioeng 86, 19-26 (2004).
67. Pettersen, E. F. et al. UCSF Chimera—a visualization system for exploratory research and analysis. J Comput Chem 25, 1605-12 (2004).
68. Ollis, A. A., Zhang, S., Fisher, A. C. & DeLisa, M. P. Engineered oligosaccharyltransferases with greatly relaxed acceptor-site specificity. Nat Chem Biol 10, 816-22 (2014).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A cell-free platform for performing glycoprotein synthesis of a target protein, the platform comprising a cell-free lysate from a genetically modified strain of Escherichia coli (E. coli) bacteria comprising:
   a heterologous oligosaccharyltransferase (OST) gene which is expressed in the modified strain of E. coli bacteria and which encodes an OST enzyme, wherein the OST enzyme is a component of the cell-free lysate; and wherein the lysate does not comprise the target protein.

2. The cell-free platform of claim 1, wherein the heterologous OST gene is from Campylobacter jejuni, Campylobacter coli, Campylobacter Zari, Desulfovibrio desulfricans, Desulfovibrio gigas, or Desulfovibrio vulgaris.

3. The cell-free platform of claim 1, wherein the heterologous OST gene is from Campylobacter jejuni (C. jejuni).

4. The cell-free platform of claim 3, wherein the heterologous OST gene comprises pglB.

5. The cell-free platform of claim 1, wherein the genetically modified strain of bacteria comprises one or both of (a) an inactivated or deleted gene encoding an enzyme in the glycosyltransferase pathway; (b) an inactivated or deleted gene encoding an enzyme that metabolizes a monosaccharide or polysaccharide that is a substrate in glycosylation.

6. The cell-free platform of claim 5, wherein the inactivated or deleted gene encoding an enzyme in the glycosyltransferase pathway comprises a mutation in an endogenous waaL gene that inactivates the waaL gene.

7. The cell-free platform of claim 5, wherein the inactivated or deleted gene encoding an enzyme that metabolizes a monosaccharide or polysaccharide that is a substrate in glycosylation comprises a mutation in an endogenous gmd gene that inactivates the gmd gene.

8. The cell-free platform of claim 5, wherein the genetically modified strain of bacteria comprises a mutation in an endogenous waaL gene that inactivates the waaL gene and a mutation in an endogenous gmd gene that inactivates the gmd gene.

9. The cell-free platform of claim 1, wherein the lysate comprises crude cell lysates.

10. The cell-free platform of claim 1, wherein the cell-free lysate is enriched in lipid-linked oligosaccharides (LLO).

11. The cell-free platform of claim 10, wherein the cell-free lysate is enriched in (a) $Man_3GlcNAc_2$ LLO; or (b) $Man_3GlcNAc_4Gal_2Neu_5Ac_2$ LLO.

12. The cell-free platform of claim 1, wherein the cell-free lysate is enriched in (a) $Man_3GlcNAc_2$; or (b) $Man_3GlcNAc_4Gal_2Neu_5Ac_2$.

13. The cell-free platform of claim 1, wherein the cell-free lysate is enriched in glycosyltransferases (GTs).

14. The cell-free platform of claim 1, comprising bacterial transcription and translation machinery.

15. The cell-free platform of claim 1, wherein the cell-free lysate has been preserved by freeze-drying or lyophilization.

16. The cell-free platform of claim 10, wherein the LLOs comprise a truncated form of $Man_3GlcNAc_4Gal_2Neu_5Ac_2$.

17. The cell-free platform of claim 10, wherein the LLOs comprising GlcNAc as the reducing end sugar.

* * * * *

SEQUENCE LISTING

```
Sequence total quantity: 12
SEQ ID NO: 1           moltype = DNA  length = 1122
FEATURE                Location/Qualifiers
source                 1..1122
                       mol_type = genomic DNA
                       organism = Escherichia coli
SEQUENCE: 1
atgtcaaaag tcgctctcat caccggtgta accggacaag acggttctta cctggcagag   60
tttctgctgg aaaaaggtta cgaggtgcat ggtattaagc gtcgcgcatc gtcattcaac  120
accgagcgcg tggatcacat ttatcaggat ccgcacacct gcaacccgaa attccatctg  180
cattatgcga acctgagtga tacctctaac ctgacgcgca ttttgcgtga agtacagccg  240
gatgaagtgt acaacctggg cgcaatgagc cacgttgcgg tctcttttga gtcaccagaa  300
tataccgctg acgtcgacgc gatgggtacg ctgcgcctgc tggaggcgat ccgcttcctc  360
ggtctggaaa agaaaactcg tttctatcag gcttccacct ctgaactgta tggtctggtg  420
caggaaattc cgcagaaaga gaccacgccg ttctacccgc gatctccgta tgcggtcgcc  480
aaactgtacg cctactggat caccgttaac taccgtgaat cctacgcat gtacgcctgt  540
aacggaattc tcttcaacca tgaatcccg cgccgcggcg aaaccttcgt tacccgcaaa  600
atcacccgcg caatcgccaa catcgcccag gggctggagt cgtgcctgta cctcggcaat  660
atggattccc tgcgtgactg gggccacgcc aaagactacg taaaaatgca gtggatgatg  720
ctgcagcagg aacagccgga agatttcgtt atcgcgaccg gcgttcagta ctccgtgcgt  780
cagttcgtgg aaatggcggc agcacagctg ggcatcaaac tgcgctttga aggcacgggc  840
gttgaagaga agggcattgt ggtttccgtc accgggcatg acgcgccggg cgttaaaccg  900
ggtgatgtga ttatcgctgt tgaccgcgt tacttccgtc cggctgaagt tgaaacgctg  960
ctcggcgacc cgaccaaagc gcacgaaaaa ctgggctgga aaccggaaat cacctcaga  1020
gagatggtgt ctgaaatggt ggctaatgac ctcgaagcgg cgaaaaaaca ctctctgctg  1080
aaatctcacg gctacgacgt ggcgatcgcg ctggagtcat aa                    1122

SEQ ID NO: 2           moltype = AA  length = 373
FEATURE                Location/Qualifiers
source                 1..373
                       mol_type = protein
                       organism = Escherichia coli
SEQUENCE: 2
MSKVALITGV TGQDGSYLAE FLLEKGYEVH GIKRRASSFN TERVDHIYQD PHTCNPKFHL   60
HYGDLSDTSN LTRILREVQP DEVYNLGAMS HVAVSFESPE YTADVDAMGT LRLLEAIRFL  120
GLEKKTRFYQ ASTSELYGLV QEIPQKETTP FYPRSPYAVA KLYAYWITVN YRESYGMYAC  180
NGILFNHESP RRGETFVTRK ITRAIANIAQ GLESCLYLGN MDSLRDWGHA KDYVKMQWMM  240
LQQEQPEDFV IATGVQYSVR QFVEMAAAQL GIKLRFEGTG VEEKGIVVSV TGHDAPGVKP  300
GDVIIAVDPR YFRPAEVETL LGDPTKAHEK LGWKPEITLR EMVSEMVAND LEAAKKHSLL  360
KSHGYDVAIA LES                                                     373
```

```
SEQ ID NO: 3              moltype = DNA   length = 1260
FEATURE                   Location/Qualifiers
source                    1..1260
                          mol_type = genomic DNA
                          organism = Escherichia coli
SEQUENCE: 3
atgctaacat cctttaaact tcattcattg aaaccttaca ctctgaaatc atcaatgatt   60
ttagagataa taacttatat attatgtttt ttttcaatga taattgcatt cgtcgataat  120
actttcagca taaaaatata taatatcact gctatagttt gcttattgtc actaattta   180
cgtggcagac aagaaaatta taatataaaa aaccttattc ttccccttc tatattttta   240
ataggcttgc ttgatttaat ttggtattct gcgtttaaag tagataattc gccatttcgt  300
gctacttacc atagttattt aaatactgcc aaaatattta tatttggttc ttttattgtt  360
tcttgacac taactagcca gctaaaatca aaaaaagaga gtgtattata cactttgtat  420
tctctgtcat ttctaattgc tggatatgca atgtatatta atagcattca tgaaaatgac  480
cgcatttctt ttggtgtagg aacggcaaca ggagcagcat attcaacaat gctaataggg  540
atagttagtg gcgttgcgat tctttatact aagaaaaatc atcctttttt attttttatta 600
aatagttgcg cggtacttta tgttctggcg ctaaacaaaa ccagagcaac cctactcctg  660
ttccctataa tttgtgttgc tgcattaata gcttattata taaatcacc caagaaattc   720
acttcctcta ttgttctact aattgctata ttagctagca ttgttattat atttaataaa  780
ccaatacaga atcgctataa tgaagcatta aatgacttaa acagttatac caatgctaat  840
agtgttactt ccctaggtgc aagactggca atgtacgaaa ttggtttaaa tatattcata  900
aagtcacctt tttcatttag atcagcgaga tcacgcgctg aaagtatgaa tttgttagtt  960
gcagaacaca ataggctaag aggggcattg gagttttcta acgtacatct acataatgag 1020
ataattgaag cagggtcact gaaaggtctg atgggaattt tttccacact tttcctctat 1080
ttttcactat tttatatagc ataaaaaaa cgagcttttg gtttgttgat attaacgctt  1140
ggcattgtgg ggattggact cagtgatgtg atcatatggg cacgcagtat tccaattatc 1200
attatatccg ctatagtcct cttactcgtc attaataatc gtaacaatac aattaattaa 1260

SEQ ID NO: 4              moltype = AA    length = 419
FEATURE                   Location/Qualifiers
source                    1..419
                          mol_type = protein
                          organism = Escherichia coli
SEQUENCE: 4
MLTSFKLHSL KPYTLKSSMI LEIITYILCF SMIIAFVDN TFSIKIYNIT AIVCLLSLIL    60
RGRQENYNIK NLILPLSIFL IGLLDLIWYS APKVDNSPFR ATYHSYLNTA KIFIFGSFIV  120
FLTLTSQLKS KKESVLYTLY SLSFLIAGYA MYINSIHEND RISFGVGTAT GAAYSTMLIG  180
IVSGVAILYT KKNHPFLFLL NSCAVLYVLA LTQTRATLLL FPIICVAALI AYYNKSPKKF  240
TSSIVLLIAI LASIVIIFNK PIQNRYNEAL NDLNSYTNAN SVTSLGARLA MYEIGLNIFI  300
KSPFSFRSAE SRAESMNLLV AEHNRLRGAL EFSNVHLHNE IIEAGSLKGL MGIFSTLFLY  360
FSLFYIAYKK RALGLLILTL GIVGIGLSDV IIWARSIPII IISAIVLLLV INNRNNTIN   419

SEQ ID NO: 5              moltype = AA   length = 5
FEATURE                   Location/Qualifiers
REGION                    1..5
                          note = Sequon for N-glycosylation
source                    1..5
                          mol_type = protein
                          organism = synthetic construct
SEQUENCE: 5
AQNAT                                                                 5

SEQ ID NO: 6              moltype = AA   length = 5
FEATURE                   Location/Qualifiers
REGION                    1..5
                          note = Sequon for N-glycosylation
source                    1..5
                          mol_type = protein
                          organism = synthetic construct
SEQUENCE: 6
DQNAT                                                                 5

SEQ ID NO: 7              moltype = AA   length = 5
FEATURE                   Location/Qualifiers
REGION                    1..5
                          note = Sequon for N-glycosylation
source                    1..5
                          mol_type = protein
                          organism = synthetic construct
SEQUENCE: 7
AENIT                                                                 5

SEQ ID NO: 8              moltype = AA   length = 5
FEATURE                   Location/Qualifiers
REGION                    1..5
                          note = Sequon for N-glycosylation
source                    1..5
                          mol_type = protein
```

```
                          organism = synthetic construct
SEQUENCE: 8
NENIT                                                                       5

SEQ ID NO: 9              moltype = AA   length = 5
FEATURE                   Location/Qualifiers
REGION                    1..5
                          note = Sequon for N-glycosylation
source                    1..5
                          mol_type = protein
                          organism = synthetic construct
SEQUENCE: 9
LVNSS                                                                       5

SEQ ID NO: 10             moltype = AA   length = 22
FEATURE                   Location/Qualifiers
REGION                    1..22
                          note = Peptide for N-glycosylation
source                    1..22
                          mol_type = protein
                          organism = synthetic construct
SEQUENCE: 10
LISEEDLNGA ALEGGDQNAT GK                                                   22

SEQ ID NO: 11             moltype = DNA  length = 2142
FEATURE                   Location/Qualifiers
source                    1..2142
                          mol_type = genomic DNA
                          organism = Campylobacter jejuni
SEQUENCE: 11
atgttgaaaa aagagtattt aaaaaaccct tatttagttt tgtttgcgat gattgtatta         60
gcttatgttt ttagtgtatt ttgcaggttt tattgggttt ggtgggcaag tgagtttaac        120
gagtattttt tcaataatca attaatgatc atttcaaacg atggctatgc ttttgctgag        180
ggcgcaagag atatgatagc aggttttcat cagcctaatg atttgagtta ttatggatct        240
tctttatcta cgcttactta ttggctttat aaaaatcaca ctttttcttt tgaaagtatc        300
attttatata tgagtacttt tttatcttct tggtggtga ttcctattat tttactagct         360
aatgaataca aacgcccttt aatgggcttt gtagctgctc ttttagcaag tgtagcaaac        420
agttattata atcgcactat gagtgggtat tatgatacgg atatgctggt aattgttcta        480
cctatgttta tttttatttt tatggtaaga atgatttaa aaaaagactt tttttcattg         540
attgccttgc cattatttat aggaatttat ctttggtggt atccttcaag ttatacttta        600
aatgtagctt taattggact ttttttaatt tatacactta ttttttcatag aaaagaaaag       660
atttttttata tagctgtgat tttgtcttct cttactcttt caaatatagc atggttttat       720
caaagtgcca ttatagtaat acttttttgct ttatttgctt tagagcaaaa acgcttaaat       780
tttatgatta taggaatttt aggtagtgca actttgatat ttttgatttt aagtggtggg        840
gttgatccca tactttatca gcttaaattt tatattttta gaagcgatga agtgcgaat         900
ttaacacagg gctttatgta tttaatgttt aatcaaacca tacaagaagt tgaaaatgta        960
gatttagcg aaatttatgcg aagaattagt ggtagtgaaa ttgtttttct gtttttctttg      1020
tttggttttg tatggctttt gagaaaacat aaaaagtatga ttatggcttt acctatattg      1080
gtgcttgggt tttagcctt aaaaggagga cttagattta ccatttattc tgtacctgta        1140
atggctttag gatttggttt tttattgagc gagtttaagg ctatattggt taaaaaatat       1200
agccaattaa cttcaaatgt ttgtattgtt tttgcaacta ttttgacttt ggctccagtg       1260
tttatccata tttacaacta taaagcgcca acagttttttt ctcaaaatga agcatcatta      1320
ttaaatcaat taaaaaatat agccaataga aagattatg tggtaacttg gtgggattat        1380
ggttatcctg tgcgttatta tagcgatgtg aaaactttag tagatggtgg aaagcattta       1440
ggtaaggata attttttccc ttcttttttct ttaagtaaag atgaacaagc tgcagctaat     1500
atggcaagac ttagtgtaga atatacagaa aaaagcttt atgctccgca aatgatatt        1560
ttaaaatcag acatttttaca agccatgatg aagattata atcaaagcaa tgtggattta      1620
tttctagctt cattatcaaa acctgatttt aaaatcgata caccaaaac tcgtgatatt       1680
tatctttata tgcccgctag aatgtctttg atttttttca cggtcggctg ttttttcttt      1740
attaatttag atacaggagt tttggataaa cctttttacct ttagcacagc ttatccactt      1800
gatgttaaaa atggagaaat ttatcttagc aacggagtgg ttttaagcga tgatttaga       1860
agttttaaaa taggtgataa tgtggttttct gtaaatagta tcgtagagat taattctatt     1920
aaacaaggtg aatacaaaat cactccaatc gatgataagg ctcagtttta tatttttttat     1980
ttaaaggata gtgctattcc ttacgcacaa tttattttaa tggataaaac catgttttaat      2040
agtgcttatg tgcaaatgtt ttttttggga aattatgata agaatttatt tgacttggtg       2100
attaattcta gagatgctaa agtttttaaa cttaaaattt aa                          2142

SEQ ID NO: 12             moltype = AA   length = 713
FEATURE                   Location/Qualifiers
source                    1..713
                          mol_type = protein
                          organism = Campylobacter jejuni
SEQUENCE: 12
MLKKEYLKNP YLVLFAMIVL AYVFSVFCRF YWVWWASEFN EYFFNNQLMI ISNDGYAFAE        60
GARDMIAGFH QPNDLSYYGS SLSTLTYWLY KITPFSFESI ILYMSTFLSS LVVIPIILLA       120
NEYKRPLMGF VAALLASVAN SYYNRTMSGY YDTDMLVIVL PMFILFFMVR MILKKDFFSL       180
IALPLFIGIY LWWYPSSYTL NVALIGLFLI YTLIFHRKEK IFYIAVILSS LTLSNIAWFY       240
QSAIIVILFA LFALEQKRLN FMIIGILGSA TLIFLILSGG VDPILYQLKF YIFRSDESAN      300
LTQGFMYFNV NQTIQEVENV DFSEFMRRIS GSEIVFLFSL FGFVWLLRKH KSMIMALPIL      360
```

-continued

```
VLGFLALKGG  LRFTIYSVPV  MALGFGFLLS  EFKAILVKKY  SQLTSNVCIV  FATILTLAPV  420
FIHIYNYKAP  TVFSQNEASL  LNQLKNIANR  EDYVVTWWDY  GYPVRYYSDV  KTLVDGGKHL  480
GKDNFFPSFS  LSKDEQAAAN  MARLSVEYTE  KSFYAPQNDI  LKSDILQAMM  KDYNQSNVDL  540
FLASLSKPDF  KIDTPKTRDI  YLYMPARMSL  IFSTVASFSF  INLDTGVLDK  PFTFSTAYPL  600
DVKNGEIYLS  NGVVLSDDFR  SFKIGDNVVS  VNSIVEINSI  KQGEYKITPI  DDKAQFYIFY  660
LKDSAIPYAQ  FILMDKTMFN  SAYVQMFFLG  NYDKNLFDLV  INSRDAKVFK  LKI         713
```